United States Patent
Cravatt et al.

(10) Patent No.: US 11,691,984 B2
(45) Date of Patent: Jul. 4, 2023

(54) COMPOUNDS AND METHODS FOR DCAF-MEDIATED PROTEIN DEGRADATION

(71) Applicant: The Scripps Research Institute, La Jolla, CA (US)

(72) Inventors: Benjamin Cravatt, La Jolla, CA (US); Vincent Crowley, San Diego, CA (US); Xiaoyu Zhang, San Diego, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 16/600,326

(22) Filed: Oct. 11, 2019

(65) Prior Publication Data

US 2020/0190105 A1    Jun. 18, 2020

Related U.S. Application Data

(60) Provisional application No. 62/745,076, filed on Oct. 12, 2018.

(51) Int. Cl.
*C07D 495/14* (2006.01)
*C07B 59/00* (2006.01)

(52) U.S. Cl.
CPC .......... *C07D 495/14* (2013.01); *C07B 59/002* (2013.01); *C07B 2200/05* (2013.01)

(58) Field of Classification Search
CPC .. C07D 495/14; C07B 59/002; C07B 2200/05
See application file for complete search history.

(56) References Cited

U.S. PATENT DOCUMENTS

| | | |
|---|---|---|
| 9,254,311 B2 | 2/2016 | Bancel et al. |
| 2018/0118758 A1 | 5/2018 | Jacques |
| 2018/0228907 A1 | 8/2018 | Crew et al. |

FOREIGN PATENT DOCUMENTS

| | | |
|---|---|---|
| WO | WO-2017007612 A1 | 1/2017 |
| WO | WO-2017024317 A2 | 2/2017 |
| WO | WO-2017024318 A1 | 2/2017 |
| WO | WO-2017210600 A1 | 12/2017 |
| WO | WO-2018119448 A1 | 6/2018 |
| WO | WO-2018148440 A1 | 8/2018 |
| WO | WO-2018148443 A1 | 8/2018 |
| WO | WO-2018187401 A1 | 10/2018 |
| WO | WO-2019165229 A1 | 8/2019 |
| WO | WO-2020077278 A1 | 4/2020 |

OTHER PUBLICATIONS

Backus et al. Proteome-wide covalent ligand discovery in native biological systems. Nature 534(7608):570-574 (2016).
Bondeson et al. Lessons in PROTAC Design from Selective Degradation with a Promiscuous Warhead. Cell Chem Biol 25:78-87.e5 (2018).
Bondeson, et al., Catalytic in vivo protein knockdown by small-molecule PROTACs. Nat Chem Biol, Aug. 2015; 11(8):611-617.
Buckley et al. Small-molecule inhibitors of the interaction between the E3 ligase VHL and HIF1α. Angew Chem Int Ed Engl 51:11463-11467 (2012).
Filippakopoulos et al. Selective inhibition of BET bromodomains. Nature 468:1067-1073 (2010).
Gadd et al. Structural basis of PROTAC cooperative recognition for selective protein degradation. Nat Chem Biol 13:514-521 (2017).
Huang et al. A Chemoproteomic Approach to Query the Degradable Kinome Using a Multi-kinase Degrader. Cell Chem Biol 25:88-99 (2018).
Ito et al. Identification of a primary target of thalidomide teratogenicity. Science 327:1345-1350 (2010).
Jin et al., A family of diverse Cul4-Ddb1-interacting proteins includes Cdt2, which is required for S phase destruction of the replication factor Cdt1. Molecular Cell. 23(5):709-721 (2006).
Nabet et al. The dTAG system for immediate and target-specific protein degradation. Nat Chem Biol 14:431-441 (2018).
Raina et al. PROTAC-induced BET protein degradation as a therapy for castration-resistant prostate cancer. PNAS USA 113:7124-7129 (2016).
Soucy et al. An inhibitor of NEDD8-activating enzyme as a new approach to treat cancer. Nature 458:732-736 (2009).
Vassilev et al. In vivo activation of the p53 pathway by small-molecule antagonists of MDM2. Science 303:844-848 (2004).
Weerapana et al. Quantitative reactivity profiling predicts functional cysteines in proteomes. Nature 468:790-795 (2010).
Winter et al. Drug Development. Phthalimide conjugation as a strategy for in vivo target protein degradation. Science 348:1376-1381 (2015).
Xu et al. ProLuCID: An improved SEQUEST-like algorithm with enhanced sensitivity and specificity. J Proteomics 129:16-24 (2015).
Cal et al. Cysteine-selective reactions for antibody conjugation. Angewandte Chemi International Edition 53:10585-10587 (2014).
PCT/US2019/055958 International Search Report and Written Opinion dated Feb. 3, 2020.
Zhang et al. Electrophilic PROTACs that degrade nuclear proteins by engaging DCAF16. Nature Chemical Biology 15:737-746 (2019).
Chen et al. Plant E3 Ligases: Flexible Enzymes in a Sessile World. Molecular Plant 6(5):1388-1404 (2013).
Deshaies et al. RING Domain E3 Ubiquitin Ligases. Annual Review Of Biochemistry 78(1):399-434 (2009).

*Primary Examiner* — Paul J Holland
(74) *Attorney, Agent, or Firm* — Wilson Sonsini Goodrich & Rosati

(57) ABSTRACT

Disclosed herein are methods and compounds for inducing DDB1- and CUL4-associated factor 16 (DCAF16)-mediated protein degradation in mammalian cells. In some embodiments, also disclosed herein are methods of modulating the substrate selectivity of a DCAF16-CUL4-RBX1-DDB1 complex (CRL4) for modulating protein degradation.

17 Claims, 29 Drawing Sheets
Specification includes a Sequence Listing.

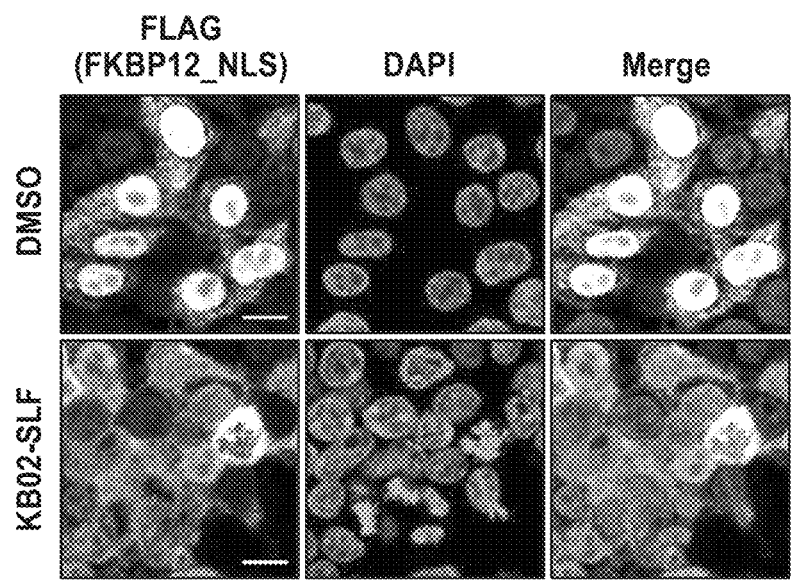
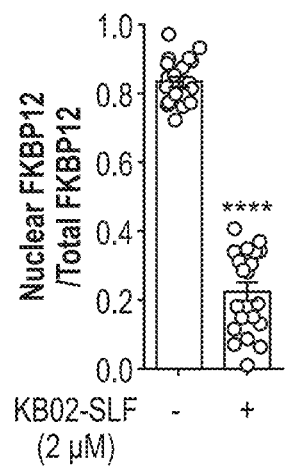
FIG. 1C
FIG. 1D
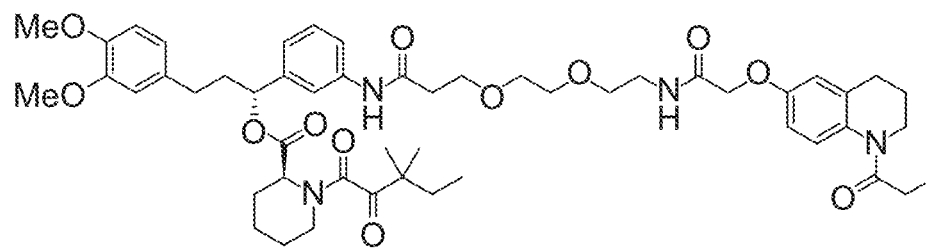
FIG. 1E
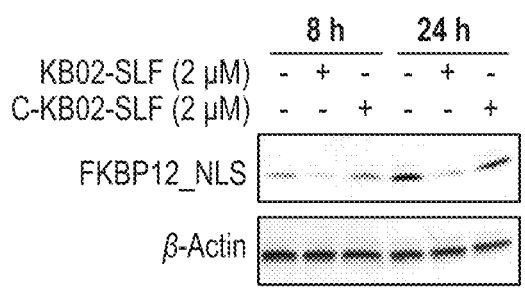
FIG. 1F
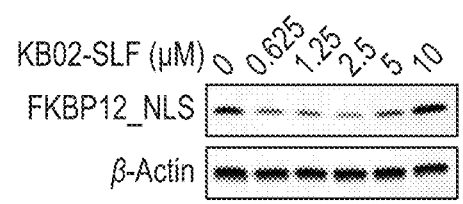
FIG. 1G

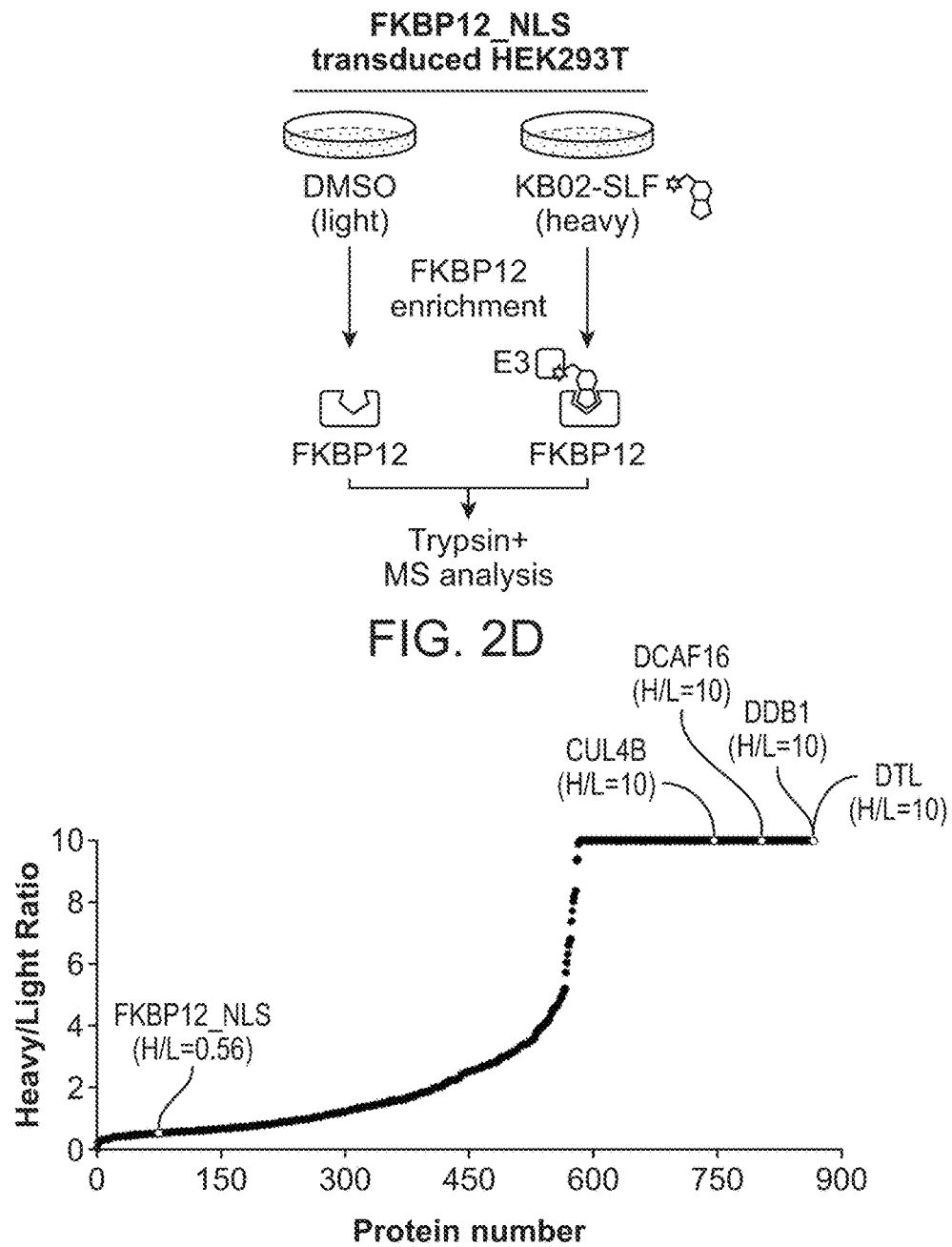
FIG. 2D
FIG. 2E
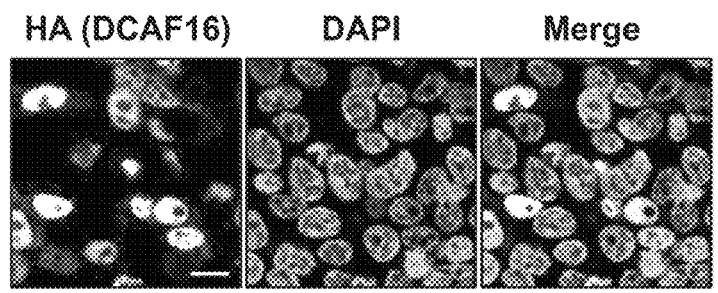
FIG. 2F

| Protein | FKBP12_NLS Replicate1 | | FKBP12_NLS Replicate2 | | FKBP12_NLS Replicate3 | | pCDH Replicate1 | | pCDH Replicate2 | |
|---|---|---|---|---|---|---|---|---|---|---|
| | H/L | SC | H/L | SC | H/L | SC | H/L | SC | H/L | SC |
| DCAF16 | 10 | 16 | 10 | 10 | 10 | 6 | ND | ND | ND | ND |
| DTL | 10 | 38 | 10 | 20 | ND | ND | ND | ND | ND | ND |
| DDB1 | 10 | 272 | 10 | 194 | 10 | 132 | ND | ND | ND | ND |
| CUL4B | 10 | 10 | ND | ND | ND | ND | ND | ND | ND | ND |
| FKBP12 | 0.55 | 13272 | 0.62 | 2668 | 0.74 | 2736 | ND | ND | ND | ND |

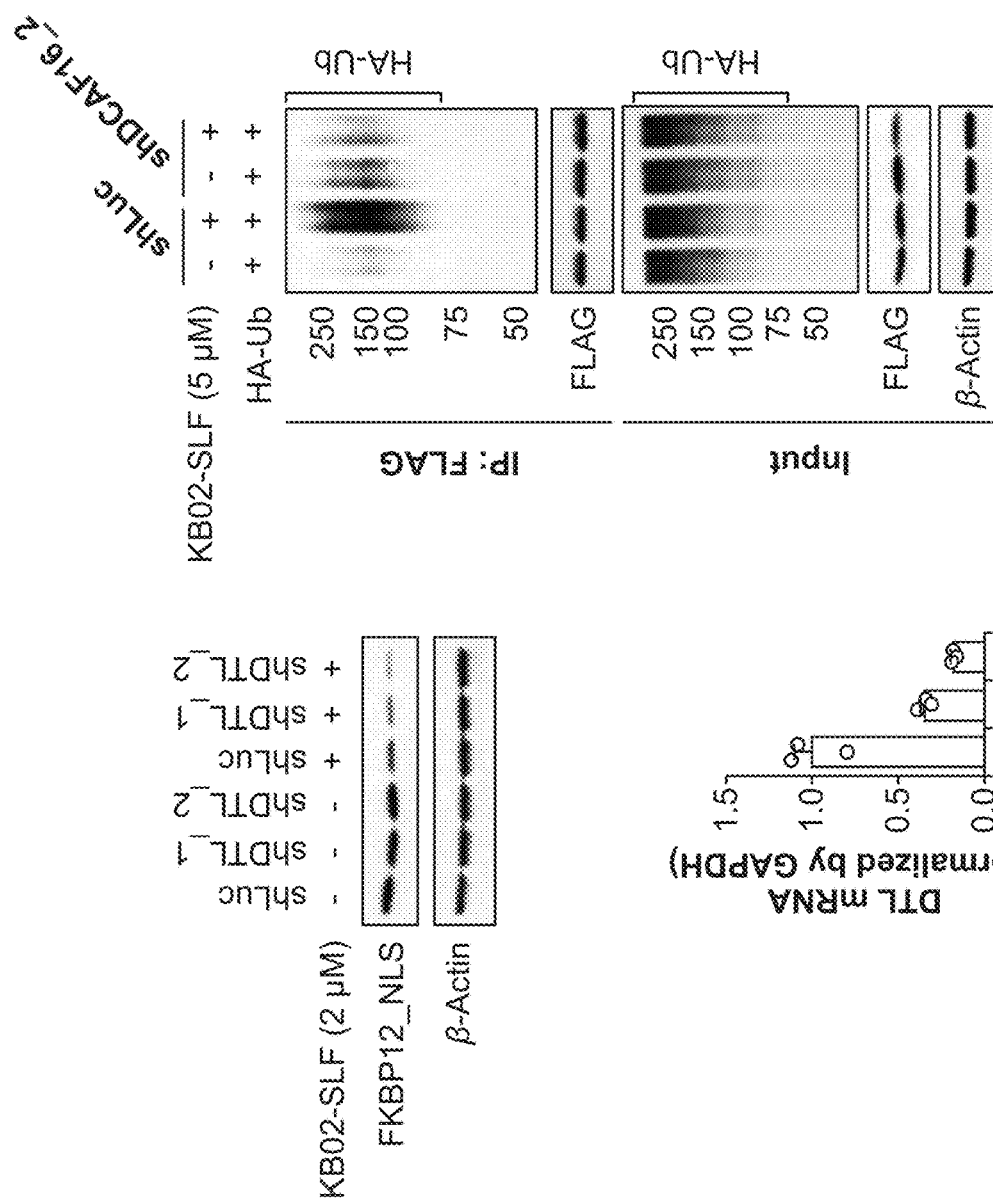

| Clone 6 vs. Clone | DCAF16 | | | DDB1 | | | FKBP12 | | |
|---|---|---|---|---|---|---|---|---|---|
| | Light SC | Heavy SC | H/L ratio | Light SC | Heavy SC | H/L ratio | Light SC | Heavy SC | H/L ratio |
| 17 | 2 | 5 | 1.3 | 50 | 51 | 1.2 | 1538 | 1048 | 0.68 |
| 18 | 4 | 3 | 1.4 | 39 | 61 | 1.1 | 1381 | 975 | 0.64 |
| 3 | 0 | 2 | - | 3 | 38 | 4.7 | 2386 | 1456 | 0.57 |
| 4 | 0 | 5 | 10 | 7 | 68 | 3.8 | 2761 | 1731 | 0.66 |
| 22 | 0 | 5 | 10 | 5 | 45 | 2.6 | 1764 | 979 | 0.48 |

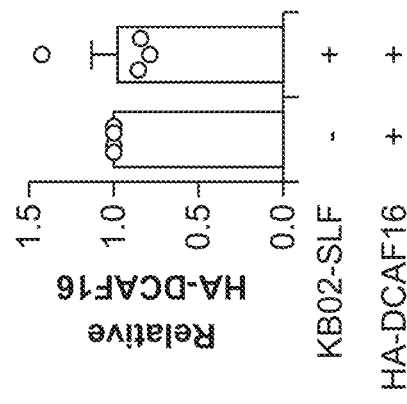
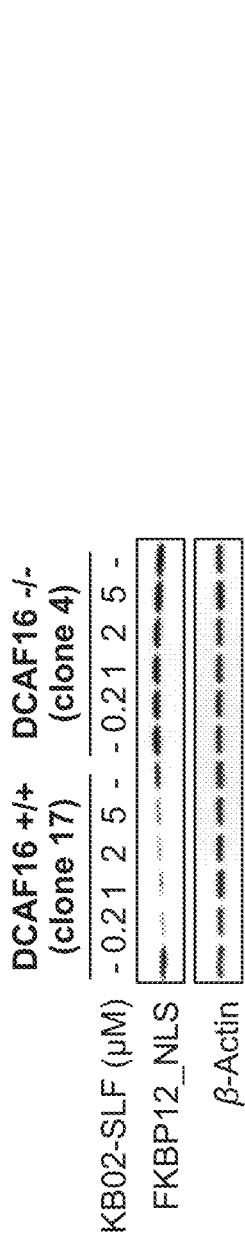
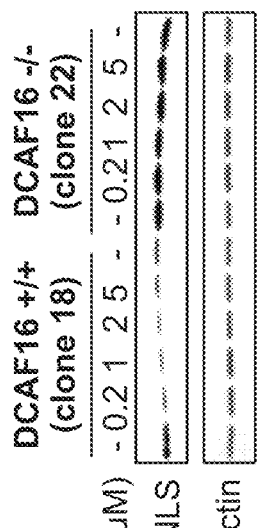
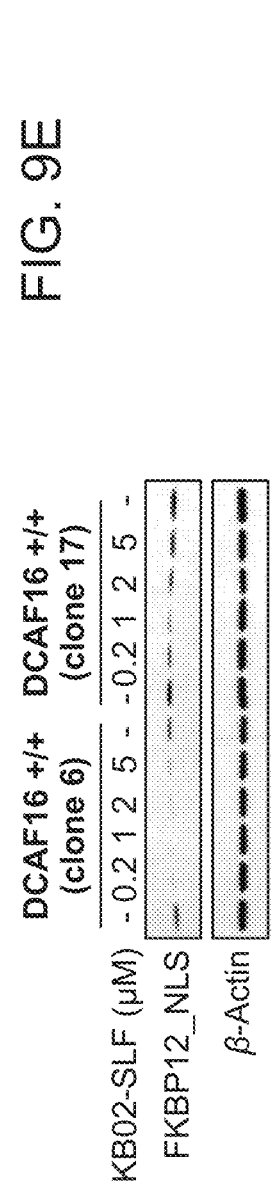
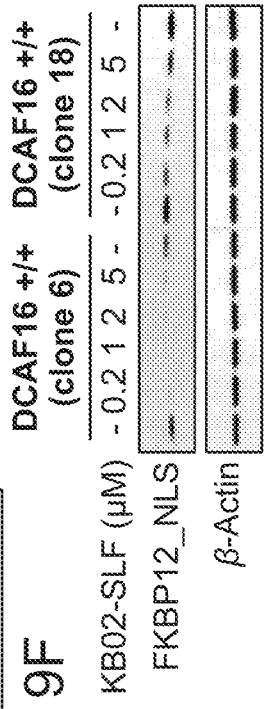

SEQUENCE LISTING

<160> NUMBER OF SEQ ID NOS: 20

<210> SEQ ID NO 1
<211> LENGTH: 216
<212> TYPE: PRT
<213> ORGANISM: Homo sapiens

<400> SEQUENCE: 1

```
Met Gly Pro Arg Asn Pro Ser Pro Asp His Leu Ser Glu Ser Glu Ser
1               5                   10                  15

Glu Glu Glu Glu Asn Ile Ser Tyr Leu Asn Glu Ser Ser Gly Glu Glu
                20                  25                  30

Trp Asp Ser Ser Glu Glu Glu Asp Ser Met Val Pro Asn Leu Ser Pro
            35                  40                  45

Leu Glu Ser Leu Ala Trp Gln Val Lys Cys Leu Leu Lys Tyr Ser Thr
    50                  55                  60

Thr Trp Lys Pro Leu Asn Pro Asn Ser Trp Leu Tyr His Ala Lys Leu
65                  70                  75                  80

Leu Asp Pro Ser Thr Pro Val His Ile Leu Arg Glu Ile Gly Leu Arg
                85                  90                  95

Leu Ser His Cys Ser His Cys Val Pro Lys Leu Glu Pro Ile Pro Glu
            100                 105                 110

Trp Pro Pro Leu Ala Ser Cys Gly Val Pro Pro Phe Gln Lys Pro Leu
        115                 120                 125

Thr Ser Pro Ser Arg Leu Ser Arg Asp His Ala Thr Leu Asn Gly Ala
    130                 135                 140

Leu Gln Phe Ala Thr Lys Gln Leu Ser Arg Thr Leu Ser Arg Ala Thr
145                 150                 155                 160

Pro Ile Pro Glu Tyr Leu Lys Gln Ile Pro Asn Ser Cys Val Ser Gly
                165                 170                 175

Cys Cys Cys Gly Trp Leu Thr Lys Thr Val Lys Glu Thr Thr Arg Thr
            180                 185                 190

Glu Pro Ile Asn Thr Thr Tyr Ser Tyr Thr Asp Phe Gln Lys Ala Val
        195                 200                 205

Asn Lys Leu Leu Thr Ala Ser Leu
    210                 215
```

```
<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Phe Gly
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Leu Ala Leu
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Phe Leu Gly
1

<210> SEQ ID NO 5
<211> LENGTH: 7
<212> TYPE: PRT
<213> ORGANISM: Simian virus 40

<400> SEQUENCE: 5

Pro Lys Lys Lys Arg Lys Val
1               5

<210> SEQ ID NO 6
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccggcgctga gtacttcgaa atgtcctcga ggacatttcg aagtactcag cgttttt         57

<210> SEQ ID NO 7
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ccggctggtg aacttaaact tgttactcga gtaacaagtt taagttcacc agtttttg        58
```

```
<210> SEQ ID NO 8
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ccgggcctag taacagtaac gagtactcga gtactcgtta ctgttactag gcttttg        58

<210> SEQ ID NO 9
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ccggcaaaca gctaagccga acattctcga gaatgttcgg cttagctgtt tgtttttg       59

<210> SEQ ID NO 10
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ccggtcctgg ttgtatcatg ctaaactcga gtttagcatg atacaaccag gattttg        58

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tctgacaagt ggtcaggaga                                                 20

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tattcaggta tgggagtggc tcta                                            24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gccaggattt gaaggagata ctct                                            24

<210> SEQ ID NO 14
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctgggctaca ctgagcacc                                                19

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aagtggtcgt tgagggcaat g                                             21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agtcttgcct ggcaggttaa g                                             21

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gggacttgta agaggctttt gaa                                           23

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tcactggaat gccgtctttg a                                             21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctcaccagct tttacgtccc                                               20

<210> SEQ ID NO 20
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Ile Pro Asn Ser Cys Val Ser Gly Cys Cys Cys Gly Trp Leu Thr
1               5                   10                  15

Lys
```

COMPOUNDS AND METHODS FOR DCAF-MEDIATED PROTEIN DEGRADATION

CROSS-REFERENCE TO RELATED APPLICATIONS

This application claims priority to U.S. Provisional Patent Application No. 62/745,076, filed on Oct. 12, 2018, which is hereby incorporated by reference in its entirety.

STATEMENT OF FEDERALLY SPONSORED RESEARCH

The invention disclosed herein was made, at least in part, with U.S. government support under Grant No. CA087660 by the National Institutes of Health. Accordingly, the U.S. Government has certain rights in this invention.

SEQUENCE LISTING

The instant application contains a Sequence Listing which has been filed electronically in ASCII format and is hereby incorporated by reference in its entirety. Said ASCII copy, created on Dec. 12, 2019, is named 48054-718_201_SL.txt and is 6,387 bytes in size.

BACKGROUND OF THE DISCLOSURE

Protein biosynthesis and degradation is a dynamic process which sustains normal cell metabolism. In some instances, production of new proteins modulate proliferation and differentiation of cells and upon completion, these protein are degraded through one of two proteolytic mechanisms, the lysosome degradation system or the ubiquitin proteasome pathway. In some cases, a majority of cellular proteins are degraded by the proteasome pathway, and the process is initiated via tagging of an ubiquitin.

SUMMARY OF THE DISCLOSURE

Disclosed herein, in certain embodiments, are compounds for inducing a DDB1- and CUL4-associated factor 16 (DCAF16)-mediated protein degradation. In certain embodiments, also disclosed herein are methods of modulating protein degradation based on a DCAF16-mediated process. In additional embodiments, disclosed herein are methods of modulating a substrate selectivity of a CUL4-RBX1-DDB1 complex (CRL4) and generation of diverse DCAF16 conjugates for use in said methods.

In some instances, disclosed herein is a DDB1- and CUL4-associated factor 16 (DCAF16) conjugate comprising a DCAF16 protein covalently bound to a synthetic ligand at a cysteine residue, wherein the cysteine residue is at a position corresponding to residue 58, 100, 103, 119, 173, 177, 178, or 179 of SEQ ID NO: 1.

In some instances, disclosed herein is a heterobifunctional degrader comprising a conjugated target protein biding moiety and a DDB1- and CUL4-associated factor 16 (DCAF16) binding moiety. In some embodiments, the target protein binding moiety and DCAF16 binding moiety are conjugated via a linker.

In some instances, disclosed herein is a method of modulating substrate selectivity of a CUL4-RBX1-DDB1 complex (CRL4), comprising: contacting CRL4 comprising a DCAF16 protein with a synthetic ligand for a time sufficient for the ligand to interact with a cysteine residue of the DCAF16 protein to form a CRL4-ligand complex, thereby modulating substrate selectivity of the CRL4 complex; wherein the synthetic ligand comprises a DCAF16-interacting portion linked to a substrate binding portion.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A-FIG. 1G illustrate an exemplary electrophilic bifunctional protein degrading compound that degrades nuclear FKBP12. FIG. 1A shows the structures of KB02-SLF, KB03-SLF, and KB05-SLF. FIG. 1B shows the results of a Western blot using anti-FLAG antibody of cytosolic (FLAG-FKBP12) and nuclear (FLAG-FKBP12_NLS) FKBP12 proteins expressed by stable transduction in HEK293T cells following 8 hours or 24 hours of treatment with DMSO, KB02-SLF (2 µM), KB03-SLF (2 µM), or KB05-SLF (2 µM) and the bar graphs represent the quantification of the relative FKBP12 protein content, with DMSO-treated cells set to a value of 1. Data represent mean values±SEM for 3-10 biological replicates. Statistical significance was calculated with unpaired two-tailed Student's t-tests comparing DMSO- to KB02-SLF-treated samples. **$P<0.0001$. FIG. 1B discloses "PKKKRKV" as SEQ ID NO: 5. FIG. 1C is a picture of immunofluorescent staining using anti-FLAG antibody of FLAG-FKBP12_NLS in HEK293T cells following treatment with DMSO or KB02-SLF (2 µM, 8 h). FIG. 1D is a bar graph that represents quantification of the relative nuclear to whole cell immunostaining for DMSO- and KB02-SLF-treated samples. Data represent mean values±SEM (n=20 from two biological replicates). Statistical significance was calculated with unpaired two-tailed Student's t-tests comparing DMSO to KB02-SLF-treated samples. **$P<0.0001$. Scale bar, 10 µm. FIG. 1E is the structure of non-electrophilic control compound (C-KB02-SLF). FIG. 1F shows the results of a Western blot of FLAG-FKBP12_NLS in HEK293T cells treated with KB02-SLF or C-KB02-SLF (2 µM, 8 or 24 h). FIG. 1G is a Western blot showing concentration-dependent degradation of FLAG-FKBP12_NLS by KB02-SLF in HEK293T cells (24 h treatment with indicated concentrations of KB02-SLF).

FIG. 2A-FIG. 2F illustrate characterization of KB02-SLF-mediated degradation of nuclear FKBP12. FIG. 2A is a Western blot of anti-FLAG-immunoprecipitated FLAG-FKBP12 and FLAG-FKBP12_NLS proteins analyzed for ubiquitination using an anti-HA antibody. HEK293T cells stably expressing FLAG-FKBP12 or FLAG-FKBP12_NLS were transiently transfected with HA-Ubiquitin (HA-Ub) for 24 hours and then treated with DMSO or KB02-SLF (5 µM) in the presence of the proteasome inhibitor MG132 (10 µM) for 2 hours. The Western blotting shows KB02-SLF mediated polyubiquitination of nuclear (FLAG-FKBP12_NLS), but not cytosolic (FLAG-FKBP12) in HEK293T cells. FIG. 2B is a Western blot showing KB02-SLF-mediated FLAG-FKBP12_NLS degradation is blocked by proteasome inhibitor MG132. Len-SLF is a bifunctional compound comprised of lenalidomide coupled to SLF and was used as a positive control. The bar graph represents quantification of the relative FKBP12 protein, with DMSO-treated cells set to a value of 1. Data represent mean values±SEM for 3-4 biological replicates. Statistical significance was calculated with unpaired two-tailed Student's t-tests comparing DMSO- to KB02-SLF-treated samples with or without MG132. *P<0.001; P<0.0001. FIG. 2C is a Western blot showing KB02-SLF-mediated FLAG-FKBP12_NLS degradation is blocked by neddylation inhibitor MLN4924. HEK293T cells stably expressing FLAG-FKBP12_NLS were co-treated with KB02-SLF (1 µM) and MG132 (10 µM) or MLN4924 (1 µM) for 8 h. Len-SLF was used as a positive control. The bar graph represents quantification of the relative FKBP12 protein, with DMSO-treated cells set to a value of 1. Data represent mean values±SEM for 3-4 biological replicates. Statistical significance was calculated with unpaired two-tailed Student's t-tests comparing DMSO- to KB02-SLF-treated samples with or without MLN4924. *P<0.001; ****P<0.0001. FIG. 2D is a schematic for identifying KB02-SLF-recruited E3 ubiquitin ligases by anti-FLAG affinity enrichment coupled to mass spectrometry (MS)-based proteomics. Light and heavy amino acid-labeled HEK293T cells stably expressing FLAG-FKBP12_NLS were treated with DMSO or KB02-SLF (10 respectively, for 2 hours in the presence of MG132 (10 Light and heavy cells were then lysed, subject to anti-FLAG immunoprecipitation, and the affinity-enriched proteins combined, digested with trypsin, and analyzed by LC-MS/MS. FIG. 2E is a graph showing SILAC heavy/light (H/L) ratio values of proteins identified in anti-FLAG affinity enrichment experiments (outlined in part d), where a high ratio indicates proteins selectively enriched from cells treated with KB02-SLF. FIG. 2F is a picture of immunofluorescent staining using an anti-HA antibody showing nuclear localization of HA-DCAF16 (expressed by transient transfection in HEK293T cells). Scale bar, 10 µm.

FIG. 3A is a Western blot of stably expressed FLAG-FKBP12_NLS in HEK293T cells transiently transduced with shRNAs targeting DCAF16 (sh_1 and sh_2) or a control shRNA (shLuc) followed by treatment with KB02-SLF (2 µM, 8 h). Middle graph, quantification of the relative FKBP12 protein content, with DMSO-treated cells expressing shLuc set to a value of 1. Data represent mean values±SEM for 4 biological replicates. Statistical significance was calculated with unpaired two-tailed Student's t-tests comparing DMSO to KB02-SLF-treated samples. ****P<0.0001. Right plot, DCAF16 mRNA as measured by qPCR. Data represent mean values±SEM for 3 biological replicates. FIG. 3B is a Western blot showing a concentration-dependent degradation of stably expressed FLAG-FKBP12_NLS in DCAF16+/+ (clone 6) and DCAF16−/− (clone 3) HEK293 cells following treatment with KB02-SLF for 8 hours. Bar graphs represent the quantification of the relative FKBP12 protein content, with DMSO-treated cells set to a value of 1. Data represent mean values±SEM for 3 biological replicates. Statistical significance was calculated with unpaired two-tailed Student's t-tests comparing DMSO- to KB02-SLF-treated samples. *P<0.05; *P<0.001. FIG. 3C is a Western blot showing that expression of HA-DCAF16 in DCAF16−/− cells restored KB02-SLF-mediated degradation of FLAG-FKBP12_NLS. DCAF16−/− cells were transiently transfected with FLAG-FKBP12_NLS and either HA-DCAF16 or empty pRK5 vector as a control for 24 hours and then treated with KB02-SLF (1.5 µM, 8 hours). Bar graph represents the quantification of the relative FKBP12 protein content, with DMSO-treated cells set to a value of 1. Data represent mean values±SEM for 3 biological replicates. Statistical significance was calculated with unpaired two-tailed Student's t-tests comparing DMSO- to KB02-SLF-treated samples. P<0.01. FIG. 3D is a Western blot showing a higher molecular weight (HMW) form of HA-DCAF16 is observed in HEK293T cells treated with KB02-SLF (0.4 or 2 µM, 2 h in the presence of 10 µM MG132), and this HMW form, but not the lower molecular weight (LMW) form of HA-DCAF16 co-immunoprecipitated with FLAG-FKBP12_NLS. FIG. 3E is, on the left, a schematic representation of human DCAF16 protein denoting eight cysteines; and on the right, a schematic for identifying KB02-PEG0-SLF modified cysteines on DCAF16. FIG. 3F is a MS/MS spectrum of KB02-PEG0-SLF-modified, triply charged DCAF16 peptide (amino acids 168-184) (SEQ ID NO: 20). The b- and y-ions are shown along with the peptide sequence. FIG. 3G shows the structure of covalent bifunctional protein degrading compound KB02-JQ1. FIG. 3H is a Western blot showing concentration-dependent degradation of endogenous BRD4 in HEK293T cells following treatment with KB02-JQ1 for 24 hours. The bar graph is a quantification of the relative BRD4 level. The BRD4 level from DMSO-treated cells is set to 1. Data represent mean values±SEM for 3 biological replicates. Statistical significance was calculated with unpaired two-tailed Student's t-tests comparing DMSO- to KB02-JQ1-treated samples. P<0.01; P<0.0001. FIG. 3I is a Western blot showing KB02-JQ1-mediated BRD4 degradation is blocked by proteasome inhibitor MG132 and neddylation inhibitor MLN4924. HEK293T cells were preincubated with 10 µM MG132 or 1 µM MLN4924 for 4 hours, followed by 20 hours of treatment with 20 µM KB02-JQ1 and 10 µM MG132 or 1 µM MLN4924. FIG. 3J is a Western blot of FLAG tagged BRD4 co-immunoprecipitated with HA-DCAF16 in the presence of KB02-JQ1. HEK293T cells were co-transfected with BRD4-FLAG and HA-DCAF16 or pRK5 vector for 24 h and treated with 10 µM KB02-JQ1 or DMSO and 10 µM MG132 for 2 hours. FIG. 3K is a Western blot showing degradation of BRD4 in HEK293 DCAF16+/+ (clone 6) and −/− (clone 3 and 4) cells following 24 hours of treatment with 40 µM KB02-JQ1. The bar graph represents quantification of the relative BRD4 protein content, with DMSO-treated cells set to a value of 1. Data represent mean values±SEM for 3 biological replicates. Statistical significance was calculated with unpaired two-tailed Student's t-tests comparing DMSO- to KB02-JQ1-treated samples. *P<0.001.

FIG. 4A is a Western blot after subcellular fractionation of stably expressed FLAG-FKBP12 and FLAG-FKBP12_NLS in HEK293T cells and characterization of a lenalidomide-SLF bifunctional compound as a positive control. FIG. 4B shows the structure of lenalidomide-SLF. FIG. 4C is a Western blot showing the concentration-dependent degradation of stably expressed FLAG-FKBP12 and FLAG-FKBP12_NLS in HEK 293T cells following treatment with lenalidomide-SLF for 4 hours or 24 hours.

FIG. 5A is a Western blot showing time-dependent degradation of FLAG-FKBP12_NLS in HEK293T cells treated with KB02-SLF (2 FIG. 5B shows structures of KB02-PEG0-SLF, KB02-SLF, and KB02-PEG4-SLF and a Western blot of FLAG-FKBP12_NLS following treatment of HEK293T cells with KB02-PEG0-SLF, KB02-SLF, or KB02-PEG4-SLF (0.5-2 µM, 8 hours). FIG. 5C shows structures of SLF, KB02, and KB02-PEG2 and a Western blot of FLAG-FKBP12_NLS in HEK293T cells following treatment of HEK293T cells with KB02, KB02-PEG2, SLF, or the combination of SLF and KB02 or KB02-PEG2 (1.5 μM, 8 hours). FIG. 5D is a Western blot showing that the degradation of FLAG-FKBP12_NLS by KB02-SLF (2 μM, 8 hours) is blocked by excess SLF (25 μM).

FIG. 7A is a picture of a Western blot showing that KB02-SLF degrades FLAG-FKBP12_NLS in MDA-MB-231 cells. MDA-MB-231 cells were treated with 1 μM of KB02-PEG0-SLF, KB02-SLF or KB02-PEG4-SLF for 8 hours. FIG. 7B is a picture of a Western blot showing degradation of stably expressed FLAG-FKBP12_NLS in MDA-MB-231 cells following treatment with KB02-PEG0-SLF, KB02-SLF or KB02-PEG4-SLF (1 μM, 8 hours) is blocked by proteasome inhibitor MG132. FIG. 7C is a picture of a Western blot showing degradation of stably expressed FLAG-FKBP12_NLS in MDA-MB-231 cells following treatment with KB02-PEG0-SLF, KB02-SLF or KB02-PEG4-SLF (1 μM, 8 hours) is blocked by neddylation inhibitor MLN4924. FIG. 7D is a schematic for identifying KB02-SLF-recruited E3 ubiquitin ligases by anti-FLAG affinity enrichment coupled to mass spectrometry (MS)-based proteomics. Light and heavy amino acid-labeled MDA-MB-231 cells stably expressing FLAG-FKBP12_NLS were treated with DMSO or KB02-SLF (10 respectively, for 2 hours in the presence of MG132 (10 Light and heavy cells were then lysed, subject to anti-FLAG immunoprecipitation, and the affinity-enriched proteins combined, digested with trypsin, and analyzed by LC-MS/MS. FIG. 7E is a graph of the SILAC heavy/light (H/L) ratio values of proteins identified in anti-FLAG affinity enrichment experiments (outlined in part d). A high ratio indicates proteins selectively enriched from cells treated with KB02-SLF.

FIG. 8A-FIG. 8D illustrate characterization of KB02-SLF-recruited E3 ubiquitin ligase(s) in HEK293T cells by anti-FLAG affinity enrichment coupled to mass spectrometry (MS)-based proteomics. FIG. 8A is a schematic for a control affinity-enrichment-MS-based proteomics experiment, where light and heavy amino acid-labeled HEK293T cells stably expressing pCDH empty vector were treated for 2 hours with DMSO or KB02-SLF (10 respectively in the presence of 10 μM MG132 (10 Light and heavy cells were then lysed, subject to anti-FLAG immunoprecipitation, and proteins bound to anti-FLAG beads combined, digested with trypsin, and analyzed by LC-MS/MS. FIG. 8B is a chart of the SILAC H/L ratio and spectral count (SC) values for E3 ligase proteins and FKBP12 enriched by anti-FLAG immunoprecipitation from HEK239T cells stably expressing FLAG-FKBP12_NLS, but not enriched from control HEK293T cells expressing empty pCDH vector. FIG. 8C, top, is a Western blot of stably expressed FLAG-FKBP12_NLS in HEK293T cells transiently transduced with shRNAs targeting DTL (shDTL) or a control (shLuc) following treatment with KB02-SLF (2 μM, 8 hours); and, bottom, DTL mRNA was measured by qPCR. Data represent mean values±SEM for 3 biological replicates. FIG. 8D shows shRNA-mediated DCAF16 knockdown attenuated KB02-SLF-dependent polyubiquitination of FLAG-FKBP12_NLS in HEK293T cells stably expressing FLAG-FKBP12_NLS that were transiently transduced with an shRNA targeting DCAF16 (shDCAF16) or a control shRNA (shLuc) and treated with KB02-SLF (5 μM) and MG132 (10 μM) for 2 hours.

FIG. 9A-FIG. 9H illustrate Generation of DCAF16–/– HEK293 cells using CRISPR/Cas 9 and characterization of KB02-SLF-mediated degradation of FLAG-FKBP12_NLS in cells. FIG. 9A shows indel analysis of three DCAF16+/+ clones (clones 6, 17, and 18) and three DCAF16–/– clones (clones 3, 4, and 22) in HEK293 cells. FIG. 9B is a schematic for measuring DCAF16 content in DCAF16+/+ and DCAF16–/– clones by anti-FLAG affinity enrichment coupled to MS-based proteomics of KB02-SLF-treated HEK293 cells stably expressing FLAG-FKBP12_NLS. Light and heavy amino acid-labeled cells from clones shown in the schematic were treated with DMSO or KB02-SLF (10 respectively, for 2 h in the presence of MG132 (10 Light and heavy cells were then lysed, subject to anti-FLAG immunoprecipitation, and the affinity-enriched proteins combined, digested with trypsin, and analyzed by LC-MS/MS. FIG. 9C is a table and a graph showing SILAC heavy/light ratio and spectra count (SC) of DCAF16, DDB1 and FKBP12 content from indicated DCAF16+/+ and DCAF16–/– clones analyzed as described in FIG. 9B. *Note that a maximum H/L value of >10 was assigned to DCAF16 in DCAF16+/+/DCAF16–/– comparisons, which results in a calculated ratio of 7.4 for DCAF16 in the waterfall plot (bottom) showing ratio values for proteins in DCAF16+/+/DCAF16–/– versus DCAF16+/+/DCAF16+/+ comparisons. FIG. 9D through FIG. 9G show concentration-dependent degradation of stably expressed FLAG-FKBP12_NLS in each of the six clones of DCAF16+/+ and DCAF16–/– HEK293 cells treated with KB02-SLF (0.2-5 μM, 8 h). FIG. 9H is a bar graph representing the quantification of the relative HA-DCAF16 content in FIG. 9C, where the HA-DCAF16 level with DMSO-treated cells set to a value of 1. Data represent mean values±SEM for 4 biological replicates (two from DCAF16–/– clone 3, two from DCAF16–/– clone 4). Statistical significance was calculated with unpaired two-tailed Student's t-tests comparing DMSO- to KB02-SLF-treated samples.

FIG. 10A is a Western blot showing KB02-SLF mediates a ternary complex interaction between FLAG-FKBP12_NLS and HA-DCAF16. The higher molecular weight (HMW) form of FLAG-FKBP12_NLS which was co-immunoprecipitated with HA-DCAF16 in the presence of KB02-PEG0-SLF, KB02-SLF or KB02-PEG4-SLF. HEK293T cells stably expressing FLAG-FKBP12_NLS were transfected with HA-DCAF16 for 24 hours and then treated with KB02-PEG0-SLF, KB02-SLF or KB02-PEG4-SLF (5 μM) in the presence of MG132 (10 μM) for 2 hours. FIG. 10B is a picture of a Western blot showing concentration-dependent co-immunoprecipitation of the HMW form of FLAG-FKBP12_NLS with HA-DCAF16 in HEK293T cells treated with KB02-SLF in the presence of MG132 (10 μM) for 2 hours. FIG. 10C-FIG. 10E are pictures of Western blots showing FLAG-FKBP12_NLS co-immunoprecipitated with HA-DCAF16 in the presence of KB02-SLF, but not C-KB02-SLF, KB03-SLF, or KB05-SLF. HEK293T cells stably expressing FLAG-FKBP12_NLS were transfected with HA-DCAF16 for 24 h and the treated with KB02-SLF, C-KB02-SLF, KB03-SLF or KB05-SLF (5 μM) in the presence of MG132

(10 μM) for 2 hours. FIG. 10F is a Western blot showing the higher molecular weight (HMW) form of FLAG-FKBP12_NLS co-immunoprecipitated with HA-DCAF16 in the presence of KB02-SLF. HEK293T cells stably expressing pCDH empty vector or FLAG-FKBP12_NLS were transfected with HA-DCAF16 for 24 hours and then treated with DMSO or KB02-SLF (5 μM) in the presence of MG132 (10 μM) for 2 hours.

FIG. 11A is an MS analysis of KB02-PEG0-SLF-modified cysteine(s) in DCAF16. a, Top: extracted ion chromatograms (EICs) for DCAF16 tryptic peptide (amino acids 168-184) with or without KB02-PEG0-SLF modification. Bottom: MS1 spectra of triply charged DCAF16 tryptic peptide (amino acids 168-184) and KB02-PEG0-SLF-modified, triply charged DCAF16 tryptic peptide (amino acids 168-184). FIG. 11B, Top: extracted ion chromatograms (EICs) for DCAF16 tryptic peptide (amino acids 97-106) with or without the predicted KB02-PEG0-SLF modification. Bottom: MS1 spectrum of triply charged DCAF16 tryptic peptide (amino acids 97-106). FIG. 11C, Top: extracted ion chromatograms (EICs) for DCAF16 tryptic peptide (amino acids 107-133) with or without the predicted KB02-PEG0-SLF modification. Bottom: MS1 spectrum of triply charged DCAF16 tryptic peptide (amino acids 107-133).

FIG. 12A is a picture of a Western blot of FLAG-FKBP12_NLS in DCAF16−/− HEK293 cells expressing WT or C173S, C177S, C178S, or C179S mutants of HA-DCAF16 (or empty pRK5 vector control) following treatment with KB02-SLF (1.5 μM, 8 hours). Bar graph (right) represents quantification of the relative FKBP12 protein content, with DMSO-treated cells set to a value of 1. Data represent mean values±SEM for 3 biological replicates. Statistical significance was calculated with unpaired two-tailed Student's t-tests comparing DMSO- to KB02-SLF-treated samples. *P<0.001. FIG. 12B is a picture of a Western blot of FLAG-FKBP12_NLS in DCAF16−/− HEK293 cells expressing WT or C58S mutant of HA-DCAF16 (or empty pRK5 vector control) following treatment with KB02-SLF (1.5 μM, 8 hours). FIG. 12C is a picture of a Western blot showing KB02-SLF-mediated interaction between the HMW form of WT or mutant HA-DCAF16 and FLAG-FKBP12_NLS as determined by co-immunoprecipitation. The graph to the right represents quantification of the relative HA-DCAF16 protein content, with DMSO-treated cells set to a value of 1. Data represent mean values±SEM for 3 biological replicates. Statistical significance was calculated with unpaired two-tailed Student's t-tests comparing DCAF16 mutant to DCAF16 WT. *P<0.001; ****P<0.0001.

FIG. 14A is a schematic of quantifying the engagement of cysteines in endogenous DCAF16 in cells treated with KB02-SLF (2 μM) or KB02-JQ1 (20 μM) by competitive ABPP performed with tandem-mass tagging (TMT). FIG. 14B is a plot of relative cysteine reactivity (DMSO/KB02-SLF or DMSO/KB02-JQ1) in HEK293T cells treated with DMSO, KB02-SLF (2 μM) or KB02-JQ1 (20 μM) for 1.5 h. The average ratio of each cysteine-containing tryptic peptide was calculated and plotted from 3 biologically independent samples. FIG. 14C represents competitive ABPP results measuring relative reactivity (DMSO/KB02-bifunctional) of C119- and C173/C177-179-containing DCAF16 tryptic peptides from DMSO-, 2 μM KB02-SLF-, or 20 μM KB02-JQ1-treated HEK293T cells, with the peptide signals from DMSO-treated cells set to a value of 1. Data represent mean values±SEM (n=3 biologically independent samples). For the DCAF16 tryptic peptide containing C173 and C177-179 (amino acids 168-184), IA-reactivity was variably assigned to C173 or C177, and these signals were integrated to provide the average engagement data.

DETAILED DESCRIPTION OF THE DISCLOSURE

Figure 1A:
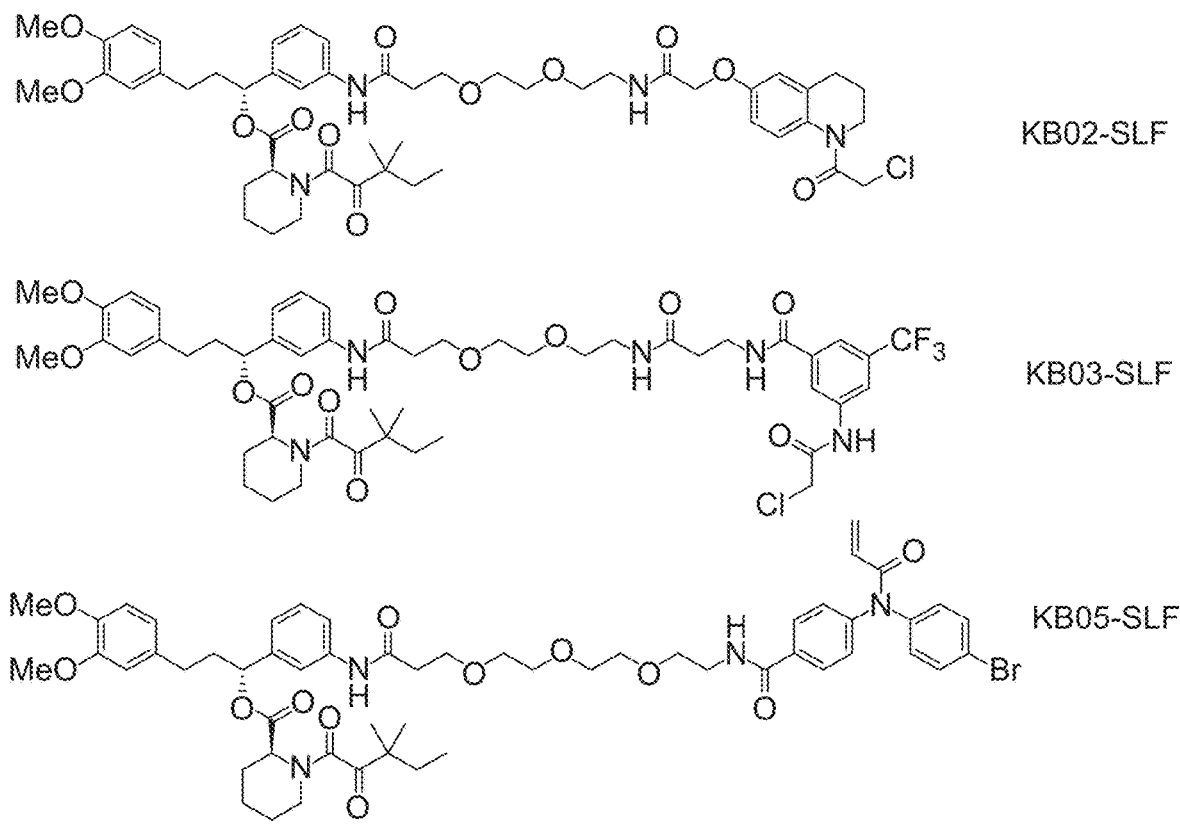

Conventional small-molecule probes and drugs act by directly perturbing the functions of proteins (e.g., blocking enzyme catalysis or antagonizing receptor signaling). Many proteins, however, possess multiple functional domains, and therefore a compound that binds to only one of these domains may fail to fully inactivate the protein (Bondeson, D. P. et al. *Nat Chem Biol* 11, 611-617 (2015) and Winter, G. E. et al. *Science* 348, 1376-1381 (2015)). An alternative strategy uses chemical probes that direct proteins to the proteolytic degradation machinery of the cell, leading to the complete loss of protein expression. This targeted protein degradation approach leverages two types of small molecules—those that form tripartite complexes with specific E3 ubiquitin ligases and neosubstrate proteins (e.g., the IMiD class of therapeutics) and bifunctional compounds, e.g. proteolysis-targeting chimeras, which couple E3 ligase ligands to substrate ligands via a variably structured linker. In some instances, targeted protein degradation acts in a catalytic manner (Bondeson, 2015) that lowers the drug concentrations required to produce a pharmacological effect and operate sub-stoichiometrically to avoid antagonizing the natural functions of the participating E3 ligase. In some cases, only a handful of the 600+ human E3 ligases have been found to support ligand-mediated protein degradation (Buckley, D. L. et al. *Angew Chem Int Ed Engl* 51, 11463-11467 (2012); Ito, T. et al. *Science* 327, 1345-1350 (2010); Vassilev, L. T. et al. *Science* 303, 844-848 (2004)). Each of these E3 ligases has been found to show distinct and restricted substrate specificities (Bondeson, D. P. et al. *Cell Chem Biol* 25, 78-87 e75 (2018); Huang, H. T. et al. *Cell Chem Biol* 25, 88-99 e86 (2018)).

Disclosed herein, in certain embodiments, are compounds for inducing a DDB1- and CUL4-associated factor 16 (DCAF16)-mediated protein degradation. In some instances, also disclosed herein are methods of modulating protein degradation based on a DCAF16-mediated process. In additional instances, disclosed herein are methods of modulating a substrate selectivity of a CUL4-RBX1-DDB1 complex (CRL4) and generation of diverse DCAF16 conjugates for use in said methods.

DDB1- and CUL4-Associated Factor (DCAF) Protein Conjugates

The DDB1- and CUL4-associated factor (DCAF) protein class, also known as DWD (DDB1-binding WD40) and CDW (Cul4-DDB1-associated WD40 repeat), is a group of cofactors which function as substrate receptors in the CUL4-RBX1-DDB1 complex (CRL4), an E3 ligase that falls under the CRL subgroup of the RING finger family. In humans, there are about 90 DCAFs that binds to the DDB1 adaptor, including for example, DDB1- and CUL4-associated factor 16 (DCAF16).

The CRL4 complex comprises the adaptor protein DDB1, which connects the substrate receptor DCAF to the Cullin 4 (CUL4) scaffold. The Cullin 4 scaffold further binds to RBX1. Upon substrate binding, the CUL4-RBX1-DDB1 complex bridges the substrate to the E2-ubiquitin to initiate a direct transfer of ubiquitin molecule onto the substrate.

In some instances, described herein is a DCAF16 conjugate that comprises a DCAF16 protein covalently bound to a synthetic ligand at a cysteine residue. In some instances, the cysteine residue is at a position corresponding to residue 58, 100, 103, 119, 173, 177, 178, or 179 of SEQ ID NO: 1. In some instances, the cysteine residue is at a position corresponding to residue 58, 173, 177, 178, or 179 of SEQ ID NO: 1. In some instances, the cysteine residue is at a position corresponding to residue 173, 177, 178, or 179 of SEQ ID NO: 1. In some instances, the cysteine residue is at a position corresponding to residue 177 or 179 of SEQ ID NO: 1. In some instances, the cysteine residue is at a position corresponding to residue 58, 100, 103, or 119 of SEQ ID NO: 1. In some instances, the cysteine residue is at a position corresponding to residue 100, 103, or 119 of SEQ ID NO: 1. In some instances, the cysteine residue is at a position corresponding to residue 173 or 178 of SEQ ID NO: 1.

In some embodiments, the synthetic ligand is covalently bound to DCAF16 residue C58, C100, C103, C119, C173, C177, C178, or C179 of SEQ ID NO: 1. In some cases, the synthetic ligand is covalently bound to DCAF16 residue C58, C173, C177, C178, or C179 of SEQ ID NO: 1. In some cases, the synthetic ligand is covalently bound to DCAF16 residue C173, C177, C178, or C179 of SEQ ID NO: 1. In some cases, the synthetic ligand is covalently bound to DCAF16 residue C177 or C179 of SEQ ID NO: 1. In some cases, the synthetic ligand is covalently bound to DCAF16 residue C58, C100, C103, or C119 of SEQ ID NO: 1. In some cases, the synthetic ligand is covalently bound to DCAF16 residue C100, C103, or C119 of SEQ ID NO: 1. In some cases, the synthetic ligand is covalently bound to DCAF16 residue C173 or C178 of SEQ ID NO: 1. In some cases, the synthetic ligand is covalently bound to DCAF16 residue C58 of SEQ ID NO: 1. In some cases, the synthetic ligand is covalently bound to DCAF16 residue C100 of SEQ ID NO: 1. In some cases, the synthetic ligand is covalently bound to DCAF16 residue C103 of SEQ ID NO: 1. In some cases, the synthetic ligand is covalently bound to DCAF16 residue C119 of SEQ ID NO: 1. In some cases, the synthetic ligand is covalently bound to DCAF16 residue C173 of SEQ ID NO: 1. In some cases, the synthetic ligand is covalently bound to DCAF16 residue C177 of SEQ ID NO: 1. In some cases, the synthetic ligand is covalently bound to DCAF16 residue C178 of SEQ ID NO: 1.

In some embodiments, the DCAF16 protein comprises a sequence identity that is about 80%, 85%, 90%, 95%, or 99% to SEQ ID NO: 1. In such cases, the synthetic ligand is covalently bound to the DCAF16 protein comprising about 80%, 85%, 90%, 95%, or 99% sequence identity to SEQ ID NO: 1.

In some instances, the synthetic ligand comprises a structure represented by Formula I:

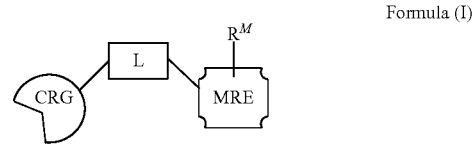

Formula (I)

wherein,
CRG-L is optional, and when present is a covalent reactive group comprising a Michael acceptor moiety, a leaving group moiety, or a moiety capable of forming a covalent bond to the thiol group of a cysteine residue, and L is a linker;
MRE is a molecular recognition element that is capable of interacting with DCAF16; and
$R^M$ is optional, and when present comprises a binding element that binds to a second protein or another compound.

In some instances, MRE is covalently bound to the cysteine residue at a position corresponding to residue 58, 173, 177, 178, or 179 of SEQ ID NO: 1. In some cases, MRE is covalently bound to the cysteine residue at a position corresponding to residue 173, 177, 178, or 179 of SEQ ID NO: 1. In some cases, MRE is covalently bound to the cysteine residue at a position corresponding to residue 177 or 179 of SEQ ID NO: 1. In some cases, MRE is covalently bound to the cysteine residue at a position corresponding to residue 58, 100, 103, or 119 of SEQ ID NO: 1. In some cases, MRE is covalently bound to the cysteine residue at a position corresponding to residue 100, 103, or 119 of SEQ ID NO: 1. In some cases, MRE is covalently bound to the cysteine residue at a position corresponding to residue 173 or 178 of SEQ ID NO: 1.

In some cases, MRE is covalently bound to the cysteine residue of DCAF16 comprising about 80%, 85%, 90%, 95%, or 99% sequence identity to SEQ ID NO: 1.

In some embodiments, described herein are modified DCAF16 proteins comprising a modification at cysteine C173 of SEQ ID NO: 1, wherein the cysteine forms an adduct with a reactive compound. In some embodiments a DCAF16 homolog, active fragment, or variant thereof is modified at a cysteine position equivalent to C173 of SEQ ID NO: 1. In some embodiments, one or more additional residues in DCAF16 forms a non-covalent interaction with a compound described herein. In some instances, the non-covalent interaction is a hydrophobic interaction, charged interaction (e.g., either positively charged or negatively charged interaction), polar interaction, H-bonding, salt bridge, pi-pi stacking, or pi-cation interaction.

In some embodiments, described herein are modified DCAF16 proteins comprising a modification at cysteine C177 of SEQ ID NO: 1, wherein the cysteine forms an adduct with a reactive compound. In some embodiments a DCAF16 homolog, active fragment, or variant thereof is modified at a cysteine position equivalent to C177 of SEQ ID NO: 1. In some embodiments, one or more additional residues in DCAF16 forms a non-covalent interaction with a compound described herein. In some instances, the non-covalent interaction is a hydrophobic interaction, charged interaction (e.g., either positively charged or negatively charged interaction), polar interaction, H-bonding, salt bridge, pi-pi stacking, or pi-cation interaction.

In some embodiments, described herein are modified DCAF16 proteins comprising a modification at cysteine C178 of SEQ ID NO: 1, wherein the cysteine forms an adduct with a reactive compound. In some embodiments a DCAF16 homolog, active fragment, or variant thereof is modified at a cysteine position equivalent to C178 of SEQ ID NO: 1. In some embodiments, one or more additional residues in DCAF16 forms a non-covalent interaction with a compound described herein. In some instances, the non-covalent interaction is a hydrophobic interaction, charged interaction (e.g., either positively charged or negatively charged interaction), polar interaction, H-bonding, salt bridge, pi-pi stacking, or pi-cation interaction.

In some embodiments, described herein are modified DCAF16 proteins comprising a modification at cysteine C179 of SEQ ID NO: 1, wherein the cysteine forms an adduct with a reactive compound. In some embodiments a DCAF16 homolog, active fragment, or variant thereof is modified at a cysteine position equivalent to C179 of SEQ ID NO: 1. In some embodiments, one or more additional residues in DCAF16 forms a non-covalent interaction with a compound described herein. In some instances, the non-covalent interaction is a hydrophobic interaction, charged interaction (e.g., either positively charged or negatively charged interaction), polar interaction, H-bonding, salt bridge, pi-pi stacking, or pi-cation interaction.

In some embodiments, described herein is a heterobifunctional degrader comprising a DCAF16 protein binding moiety, a linker, and a target protein binding moiety. In some embodiments the heterobifunctional degrader modifies DCAF16 protein at cysteine C173 of SEQ ID NO: 1 or corresponding cysteine of a cereblon homolog, active fragment, or variant thereof, wherein the cysteine forms an adduct with a reactive compound. In some embodiments, one or more additional residues in DCAF16 forms a non-covalent interaction with a compound described herein. In some instances, the non-covalent interaction is a hydrophobic interaction, charged interaction (e.g., either positively charged or negatively charged interaction), polar interaction, H-bonding, salt bridge, pi-pi stacking, or pi-cation interaction.

In some cases, the Michael acceptor moiety comprises an alkene or an alkyne moiety. In some cases, the Michael acceptor moiety comprises an alkene moiety.

In some cases, the Michael acceptor moiety comprises an alkene moiety. In some cases, the Michael acceptor moiety is —CH═CH—. In some cases, the Michael acceptor moiety comprises an alkyne moiety. In some cases, the Michael acceptor moiety is —C≡C—. In some cases, the leaving group moiety is an alpha chloride. In some case, the leaving group moiety is —C(═O)CH$_2$Cl. In some cases, the Michael acceptor moiety comprises an alkyne moiety.

In some cases, MRE comprises a small molecule compound, a polynucleotide, a polypeptide or fragments thereof, or a peptidomimetic. In some embodiments, MRE is a small molecule compound. In some embodiments, MRE is a polynucleotide. In some embodiments, MRE is a polypeptide or fragments thereof. In some embodiments, MRE is a peptidomimetic.

In some embodiments, the synthetic ligand has a structure represented by Formula (IIA) or Formula (IIB):

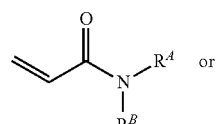

Formula (IIA)

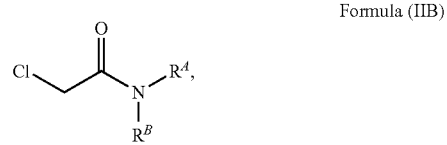

Formula (IIB)

wherein,
each $R^A$ and $R^B$ is independently selected from the group consisting of H, D, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_8$cycloalkyl, substituted or unsubstituted $C_2$-$C_7$heterocycloalkyl, substituted or unsubstituted aryl, substituted or unsubstituted $C_1$-$C_3$alkylene-aryl, substituted or unsubstituted heteroaryl, and substituted or unsubstituted $C_1$-$C_3$alkylene-heteroaryl; or $R^A$ and $R^B$ together with the nitrogen to which they are attached form a substituted or unsubstituted 5, 6, 7 or 8-membered heterocyclic ring A, optionally having one additional heteroatom moiety independently selected from $NR^1$, O, or S; and $R^1$ is H, D, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted aryl, or substituted or unsubstituted heteroaryl.

In some embodiments, $R^A$ is H or D.

In some embodiments, $R^B$ is substituted or unsubstituted aryl or substituted or unsubstituted heteroaryl. In some embodiments, $R^B$ is substituted or unsubstituted aryl. In some embodiments, $R^B$ is substituted or unsubstituted heteroaryl.

In some embodiments, $R^B$ is substituted aryl. In some embodiments, $R^B$ is aryl, substituted with one or more substituents selected from the group consisting of halogen, $C_1$-$C_4$fluoroalkyl, —CN, and —NO$_2$.

In some embodiments, $R^A$ and $R^B$ together with the nitrogen to which they are attached form a substituted or unsubstituted 6 or 7-membered heterocyclic ring A. In some embodiments, ring A is a 6-membered heterocyclic ring. In some embodiments, ring A is 6-membered heterocyclic ring substituted with substituted or unsubstituted aryl or substituted or unsubstituted heteroaryl. In some embodiments, ring A is 6-membered heterocyclic ring fused with substituted or unsubstituted aryl or substituted or unsubstituted heteroaryl.

In some embodiments, the synthetic ligand has a structure represented by Formula (III):

Formula (III)

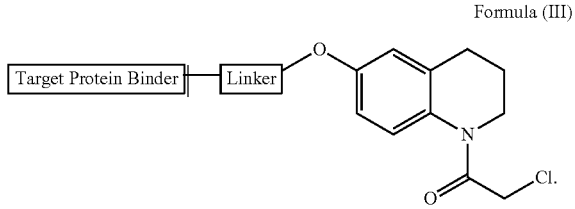 [SMILES: COc1ccc2c(c1)CCCN2C(=O)CCl]

In some instances, the chloroacetamide-based binder conjugate to DCAF16 at a cysteine residue at a position corresponding to residue 58, 173, 177, 178, or 179 of SEQ ID NO: 1. In some cases, the chloroacetamide-based binder conjugate to DCAF16 at a cysteine residue at a position corresponding to residue 173, 177, 178, or 179 of SEQ ID NO: 1. In some cases, the chloroacetamide-based binder conjugate to DCAF16 at a cysteine residue at a position corresponding to residue 177 or 179 of SEQ ID NO: 1. In some cases, the chloroacetamide-based binder conjugate to DCAF16 at a cysteine residue at a position corresponding to residue 58, 100, 103, or 119 of SEQ ID NO: 1. In some cases, the chloroacetamide-based binder conjugate to DCAF16 at a cysteine residue at a position corresponding to residue 100, 103, or 119 of SEQ ID NO: 1. In some cases, the chloroacetamide-based binder conjugate to DCAF16 at a cysteine residue at a position corresponding to residue 173 or 178 of SEQ ID NO: 1.

In some instances, the synthetic ligand is

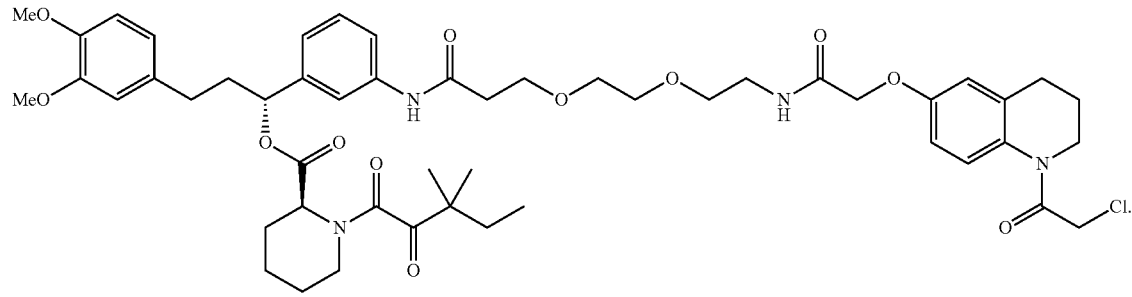 [SMILES: CCC(C)(C)C(=O)C(=O)N1CCCC[C@H]1C(=O)O[C@H](CCc1ccc(OC)c(OC)c1)c1cccc(NC(=O)CCOCCOCCNC(=O)COc2ccc3c(c2)CCCN3C(=O)CCl)c1]

ing ethylene oxide units. In some instances, a dPEG comprises about 13 or more repeating ethylene oxide units. In some instances, a dPEG comprises about 14 or more repeating ethylene oxide units. In some instances, a dPEG comprises about 15 or more repeating ethylene oxide units. In some instances, a dPEG comprises about 16 or more repeating ethylene oxide units. In some instances, a dPEG comprises about 17 or more repeating ethylene oxide units. In some instances, a dPEG comprises about 18 or more repeating ethylene oxide units. In some instances, a dPEG comprises about 19 or more repeating ethylene oxide units. In some instances, a dPEG comprises about 20 or more repeating ethylene oxide units. In some instances, a dPEG comprises about 22 or more repeating ethylene oxide units. In some instances, a dPEG comprises about 24 or more repeating ethylene oxide units. In some instances, a dPEG comprises about 26 or more repeating ethylene oxide units. In some instances, a dPEG comprises about 28 or more repeating ethylene oxide units. In some instances, a dPEG comprises about 30 or more repeating ethylene oxide units. In some instances, a dPEG comprises about 35 or more repeating ethylene oxide units. In some instances, a dPEG comprises about 40 or more repeating ethylene oxide units. In some instances, a dPEG comprises about 42 or more repeating ethylene oxide units. In some instances, a dPEG comprises about 48 or more repeating ethylene oxide units. In some instances, a dPEG comprises about 50 or more repeating ethylene oxide units. In some cases, a dPEG is synthesized as a single molecular weight compound from pure (e.g., about 95%, 98%, 99%, or 99.5%) staring material in a step-wise fashion. In some cases, a dPEG has a specific molecular weight, rather than an average molecular weight. In some cases, a dPEG described herein is a dPEG from Quanta Biodesign, LIVID.

In some instances, L is an alkyl group, e.g., a $C_1$-$C_{10}$ alkyl group (e.g., a $C_9$, $C_8$, $C_7$, $C_6$, $C_5$, $C_4$, $C_3$, $C_2$, or $C_1$ alkyl group).

In some instances, L is a homobifunctional cross linker. Exemplary homobifunctional linkers include, but are not limited to, Lomant's reagent dithiobis (succinimidylpropionate) DSP, 3'3'-dithiobis(sulfosuccinimidyl proprionate (DTSSP), disuccinimidyl suberate (DSS), bis(sulfosuccinimidyl)suberate (BS), disuccinimidyl tartrate (DST), di sulfosuccinimidyl tartrate (sulfo DST), ethylene glycobis (succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitroben-

Linkers

In some embodiments, L is a linker capable of positioning a neosubstrate (e.g., a substrate that is not the native substrate of a CUL4-RBX1-DDB1 complex described above) to be ubiquitinated by the E2 enzyme. In some instances, L is a cleavable linker. In other instances, L is a non-cleavable linker. In additional instances, L is a polymeric linker (e.g., a water-soluble polymeric linker).

In some cases, L is a polyethylene glycol (PEG) molecule. In some instances, the PEG molecule is a discrete PEG, in which the discrete PEG is a polymeric PEG comprising more than one repeating ethylene oxide units. In some instances, a discrete PEG (dPEG) comprises from 2 to 60, from 2 to 50, or from 2 to 48 repeating ethylene oxide units. In some instances, a dPEG comprises about 2, 3, 4, 5, 6, 7, 8, 9, 10, 11, 12, 13, 14, 15, 16, 17, 18, 19, 20, 22, 24, 26, 28, 30, 35, 40, 42, 48, 50 or more repeating ethylene oxide units. In some instances, a dPEG comprises about 2 or more repeating ethylene oxide units. In some instances, a dPEG comprises about 3 or more repeating ethylene oxide units. In some instances, a dPEG comprises about 4 or more repeating ethylene oxide units. In some instances, a dPEG comprises about 5 or more repeating ethylene oxide units. In some instances, a dPEG comprises about 6 or more repeating ethylene oxide units. In some instances, a dPEG comprises about 7 or more repeating ethylene oxide units. In some instances, a dPEG comprises about 8 or more repeating ethylene oxide units. In some instances, a dPEG comprises about 9 or more repeating ethylene oxide units. In some instances, a dPEG comprises about 10 or more repeating ethylene oxide units. In some instances, a dPEG comprises about 11 or more repeating ethylene oxide units. In some instances, a dPEG comprises about 12 or more repeatzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide).

In some instances, L is a heterobifunctional cross linker. Exemplary heterobifunctional linker include, but are not limited to, amine-reactive and sulfhydryl cross-linkers such as N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MB s), N-succinimidyl(4-iodoacteyl)aminobenzoate (sIAB), sulfo-succinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMB s), N-(γ-maleimidobutyryloxy)sulfosuccinimide ester (sulfo-GMBs), succinimidyl 6-((iodoacetyl)amino) hexanoate (sIAX), succinimidyl 6-[6-(((iodoacetyl)amino) hexanoyl)amino]hexanoate (sIAXX), succinimidyl 4-(((iodoacetyl)amino)methyl)cyclohexane-1-carboxylate (sIAC), succinimidyl 6-((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 ($M_2C_2H$), 3-(2-pyridyldithio)propionyl hydrazide (PDPH), amine-reactive and photoreactive cross-linkers such as N-hydroxy succinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido)hexanoate (sulfo-NHs-LC-AsA), sulfosuccinimidyl-2-(p-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)$_{1,3}$'-dithiopropionate (sADP), N-sulfosuccinimidyl(4-azidophenyl)-1,3'-dithiopropionate (sulfo-sADP), sulfosuccinimidyl 4-(p-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), p-nitrophenyl diazopyruvate (pNPDP), p-nitrophenyl-2-diazo-3,3,3-trifluoropropionate (PNP-DTP), sulfhydryl-reactive and photoreactive cross-linkers such as 1-(p-Azidosalicylamido)-4-(iodoacetamido) butane (AsIB), N-[4-(p-azidosalicylamido)butyl]-3'-(2'-pyridyldithio)propionamide (APDP), benzophenone-4-iodoacetamide, benzophenone-4-maleimide carbonyl-reactive and photoreactive cross-linkers such as p-azidobenzoyl hydrazide (ABH), carboxylate-reactive and photoreactive cross-linkers such as 4-(p-azidosalicylamido) butylamine (AsBA), and arginine-reactive and photoreactive cross-linkers such as p-azidophenyl glyoxal (APG).

In some embodiments, L is a peptide linker. In some cases, the peptide linker comprises at least 2, 3, 4, 5, or 6 more amino acid residues. In some instances, the peptide linker comprises at most 2, 3, 4, 5, 6, 7, or 8 amino acid residues. In some instances, the peptide linker comprises about 2, about 3, about 4, about 5, or about 6 amino acid residues. In some instances, the peptide linker is a cleavable peptide linker (e.g., either enzymatically or chemically). In some instances, the peptide linker is a non-cleavable peptide moiety. In some instances, the peptide linker comprises Val-Cit (valine-citrulline), Gly-Gly-Phe-Gly (SEQ ID NO: 2), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 3), or Gly-Phe-Leu-Gly (SEQ ID NO: 4).

Further Forms of Compounds

In one aspect, the compound of Formula (I), Formula (IIA), Formula (IIB), or Formula (III) possesses one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In one aspect, stereoisomers are obtained by stereoselective synthesis.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine and chlorine, such as, for example, $^2H$, $^3H$, $^{13}C$, $^{14}C$, $^{15}N$, $^{18}O$, $^{17}O$, $^{35}S$, $^{36}Cl$. In one aspect, isotopically-labeled compounds described herein, for example those into which radioactive isotopes such as $^3H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

Compounds described herein may be formed as, and/or used as, acceptable salts. The type of acceptable salts, include, but are not limited to: (1) acid addition salts, formed by reacting the free base form of the compound with an acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris (hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms, particularly solvates. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Synthesis of Compounds

In some embodiments, the synthesis of compounds described herein is accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, Fisher Scientific (Fisher Chemicals), and Acros Organics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4$^{th}$ Ed., Vols. A and B (Plenum 2000, 2001), and Green and Wuts, Protective Groups in Organic Synthesis 3$^{rd}$ Ed., (Wiley 1999) (all of which are incorporated by reference for such disclosure). General methods for the preparation of compounds as disclosed herein may be derived from reactions and the reactions may be modified by the use of appropriate reagents and conditions, for the introduction of the various moieties found in the formulae as provided herein. As a guide the following synthetic methods may be utilized.

In the reactions described, it may be necessary to protect reactive functional groups, for example hydroxy, amino, imino, thio or carboxy groups, where these are desired in the final product, in order to avoid their unwanted participation in reactions. A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Methods of Use

In certain embodiments, described herein are methods of degrading a target protein using the compounds disclosed herein. In certain embodiments, described herein are methods of degrading a target nuclear protein using the compounds disclosed herein. In some instances, a compound of Formula (I), Formula (IIA), Formula (IIB), or Formula (III) is utilized to modulate the degradation of a target protein (e.g., a nuclear protein).

In some embodiments, described herein are methods of degrading ACAT1 using the compounds disclosed herein. In some embodiments, described herein are methods of degrading a nuclear localized protein using the compound disclosed herein. In some embodiments, the target protein comprises a structural protein, a receptor, an enzyme, a cell surface protein, a protein pertinent to the integrated function of a cell, including a protein involved in catalytic activity, aromatase activity, motor activity, helicase activity, metabolic processes (anabolism and catabolism), antioxidant activity, proteolysis, biosynthesis, a protein with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, a behavioral protein, a cell adhesion protein, a protein involved in cell death, a protein involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, or translation regulator activity.

In some embodiments, the target protein comprises a protein from a eukaryote or a prokaryote, including a microbe, virus, fungus, or parasite.

In some embodiments, exemplary target proteins include, but are not limited to, BRD4, ERRa, AR, RIPK2, B7.1 and B7, TINFR1m, TNFR2, NADPH oxidase, Bc1IBax and other partners in the apoptosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, newokinins and receptors, inosine monophosphate dehydrogenase, p38 MAP Kinase, Ras-Raf-MEK-ERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels.

Proteins of interest can include proteins from eukaryotes and prokaryotes including humans as targets for drug therapy, other animals, including domesticated animals, microbials for the determination of targets for antibiotics and other antimicrobials and plants, and even viruses, among numerous others. Accordingly, the target protein binding moiety of a hetero-bifunctional degrader may be any peptide or small molecule that bind protein targets such as FoxO1, HDAC, DP-1, E2F, ABL, AMPK, BRK, BRSK I, BRSK2, BTK, CAMKK1, CAMKK alpha, CAMKK beta, Rb, Suv39HI, SCF, pl9INK4D, GSK-3, pi 8 INK4, myc, cyclin E, CDK2, CDK9, CDG4/6, Cycline D, p16 INK4A, cdc25A, BMI1, Akt, CHK1/2, C 1 delta, CK1 gamma, C 2, CLK2, CSK, DDR2, DYRK1 A/2/3, EF2K, EPH-A2/A4/B1/B2/B3/B4, EIF2A 3, Smad2, Smad3, Smad4, Smad7, p53, p21 Cipl, PAX, Fyn, CAS, $C_3G$, SOS, Tal, Raptor, RACK-1, CRK, Rap1, Rac, KRas, NRas, HRas, GRB2, FAK, PI3K, spred, Spry, mTOR, MPK, LKB1, PAK 1/2/4/5/6, PDGFRA, PYK2, Src, SRPK1, PLC, PKC, PKA, PKB alpha/beta, PKC alpha/gamma/zeta, PKD, PLK1, PRAK, PRK2, WAVE-2, TSC2, DAPK1, BAD, IMP, C-TAK1, TAK1, TAO1, TBK1, TESK1, TGFBR1, TIE2, TLK1, TrkA, TSSK1, TTBK1/2, TTK, Tp12/cot1, MEK1, MEK2, PLDL Erk1, Erk2, Erk5, Erk8, p9ORSK, PEA-15, SRF, p27 KIP1, TIF 1a, HMGN1, ER81, MKP-3, c-Fos, FGF-R1, GCK, GSK3 beta, HER4, HIPK1/2/3/, IGF-1R, cdc25, UBF, LAMTOR2, Statl, StaO, CREB, JAK, PTEN, NF-kappaB, HECTH9, Bax, HSP70, HSP90, Apaf-1, Cyto c, BCL-2, Bcl-xL, Smac, XIAP, Caspase-9, Caspase-3, Caspase-6, Caspase-7, CDC37, TAB, IKK, TRADD, TRAF2, R1P1, FLIP, JNK1/2/3, Lck, A-Raf, B-Raf, C-Raf, MOS, MLK1/3, MN 1/2, MSK1, MST2/3/4, MPSK1, MEKK1, ME K4, MEL, ASK1, MINK1, MKK 1/2/3/4L5/7, NE 2a/6/7, NUAK1, OSR1, SAP, STK33, Syk, Lyn, PDK1, PHK, PIM 1/2/3, Ataxin-1, mTORC1, MDM2, p21 Waf1, Cyclin Dl, Lamin A, Tp12, Myc, catenin, Wnt, IKK-beta, IKK-gamma, IKK-alpha, IKK-epsilon, ELK, p65RelA, IRAKI, IRA 2, IRAK4, IRR, FADD, TRAF6, TRAF3, MKK3, MKK6, ROCK2, RSK1/2, SGK 1, SmMLCK, SIK2/3, ULK1/2, VEGFR1, WNK 1, YES1, ZAP70, MAP4K3, MAP4K5, MAPK1b, MAPKAP-K2 K3, p38 alpha/beta/delta/gamma MAPK, Aurora A, Aurora B, Aurora C, MCAK, Clip, MAPKAPK, MARK 1/2/3/4, Mud, SHC, CXCR4, Gap-1, beta-catenin/TCF, Cbl, BRM, Mc1-1, BRD2, BRD3, BRD4, AR, RAS, ErbB3, EGFR, IRE1, HPK1, RIPK2, and ERa, including variants, mutations, splice variants, indels and fusions of these target proteins listed. Other examples of protein targets include Ras proteins, P13K, Ral-GDS, H-Ras, N-Ras, KRas4A, K-Ras4B, BRG1, RAF, BRAF, CRAF, and BET. In one embodiment, the protein target is selected from the group consisting of EGFR, RAS, BRM, BRG1, MDM2, RAF (BRAF and CRAF), BET, and USP7.

A number of drug targets for human therapeutics also represent protein targets to which a protein binding moiety may be bound and incorporated into compounds according to the present disclosure. These include proteins which may be used to restore function in numerous polygenic diseases, including for example B7.1 and B7, TINFR1m, TNFR2, NADPH oxidase, Bc1IBax and other partners in the apotosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-αR, ICAM1, Cat+ channels, VC AM, VLA-4 integrin, selectins, CD40/CD40L, newokinins and receptors, inosine monophosphate dehydrogenase, p38 MAP Kinase, Ras1Raf1MEWERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), famesyltransferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further target proteins include Acetyl-CoA carboxylase, adenylosuccinate synthetase, protoporphyrinogen oxidase, and enolpyruvylshikimate-phosphate synthase.

In some embodiments, the target protein is a protein that is upregulated (e.g., overexpressed) in a disease or condition. In some instances, the disease or condition is a cancer, e.g., a solid tumor or a hematologic malignancy such as a Hodgkin's lymphoma or a non-Hodgkin's lymphoma. In some cases, the cancer is breast cancer, brain cancer, colorectal cancer, esophagus cancer, head and neck cancer, kidney cancer, lung cancer, ovarian cancer, prostate cancer, or stomach cancer. In some cases, the cancer is chronic lymphocytic leukemia, small lymphocytic lymphoma, Burkitts lymphoma, diffuse large B-cell lymphoma, follicular lymphoma, mantle cell lymphoma, or Waldenstrom's macrglobulinemia.

In other instances, the disease or condition is an autoimmune disease. In some cases, the autoimmune disease is multiple sclerosis, Alzheimer's disease, inflammatory bowel disease, Lou Gehrig's disease, diabetes, psoriasis, rheumatoid arthritis, or graft-versus-host disease.

In some embodiments, described herein are methods of modulating substrate selectivity of a CUL4-RBX1-DDB1 complex (CRL4). In some instances, the method comprises contacting CRL4 comprising a DCAF16 protein with a synthetic ligand for a time sufficient for the ligand to interact with a cysteine residue of the DCAF16 protein to form a CRL4-ligand complex, thereby modulating substrate selectivity of the CRL4 complex; wherein the synthetic ligand comprises a DCAF16-interacting portion linked to a substrate binding portion.

In some instances, the cysteine residue is at a position corresponding to residue 58, 100, 103, 119, 173, 177, 178, or 179 of SEQ ID NO: 1. In some cases, the cysteine residue is at a position corresponding to residue 58, 173, 177, 178, or 179 of SEQ ID NO: 1. In some cases, the cysteine residue is at a position corresponding to residue 173, 177, 178, or 179 of SEQ ID NO: 1. In some cases, the cysteine residue is at a position corresponding to residue 177 or 179 of SEQ ID NO: 1. In some cases, the cysteine residue is at a position corresponding to residue 58, 100, 103, or 119 of SEQ ID NO: 1. In some cases, the cysteine residue is at a position corresponding to residue 100, 103, or 119 of SEQ ID NO: 1. In some cases, the cysteine residue is at a position corresponding to residue 173 or 178 of SEQ ID NO: 1.

In some instances, the synthetic ligand comprises a structure represented by Formula I:

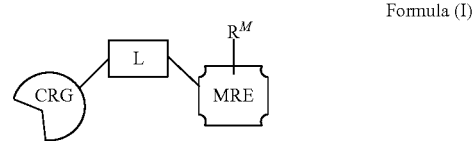

Formula (I)

wherein,

CRG-L is optional, and when present is a covalent reactive group comprising a Michael acceptor moiety, a leaving group moiety, or a moiety capable of forming a covalent bond to the thiol group of a cysteine residue, and L is a linker;

MRE is a molecular recognition element that is capable of interacting with DCAF16; and $R^M$ is optional, and when present comprises a binding element that binds to a second protein or another compound.

In some instances, the MRE is covalently bound to the cysteine residue at a position corresponding to residue 58, 100, 103, 119, 173, 177, 178, or 179 of SEQ ID NO: 1. In some cases, the MRE is covalently bound to the cysteine residue at a position corresponding to residue 58, 173, 177, 178, or 179 of SEQ ID NO: 1. In some cases, the MRE is covalently bound to the cysteine residue at a position corresponding to residue 173, 177, 178, or 179 of SEQ ID NO: 1. In some cases, the MRE is covalently bound to the cysteine residue at a position corresponding to residue 177 or 179 of SEQ ID NO: 1. In some cases, the MRE is covalently bound to the cysteine residue at a position corresponding to residue 58, 100, 103, or 119 of SEQ ID NO: 1. In some cases, the MRE is covalently bound to the cysteine residue at a position corresponding to residue 100, 103, or 119 of SEQ ID NO: 1. In some cases, the MRE is covalently bound to the cysteine residue at a position corresponding to residue 173 or 178 of SEQ ID NO: 1.

In some instances, the Michael acceptor moiety comprises an alkene or an alkyne moiety.

In some instances, L is a cleavable linker.

In other instances, L is a non-cleavable linker.

In additional instances, L is a polymeric linker. In some cases, L is a polyethylene glycol (PEG) molecule.

In some cases, MRE comprises a small molecule compound, a polynucleotide, a polypeptide or fragments thereof, or a peptidomimetic.

In some instances, the synthetic ligand has a structure represented by Formula (IIA) or Formula (IIB):

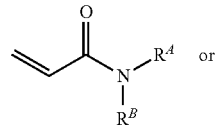

Formula (IIA)

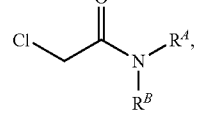

Formula (IIB)

wherein,
each $R^A$ and $R^B$ is independently selected from the group consisting of H, D, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_8$cycloalkyl, substituted or unsubstituted $C_2$-$C_7$heterocycloalkyl, substituted or unsubstituted aryl, substituted or unsubstituted $C_1$-$C_3$ alkylene-aryl, substituted or unsubstituted heteroaryl, and substituted or unsubstituted $C_1$-$C_3$ alkylene-heteroaryl;

or $R^A$ and $R^B$ together with the nitrogen to which they are attached form a 5, 6, 7 or 8-membered heterocyclic ring A, optionally having one additional heteroatom moiety independently selected from $NR^1$, O, or S; wherein A is optionally substituted; and $R^1$ is H, D, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted aryl, or substituted or unsubstituted heteroaryl.

In some instances, the synthetic ligand has a structure represented by Formula (III):

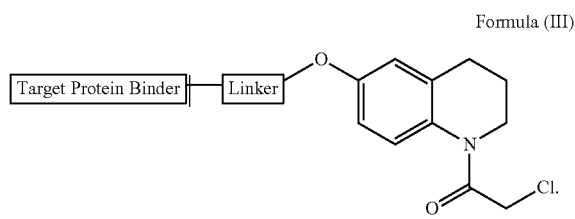 [SMILES: COc1ccc2c(c1)CCCN2C(=O)CCl]

Formula (III)

In some cases, the synthetic ligand is

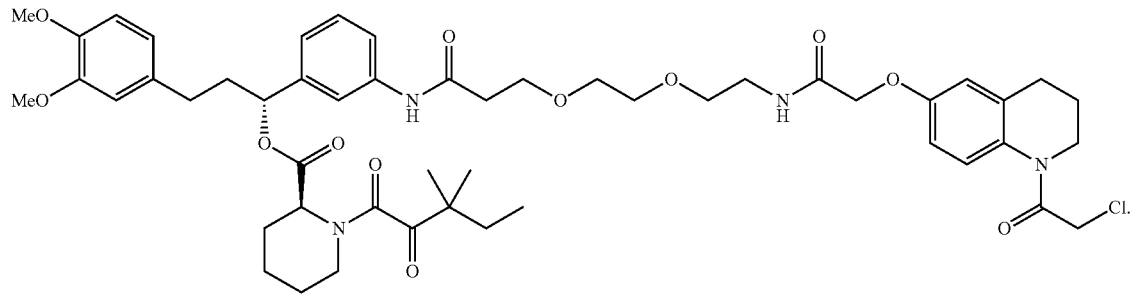 [SMILES: CCC(C)(C)C(=O)C(=O)N1CCCC[C@H]1C(=O)O[C@H](CCc1ccc(OC)c(OC)c1)c1cccc(NC(=O)CCOCCOCCNC(=O)COc2ccc3c(c2)CCCN3C(=O)CCl)c1]

In some cases, the method is an in vitro method.
In other cases, the method is an in vivo method.
In some cases, the cell is from a subject having a cancer.
In some cases, the subject is a human.

Cells, Analytical Techniques, and Instrumentation

In some instances, the methods comprising profiling a cell sample or a cell lysate from a DCAF16-expressing cell. In some embodiments, the cell is obtained from an animal. In some instances, the animal cell includes a cell from a marine invertebrate, fish, insects, amphibian, reptile, or mammal. In some instances, the mammalian cell is a primate, ape, equine, bovine, porcine, canine, or feline. In some instances, the mammalian cell is a primate, ape, equine, bovine, porcine, canine, feline, or rodent. In some instances, the mammal is a primate, ape, dog, cat, rabbit, ferret, or the like. In some cases, the rodent expresses DCAF16 through genetic engineering, e.g. CRISPR.

In some embodiments, the DCAF16 cell sample or cell lysate sample is obtained from a mammalian cell. In some instances, the mammalian cell is an epithelial cell, connective tissue cell, hormone secreting cell, a nerve cell, a skeletal muscle cell, a blood cell, or an immune system cell.

Exemplary mammalian cells include, but are not limited to, 293A cell line, 293FT cell line, 293F cells, 293 H cells, HEK 293 cells, CHO DG44 cells, CHO—S cells, CHO-K1 cells, Expi293F™ cells, Flp-In™ T-REx™ 293 cell line, Flp-In™-293 cell line, Flp-In™-3T3 cell line, Flp-In™-BHK cell line, Flp-In™—CHO cell line, Flp-In™-CV-1 cell line, Flp-In™-Jurkat cell line, FreeStyle™ 293-F cells, FreeStyle™ CHO—S cells, GripTite™ 293 MSR cell line, GS-CHO cell line, HepaRG™ cells, T-REx™ Jurkat cell line, Per.C6 cells, T-REx™-293 cell line, T-REx™—CHO cell line, T-REx™-HeLa cell line, NC-HIMT cell line, and PC12 cell line.

In some instances, the DCAF16 cell sample or cell lysate sample is obtained from cells of a tumor cell line. In some instances, the cell sample or cell lysate sample is obtained from cells of a solid tumor cell line. In some instances, the solid tumor cell line is a sarcoma cell line. In some instances, the solid tumor cell line is a carcinoma cell line. In some embodiments, the sarcoma cell line is obtained from a cell line of alveolar rhabdomyosarcoma, alveolar soft part sarcoma, ameloblastoma, angiosarcoma, chondrosarcoma, chordoma, clear cell sarcoma of soft tissue, dedifferentiated liposarcoma, desmoid, desmoplastic small round cell tumor, embryonal rhabdomyosarcoma, epithelioid fibrosarcoma, epithelioid hemangioendothelioma, epithelioid sarcoma, esthesioneuroblastoma, Ewing sarcoma, extrarenal rhabdoid tumor, extraskeletal myxoid chondrosarcoma, extraskeletal osteosarcoma, fibrosarcoma, giant cell tumor, hemangiopericytoma, infantile fibrosarcoma, inflammatory myofibroblastic tumor, Kaposi sarcoma, leiomyosarcoma of bone, liposarcoma, liposarcoma of bone, malignant fibrous histiocytoma (MFH), malignant fibrous histiocytoma (MFH) of bone, malignant mesenchymoma, malignant peripheral nerve sheath tumor, mesenchymal chondrosarcoma, myxofibrosarcoma, myxoid liposarcoma, myxoinflammatory fibroblastic sarcoma, neoplasms with perivascular epitheioid cell differentiation, osteosarcoma, parosteal osteosarcoma, neoplasm with perivascular epitheioid cell differentiation, periosteal osteosarcoma, pleomorphic liposarcoma, pleomorphic rhabdomyosarcoma, PNET/extraskeletal Ewing tumor, rhabdomyosarcoma, round cell liposarcoma, small cell osteosarcoma, solitary fibrous tumor, synovial sarcoma, telangiectatic osteosarcoma.

In some embodiments, the carcinoma cell line is obtained from a cell line of adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, or vulvar cancer.

In some instances, the DCAF16 cell sample or cell lysate sample is obtained from cells of a hematologic malignant cell line. In some instances, the hematologic malignant cell line is a T-cell cell line. In some instances, B-cell cell line. In some instances, the hematologic malignant cell line is obtained from a T-cell cell line of: peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas.

In some instances, the hematologic malignant cell line is obtained from a B-cell cell line of: acute lymphoblastic leukemia (ALL), acute myelogenous leukemia (AML), chronic myelogenous leukemia (CML), acute monocytic leukemia (AMoL), chronic lymphocytic leukemia (CLL), high-risk chronic lymphocytic leukemia (CLL), small lymphocytic lymphoma (SLL), high-risk small lymphocytic lymphoma (SLL), follicular lymphoma (FL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some embodiments, the DCAF16 cell sample or cell lysate sample is obtained from a tumor cell line. Exemplary tumor cell line includes, but is not limited to, 600MPE, AU565, BT-20, BT-474, BT-483, BT-549, Evsa-T, Hs578T, MCF-7, MDA-MB-231, SkBr3, T-47D, HeLa, DU145, PC3, LNCaP, A549, H1299, NCI-H460, A2780, SKOV-3/Luc, Neuro2a, RKO, RKO-AS45-1, HT-29, SW1417, SW948, DLD-1, SW480, Capan-1, MC/9, B72.3, B25.2, B6.2, B38.1, DMS 153, SU.86.86, SNU-182, SNU-423, SNU-449, SNU-475, SNU-387, Hs 817.T, LMH, LMH/2A, SNU-398, PLHC-1, HepG2/SF, OCI-Ly1, OCI-Ly2, OCI-Ly3, OCI-Ly4, OCI-Ly6, OCI-Ly7, OCI-Ly10, OCI-Ly18, OCI-Ly19, U2932, DB, HBL-1, RIVA, SUDHL2, TMD8, MEC1, MEC2, 8E5, CCRF-CEM, MOLT-3, TALL-104, AML-193, THP-1, BDCM, HL-60, Jurkat, RPMI 8226, MOLT-4, RS4, K-562, KASUMI-1, Daudi, GA-10, Raji, JeKo-1, NK-92, and Mino.

In some embodiments, the DCAF16 cell sample or cell lysate sample is from any tissue or fluid from an individual. Samples include, but are not limited to, tissue (e.g. connective tissue, muscle tissue, nervous tissue, or epithelial tissue), whole blood, dissociated bone marrow, bone marrow aspirate, pleural fluid, peritoneal fluid, central spinal fluid, abdominal fluid, pancreatic fluid, cerebrospinal fluid, brain fluid, ascites, pericardial fluid, urine, saliva, bronchial lavage, sweat, tears, ear flow, sputum, hydrocele fluid, semen, vaginal flow, milk, amniotic fluid, and secretions of respiratory, intestinal or genitourinary tract. In some embodiments, the cell sample or cell lysate sample is a tissue sample, such as a sample obtained from a biopsy or a tumor tissue sample. In some embodiments, the cell sample or cell lysate sample is a blood serum sample. In some embodiments, the cell sample or cell lysate sample is a blood cell sample containing one or more peripheral blood mononuclear cells (PBMCs). In some embodiments, the cell sample or cell lysate sample contains one or more circulating tumor cells (CTCs). In some embodiments, the cell sample or cell lysate sample contains one or more disseminated tumor cells (DTC, e.g., in a bone marrow aspirate sample).

In some embodiments, the DCAF16 cell sample or cell lysate sample is obtained from the individual by any suitable means of obtaining the sample using well-known and routine clinical methods. Procedures for obtaining tissue samples from an individual are well known. For example, procedures for drawing and processing tissue sample such as from a needle aspiration biopsy is well-known and is employed to obtain a sample for use in the methods provided. Typically, for collection of such a tissue sample, a thin hollow needle is inserted into a mass such as a tumor mass for sampling of cells that, after being stained, will be examined under a microscope.

Sample Preparation and Analysis

In some embodiments, a DCAF16 sample solution comprises a cell sample, a cell lysate sample, or a sample comprising isolated proteins. In some instances, the sample solution comprises a solution such as a buffer (e.g. phosphate buffered saline) or a media. In some embodiments, the media is an isotopically labeled media. In some instances, the sample solution is a cell solution.

In some embodiments, the DCAF16 solution sample (e.g., cell sample, cell lysate sample, or comprising isolated proteins) is incubated with a compound of Formula (I), Formula (IIA), Formula (IIB), or Formula (III) for analysis of protein-probe interactions. In some instances, the solution sample (e.g., cell sample, cell lysate sample, or comprising isolated proteins) is further incubated in the presence of an additional compound probe prior to addition of the compound of Formula (I), Formula (IIA), Formula (IIB), or Formula (III). In other instances, the solution sample (e.g., cell sample, cell lysate sample, or comprising isolated proteins) is further incubated with a ligand, in which the ligand does not contain a photoreactive moiety and/or an alkyne group. In such instances, the solution sample is incubated with a probe and a ligand for competitive protein profiling analysis.

In some cases, the DCAF16 cell sample or the cell lysate sample is compared with a control. In some cases, a difference is observed between a set of probe protein interactions between the sample and the control. In some instances, the difference correlates to the interaction between the small molecule fragment and the proteins.

In some embodiments, one or more methods are utilized for labeling a DCAF16 solution sample (e.g. cell sample, cell lysate sample, or comprising isolated proteins) for analysis of probe protein interactions. In some instances, a method comprises labeling the sample (e.g. cell sample, cell lysate sample, or comprising isolated proteins) with an enriched media. In some cases, the sample (e.g. cell sample, cell lysate sample, or comprising isolated proteins) is labeled with isotope-labeled amino acids, such as $^{13}$C or $^{15}$N-labeled amino acids. In some cases, the labeled sample is further compared with a non-labeled sample to detect differences in probe protein interactions between the two samples. In some instances, this difference is a difference of a target protein and its interaction with a small molecule ligand in the labeled sample versus the non-labeled sample. In some instances, the difference is an increase, decrease or a lack of protein-probe interaction in the two samples. In some instances, the isotope-labeled method is termed SILAC, stable isotope labeling using amino acids in cell culture.

In some embodiments, a method comprises incubating a solution sample (e.g. cell sample, cell lysate sample, or comprising isolated proteins) with a labeling group (e.g., an isotopically labeled labeling group) to tag one or more proteins of interest for further analysis. In such cases, the labeling group comprises a biotin, a streptavidin, bead, resin, a solid support, or a combination thereof, and further comprises a linker that is optionally isotopically labeled. As described above, the linker can be about 5, 6, 7, 8, 9, 10, 11, 12, 13, 14, 15 or more residues in length and might further comprise a cleavage site, such as a protease cleavage site (e.g., TEV cleavage site). In some cases, the labeling group is a biotin-linker moiety, which is optionally isotopically labeled with $^{13}C$ and $^{15}N$ atoms at one or more amino acid residue positions within the linker. In some cases, the biotin-linker moiety is a isotopically-labeled TEV-tag as described in Weerapana, et al., "Quantitative reactivity profiling predicts functional cysteines in proteomes," *Nature* 468(7325): 790-795.

In some embodiments, an isotopic reductive dimethylation (ReDi) method is utilized for processing a sample. In some cases, the ReDi labeling method involves reacting peptides with formaldehyde to form a Schiff base, which is then reduced by cyanoborohydride. This reaction dimethylates free amino groups on N-termini and lysine side chains and monomethylates N-terminal prolines. In some cases, the ReDi labeling method comprises methylating peptides from a first processed sample with a "light" label using reagents with hydrogen atoms in their natural isotopic distribution and peptides from a second processed sample with a "heavy" label using deuterated formaldehyde and cyanoborohydride. Subsequent proteomic analysis (e.g., mass spectrometry analysis) based on a relative peptide abundance between the heavy and light peptide version might be used for analysis of probe-protein interactions.

In some embodiments, isobaric tags for relative and absolute quantitation (iTRAQ) method is utilized for processing a sample. In some cases, the iTRAQ method is based on the covalent labeling of the N-terminus and side chain amines of peptides from a processed sample. In some cases, reagent such as 4-plex or 8-plex is used for labeling the peptides.

In some embodiments, the probe-protein complex is further conjugated to a chromophore, such as a fluorophore. In some instances, the probe-protein complex is separated and visualized utilizing an electrophoresis system, such as through a gel electrophoresis, or a capillary electrophoresis. Exemplary gel electrophoresis includes agarose-based gels, polyacrylamide based gels, or starch based gels. In some instances, the probe-protein is subjected to a native electrophoresis condition. In some instances, the probe-protein is subjected to a denaturing electrophoresis condition.

In some instances, the probe-protein after harvesting is further fragmentized to generate protein fragments. In some instances, fragmentation is generated through mechanical stress, pressure, or chemical means. In some instances, the protein from the probe-protein complexes is fragmented by a chemical means. In some embodiments, the chemical means is a protease. Exemplary proteases include, but are not limited to, serine proteases such as chymotrypsin A, penicillin G acylase precursor, dipeptidase E, DmpA aminopeptidase, subtilisin, prolyl oligopeptidase, D-Ala-D-Ala peptidase C, signal peptidase I, cytomegalovirus assemblin, Lon-A peptidase, peptidase Clp, *Escherichia coli* phage K1F endosialidase CIMCD self-cleaving protein, nucleoporin 145, lactoferrin, murein tetrapeptidase LD-carboxypeptidase, or rhomboid-1; threonine proteases such as ornithine acetyltransferase; cysteine proteases such as TEV protease, amidophosphoribosyltransferase precursor, gamma-glutamyl hydrolase (*Rattus norvegicus*), hedgehog protein, DmpA aminopeptidase, papain, bromelain, cathepsin K, calpain, caspase-1, separase, adenain, pyroglutamyl-peptidase I, sortase A, hepatitis C virus peptidase 2, sindbis virus-type nsP2 peptidase, dipeptidyl-peptidase VI, or DeSI-1 peptidase; aspartate proteases such as beta-secretase 1 (BACE1), beta-secretase 2 (BACE2), cathepsin D, cathepsin E, chymosin, napsin-A, nepenthesin, pepsin, plasmepsin, presenilin, or renin; glutamic acid proteases such as AfuGprA; and metalloproteases such as peptidase_M48.

In some instances, the fragmentation is a random fragmentation. In some instances, the fragmentation generates specific lengths of protein fragments, or the shearing occurs at particular sequence of amino acid regions.

In some instances, the protein fragments are further analyzed by a proteomic method such as by liquid chromatography (LC) (e.g. high performance liquid chromatography), liquid chromatography-mass spectrometry (LC-MS), matrix-assisted laser desorption/ionization (MALDI-TOF), gas chromatography-mass spectrometry (GC-MS), capillary electrophoresis-mass spectrometry (CE-MS), or nuclear magnetic resonance imaging (NMR).

In some embodiments, the LC method is any suitable LC methods well known in the art, for separation of a sample into its individual parts. This separation occurs based on the interaction of the sample with the mobile and stationary phases. Since there are many stationary/mobile phase combinations that are employed when separating a mixture, there are several different types of chromatography that are classified based on the physical states of those phases. In some embodiments, the LC is further classified as normal-phase chromatography, reverse-phase chromatography, size-exclusion chromatography, ion-exchange chromatography, affinity chromatography, displacement chromatography, partition chromatography, flash chromatography, chiral chromatography, and aqueous normal-phase chromatography.

In some embodiments, the LC method is a high performance liquid chromatography (HPLC) method. In some embodiments, the HPLC method is further categorized as normal-phase chromatography, reverse-phase chromatography, size-exclusion chromatography, ion-exchange chromatography, affinity chromatography, displacement chromatography, partition chromatography, chiral chromatography, and aqueous normal-phase chromatography.

In some embodiments, the HPLC method of the present disclosure is performed by any standard techniques well known in the art. Exemplary HPLC methods include hydrophilic interaction liquid chromatography (HILIC), electrostatic repulsion-hydrophilic interaction liquid chromatography (ERLIC) and reverse phase liquid chromatography (RPLC).

In some embodiments, the LC is coupled to a mass spectroscopy as a LC-MS method. In some embodiments, the LC-MS method includes ultra-performance liquid chromatography-electrospray ionization quadrupole time-of-flight mass spectrometry (UPLC-ESI-QTOF-MS), ultra-performance liquid chromatography-electrospray ionization tandem mass spectrometry (UPLC-ESI-MS/MS), reverse phase liquid chromatography-mass spectrometry (RPLC-MS), hydrophilic interaction liquid chromatography-mass spectrometry (HILIC-MS), hydrophilic interaction liquid chromatography-triple quadrupole tandem mass spectrometry (HILIC-QQQ), electrostatic repulsion-hydrophilic interaction liquid chromatography-mass spectrometry (ER-LIC-MS), liquid chromatography time-of-flight mass spectrometry (LC-QTOF-MS), liquid chromatography-tandem mass spectrometry (LC-MS/MS), multidimensional liquid chromatography coupled with tandem mass spectrometry (LC/LC-MS/MS). In some instances, the LC-MS method is LC/LC-MS/MS. In some embodiments, the LC-MS methods of the present disclosure are performed by standard techniques well known in the art.

In some embodiments, the GC is coupled to a mass spectroscopy as a GC-MS method. In some embodiments, the GC-MS method includes two-dimensional gas chromatography time-of-flight mass spectrometry (GC*GC-TOFMS), gas chromatography time-of-flight mass spectrometry (GC-QTOF-MS) and gas chromatography-tandem mass spectrometry (GC-MS/MS).

In some embodiments, CE is coupled to a mass spectroscopy as a CE-MS method. In some embodiments, the CE-MS method includes capillary electrophoresis-negative electrospray ionization-mass spectrometry (CE-ESI-MS), capillary electrophoresis-negative electrospray ionization-quadrupole time of flight-mass spectrometry (CE-ESI-QTOF-MS) and capillary electrophoresis-quadrupole time of flight-mass spectrometry (CE-QTOF-MS).

In some embodiments, the nuclear magnetic resonance (NMR) method is any suitable method well known in the art for the detection of one or more cysteine binding proteins or protein fragments disclosed herein. In some embodiments, the NMR method includes one dimensional (1D) NMR methods, two dimensional (2D) NMR methods, solid state NMR methods and NMR chromatography. Exemplary 1D NMR methods include $^{1}$Hydrogen, $^{13}$Carbon, $^{15}$Nitrogen, $^{17}$Oxygen, $^{19}$Fluorine, $^{31}$Phosphorus, $^{39}$Potassium, $^{23}$Sodium, $^{33}$Sulfur, $^{87}$Strontium, $^{27}$Aluminium, $^{43}$Calcium, $^{35}$Chlorine, $^{37}$Chlorine, $^{63}$Copper, $^{65}$Copper, $^{57}$Iron, $^{25}$Magnesium, $^{199}$Mercury or $^{67}$Zinc NMR method, distortionless enhancement by polarization transfer (DEPT) method, attached proton test (APT) method and 1D-incredible natural abundance double quantum transition experiment (INADEQUATE) method. Exemplary 2D NMR methods include correlation spectroscopy (COSY), total correlation spectroscopy (TOCSY), 2D-INADEQUATE, 2D-adequate double quantum transfer experiment (ADEQUATE), nuclear overhauser effect spectroscopy (NOSEY), rotating-frame NOE spectroscopy (ROESY), heteronuclear multiple-quantum correlation spectroscopy (HMQC), heteronuclear single quantum coherence spectroscopy (HSQC), short range coupling and long range coupling methods. Exemplary solid state NMR method include solid state $^{13}$Carbon NMR, high resolution magic angle spinning (HR-MAS) and cross polarization magic angle spinning (CP-MAS) NMR methods. Exemplary NMR techniques include diffusion ordered spectroscopy (DOSY), DOSY-TOCSY and DOSY-HSQC.

In some embodiments, the protein fragments are analyzed by method as described in Weerapana et al., "Quantitative reactivity profiling predicts functional cysteines in proteomes," *Nature*, 468:790-795 (2010).

In some embodiments, the results from the mass spectroscopy method are analyzed by an algorithm for protein identification. In some embodiments, the algorithm combines the results from the mass spectroscopy method with a protein sequence database for protein identification. In some embodiments, the algorithm comprises ProLuCID algorithm, Probity, Scaffold, SEQUEST, or Mascot.

In some embodiments, a value is assigned to each of the protein from the probe-protein complex. In some embodiments, the value assigned to each of the protein from the probe-protein complex is obtained from the mass spectroscopy analysis. In some instances, the value is the area-under-the curve from a plot of signal intensity as a function of mass-to-charge ratio. In some instances, the value correlates with the reactivity of a Lys residue within a protein.

In some instances, a ratio between a first value obtained from a first protein sample and a second value obtained from a second protein sample is calculated. In some instances, the ratio is greater than 2.5, 3, 3.5, 4, 4.5, 5, 6, 7, 8, 9, 10, 11, 12, 13, 14, 15, 16, 17, 18, 19, or 20. In some cases, the ratio is at most 20.

In some instances, the ratio is calculated based on averaged values. In some instances, the averaged value is an average of at least two, three, or four values of the protein from each cell solution, or that the protein is observed at least two, three, or four times in each cell solution and a value is assigned to each observed time. In some instances, the ratio further has a standard deviation of less than 12, 10, or 8.

In some instances, a value is not an averaged value. In some instances, the ratio is calculated based on value of a protein observed only once in a cell population. In some instances, the ratio is assigned with a value of 20.

Kits/Article of Manufacture

Disclosed herein, in certain embodiments, are kits and articles of manufacture for use to generate a DCAF16 conjugate by a method described herein. In some embodiments, described herein is a kit for detecting DCAF16 ligand interaction. In some embodiments, such kit includes small molecule ligands described herein, small molecule fragments or libraries, compound probes described herein, and/or controls, and reagents suitable for carrying out one or more of the methods described herein. In some instances, the kit further comprises samples, such as a cell sample, and suitable solutions such as buffers or media. In some embodiments, the kit further comprises recombinant DCAF16 proteins for use in one or more of the methods described herein. In some embodiments, additional components of the kit comprises a carrier, package, or container that is compartmentalized to receive one or more containers such as vials, tubes, and the like, each of the container(s) comprising one of the separate elements to be used in a method described herein. Suitable containers include, for example, bottles, vials, plates, syringes, and test tubes. In one embodiment, the containers are formed from a variety of materials such as glass or plastic.

The articles of manufacture provided herein contain packaging materials. Examples of pharmaceutical packaging materials include, but are not limited to, bottles, tubes, bags, containers, and any packaging material suitable for a selected formulation and intended mode of use.

For example, the container(s) include probes, test compounds, and one or more reagents for use in a method disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

"Alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (i-propyl), n-butyl, butyl, s-butyl, n-pentyl, 1,1-dimethylethyl (t-butyl), 3-methylhexyl, 2-methylhexyl, 1-ethyl-propyl, and the like. In some embodiments, the alkyl is methyl or ethyl. In some embodiments, the alkyl is —$CH(CH_3)_2$ or —$C(CH_3)_3$. Unless stated otherwise specifically in the specification, an alkyl group may be optionally substituted as described below. "Alkylene" or "alkylene chain" refers to a straight or branched divalent hydrocarbon chain linking the rest of the molecule to a radical group. In some embodiments, the alkylene is —$CH_2$—, —$CH_2CH_2$—, or —$CH_2CH_2CH_2$—. In some embodiments, the alkylene is —$CH_2$—. In some embodiments, the alkylene is —$CH_2CH_2$—. In some embodiments, the alkylene is —$CH_2CH_2CH_2$—.

"Alkoxy" refers to a radical of the formula —OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy.

"Heteroalkylene" refers to an alkyl radical as described above where one or more carbon atoms of the alkyl is replaced with a O, N or S atom. "Heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to —$OCH_2OMe$, —$OCH_2CH_2OMe$, or —$OCH_2CH_2OCH_2CH_2NH_2$. Representative heteroalkylene groups include, but are not limited to —$OCH_2CH_2O$—, —$OCH_2CH_2OCH_2CH_2O$—, or —$OCH_2CH_2OCH_2CH_2OCH_2CH_2O$—.

"Alkylamino" refers to a radical of the formula —NHR or —NRR where each R is, independently, an alkyl radical as defined above. Unless stated otherwise specifically in the specification, an alkylamino group may be optionally substituted as described below.

The term "aromatic" refers to a planar ring having a delocalized π-electron system containing 4n+2 π electrons, where n is an integer. Aromatics can be optionally substituted. The term "aromatic" includes both aryl groups (e.g., phenyl, naphthalenyl) and heteroaryl groups (e.g., pyridinyl, quinolinyl).

"Aryl" refers to an aromatic ring wherein each of the atoms forming the ring is a carbon atom. Aryl groups can be optionally substituted. Examples of aryl groups include, but are not limited to phenyl, and naphthyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted.

"Carboxy" refers to —$CO_2H$. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to:

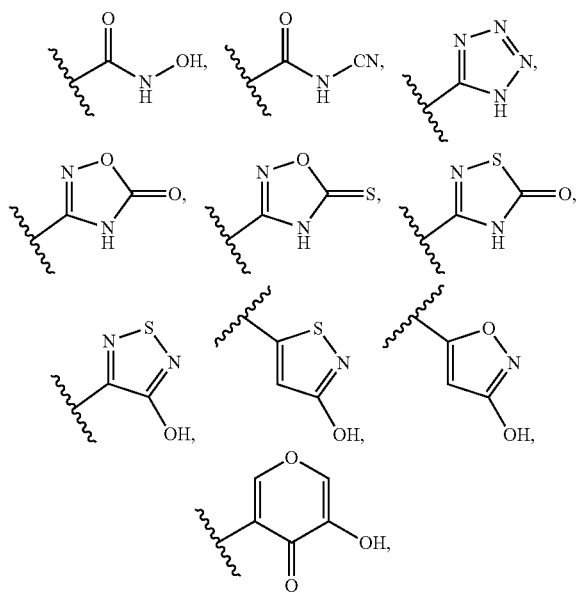

and the like.

"Cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. Monocyclic cyclcoalkyl radicals include, for example, cyclopropyl, cyclobutyl, cyclopentyl, cyclohexyl, cycloheptyl, and cyclooctyl. In some embodiments, the monocyclic cyclcoalkyl is cyclopropyl, cyclobutyl, cyclopentyl or cyclohexyl. In some embodiments, the monocyclic cyclcoalkyl is cyclopentyl. Polycyclic radicals include, for example, adamantyl, norbornyl, decalinyl, and 3,4-dihydronaphthalen-1(2H)-one. Unless otherwise stated specifically in the specification, a cycloalkyl group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" refers to an alkoxy radical, as defined above, that is substituted by one or more halo radicals, as defined above, e.g., trifluoromethoxy, difluoromethoxy, fluoromethoxy, trichloromethoxy, 2,2,2-trifluoroethoxy, 1,2-difluoroethoxy, 3-bromo-2-fluoropropoxy, 1,2-dibromoeth-oxy, and the like. Unless stated otherwise specifically in the specification, a haloalkoxy group may be optionally substituted.

"Heterocycloalkyl" or "heterocyclyl" or "heterocyclic ring" refers to a stable 3- to 14-membered non-aromatic ring radical comprising 2 to 10 carbon atoms and from one to 4 heteroatoms selected from the group consisting of nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. In some embodiments, heterocycloalkyls have from 2 to 10 carbons, 0-2 N atoms, 0-2 O atoms, and 0-1 S atoms in the ring. In some embodiments, heterocycloalkyls have from 2 to 10 carbons, 1-2 N atoms, 0-1 O atoms, and 0-1 S atoms in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to an aryl group that includes one or more ring heteroatoms selected from nitrogen, oxygen and sulfur. The heteroaryl is monocyclic or bicyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, a bicyclic heteroaryl is a $C_6$-$C_9$heteroaryl.

The term "optionally substituted" or "substituted" means that the referenced group may be substituted with one or more additional group(s) individually and independently selected from alkyl, haloalkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halogen, acyl, acyloxy, —$CO_2H$, —$CO_2$alkyl, nitro, and amino, including mono- and di-substituted amino groups (e.g. —$NH_2$, —NHR, —$N(R)_2$), and the protected derivatives thereof. In some embodiments, optional substituents are independently selected from alkyl, alkoxy, haloalkyl, cycloalkyl, halogen, —CN, —$NH_2$, —$NH(CH_3)$, —$N(CH_3)_2$, —OH, —$CO_2H$, and —$CO_2$alkyl. In some embodiments, optional substituents are independently selected from fluoro, chloro, bromo, iodo, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

As used herein The term"heterobifunctional degrader" refers to proteolysis-targeting chimera molecules having generally three components, a ubiquitin ligase (E3) binding moiety, at least one linker moiety, and a protein binding moiety (PB moiety, also referred to herein as "D"). Specifically, the E3 binding moiety used herein is a DCAF16 ligand moiety.

EXAMPLES

These examples are provided for illustrative purposes only and not to limit the scope of the claims provided herein.

Example 1: Covalent Bifunctional Compounds Degrading Nuclear FKBP12

Three scout fragments—KB02, KB03, and KB05—were fused to the SLF ligand that binds tightly and selectively to FKBP12 (FIG. 1A), a cytosolic prolyl isomerase that has been frequently used to study ligand-induced protein degradation (Winter, G. E. et al. DRUG DEVELOPMENT. Phthalimide conjugation as a strategy for in vivo target protein degradation. *Science* 348, 1376-1381 (2015); and Nabet, B. et al. The dTAG system for immediate and target-specific protein degradation. *Nat Chem Biol* 14, 431-441 (2018); both herein incorporated by reference).

Example 2: Confirmation of Nuclear FKBP12 Degradation

Figure 4A:
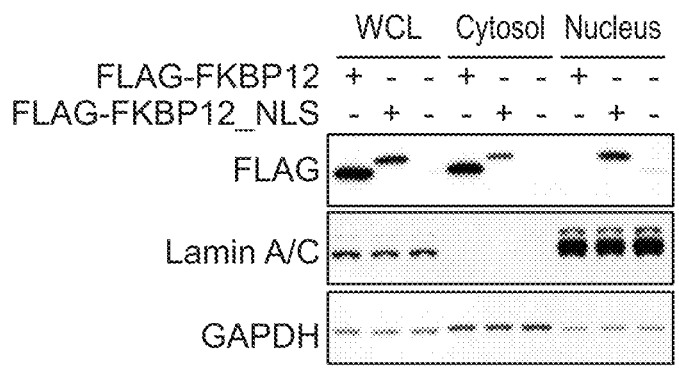
FIG. 4A-FIG. 4C illustrate stable expression of FLAG-FKBP12 and FLAG-FKBP12_NLS in HEK293T cells and characterization of a lenalidomide-SLF bifunctional protein degrading compound.
Figure 4B:
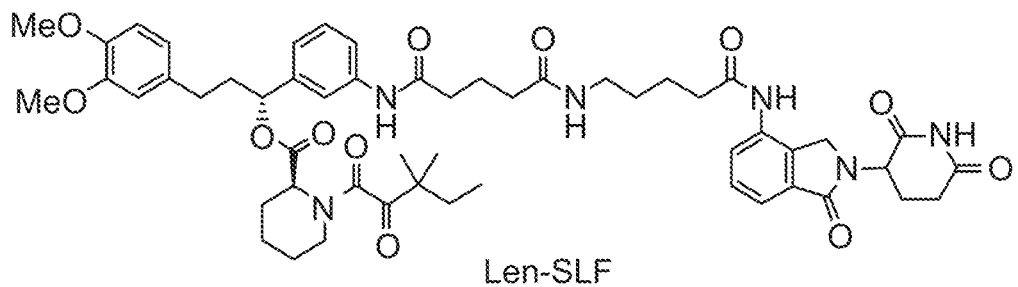
Figure 4C:
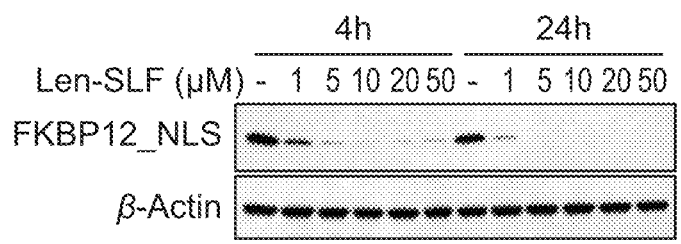
Figure 4C:
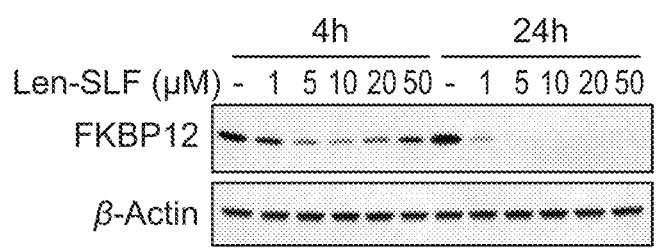

FLAG-tagged variants of FKBP12 (FLAG-FKBP12) or (2) FKBP12 with a C-terminal nuclear localization sequence (FLAG-FKBP12_NLS) were then stably expressed in HEK293T cells to provide cell models for evaluating cytosolic- and nuclear-localized E3-mediated degradation pathways, respectively. FIG. 4A shows subcellular fractionation followed by western blotting of the stably expressed FLAG-FKBP12 and FLAG-FKBP12-NLS in HEK293T cells.

Figure 1B:
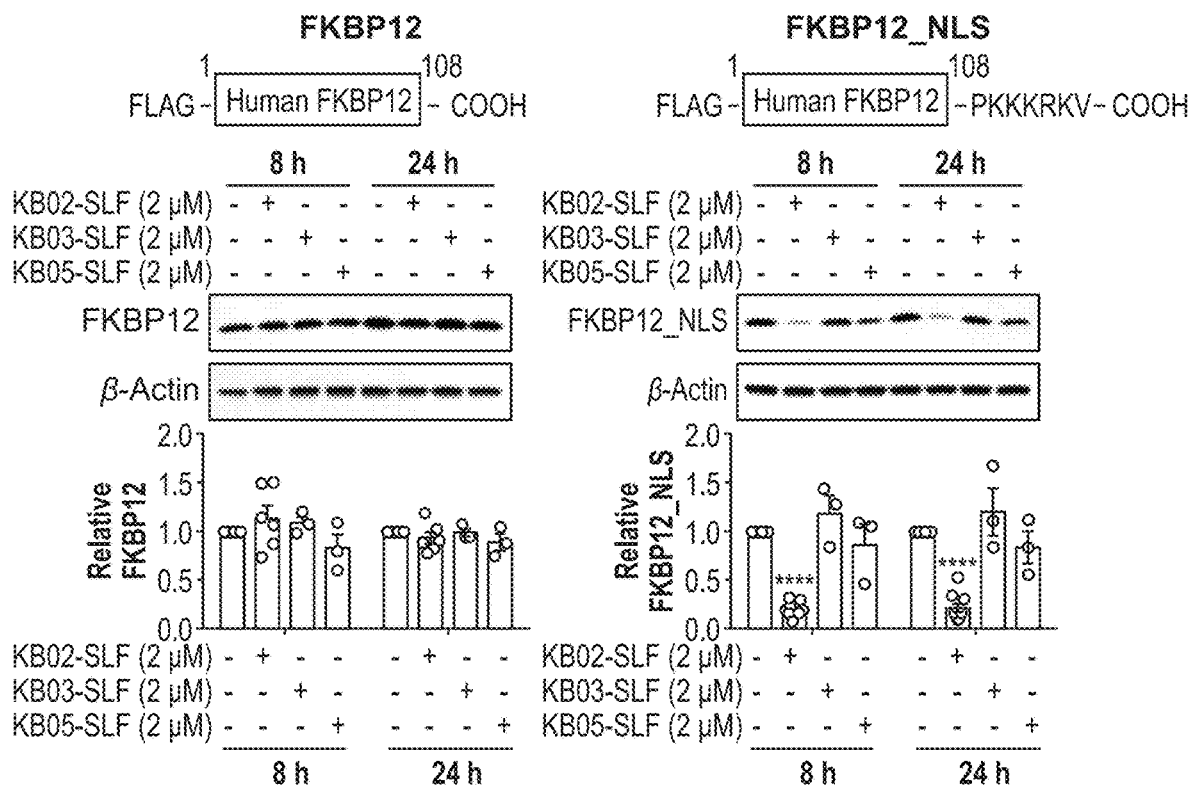
Figure 5A:
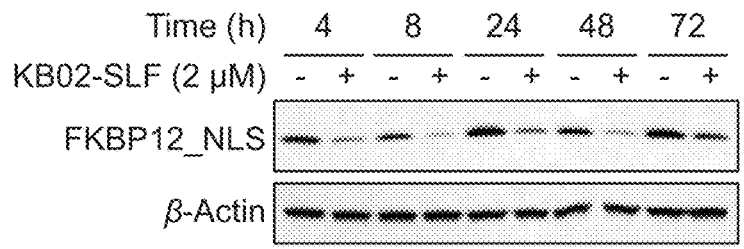
FIG. 5A-FIG. 5D illustrate characterization of KB02-SLF bifunctional protein degrading compound.

Anti-FLAG western blotting confirmed that both cytosolic and nuclear FKBP12 were degraded by lenalidomide-SLF, a bifunctional molecule comprised of SLF coupled to lenalidomide, a ligand for the E3 ligase cereblon (CRBN) that has been widely deployed in targeted protein degradation studies. The electrophilic scout fragment-SLF bifunctional compounds were evaluated next for effects on FKBP12 HEK293T cells. Under the treatment conditions (2 μM, 8 or 24 h), none of the compounds altered cytosolic FKBP12 (FIG. 1B, left blots). On the other hand, the KB02-SLF compound promoted a substantial reduction in nuclear FKBP12 (FIG. 1B) that was sustained across a 4-72 h time frame (FIG. 5A). Cell imaging studies confirmed the selective loss of nuclear-localized FKBP12 in KB02-SLF-treated cells (FIG. 1C). These imaging studies, along with western blotting experiments (FIG. 4A), pointed to a fraction of FKBP12 that remained cytoplasmically localized in FLAG-FKBP12_NLS-transfected cells and was consequently unaffected by KB02-SLF treatment (FIG. 1C).

Example 3: Covalent Modification and Linkers

Figure 5B:
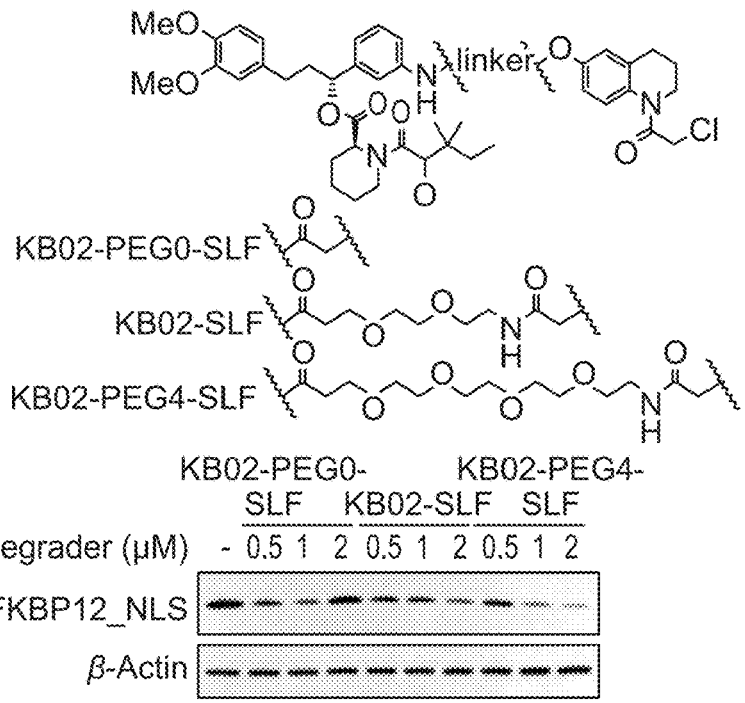
Figure 5C:
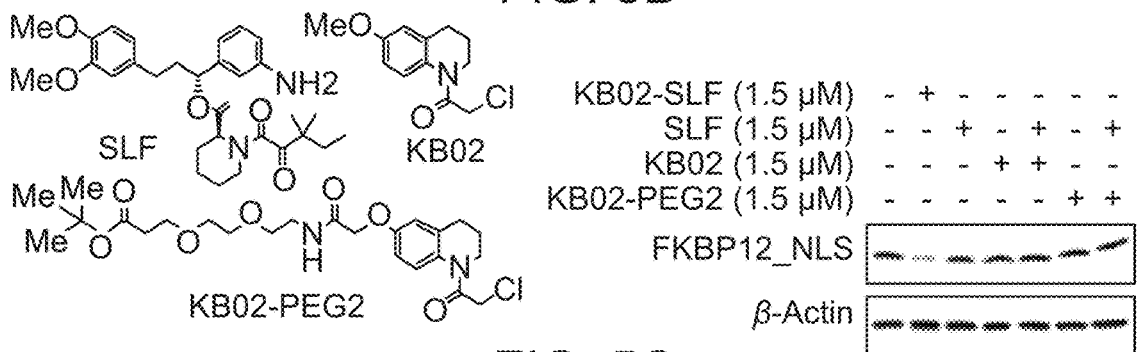
Figure 5D:
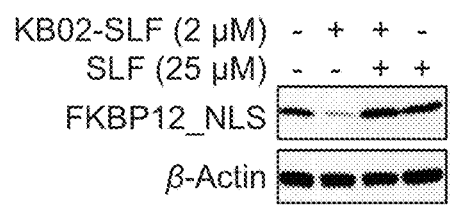

Reductions in FKBP12_NLS were not observed with an analogue of KB02-SLF where the electrophilic alpha-chloroacetamide group was replaced with an unreactive acetamide (C-KB02-SLF; FIG. 1D, FIG. 1E), indicating that the mechanism of action of KB02-SLF involved covalent modification of one or more proteins. KB02-SLF, as well as analogues of this compound with different linker lengths (FIG. 5B), promoted the loss of FKBP12_NLS across a concentration of –0.5-5 but showed reductions in activity at higher concentrations (FIG. 1F and FIG. 5B). Such parabolic concentration-dependence is a feature of bifunctional protein degrading compounds, where binary complexes gain prevalence over ternary complexes at higher cellular concentrations of compound (Gadd, M. S. et al. *Nat Chem Biol* 13, 514-521 (2017)). KB02-SLF showed evidence of cytotoxicity at higher test concentrations (>10 μM, see below), which might also impair protein degradation pathways, however data were obtained consistent with proteolytic degradation for KB02-SLF, as FKBP12_NLS was not reduced in cells treated with the two separate components (KB02 and SLF) of the KB02-SLF bifunctional compound (FIG. 5C). Pre-treatment with SLF did, on the other hand, block the KB02-SLF-induced loss of FKBP12_NLS (FIG. 5D).

Example 4: KB02-SLF Induced Polyubiquitination of Nuclear aFKBP12

Figure 2A:
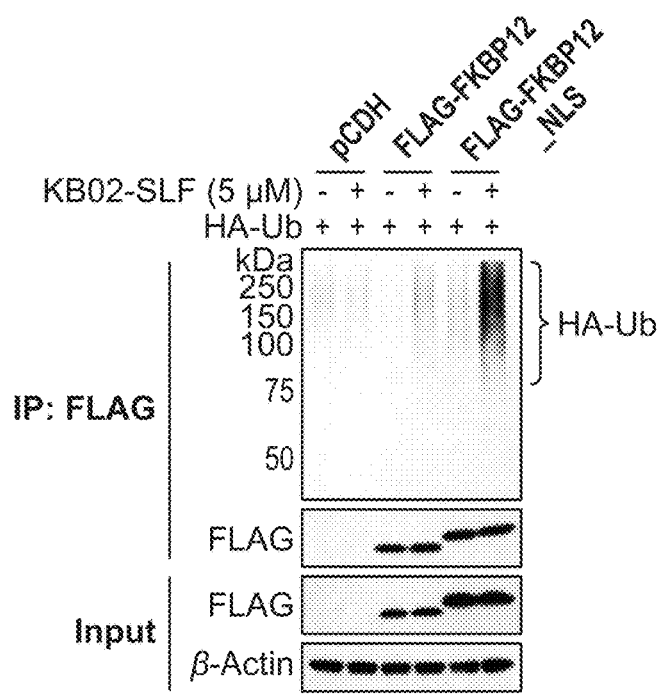
Figure 2B:
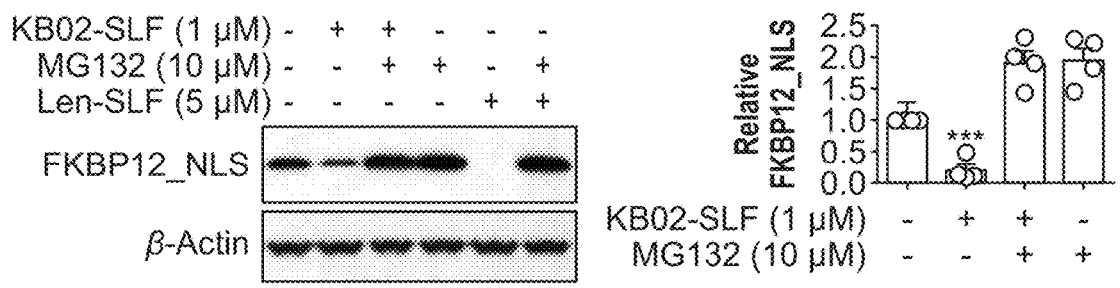
Figure 2C:
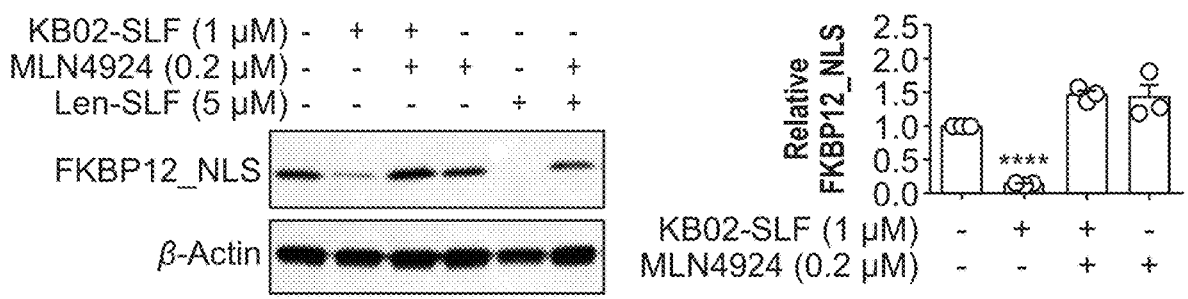
Figure 6:
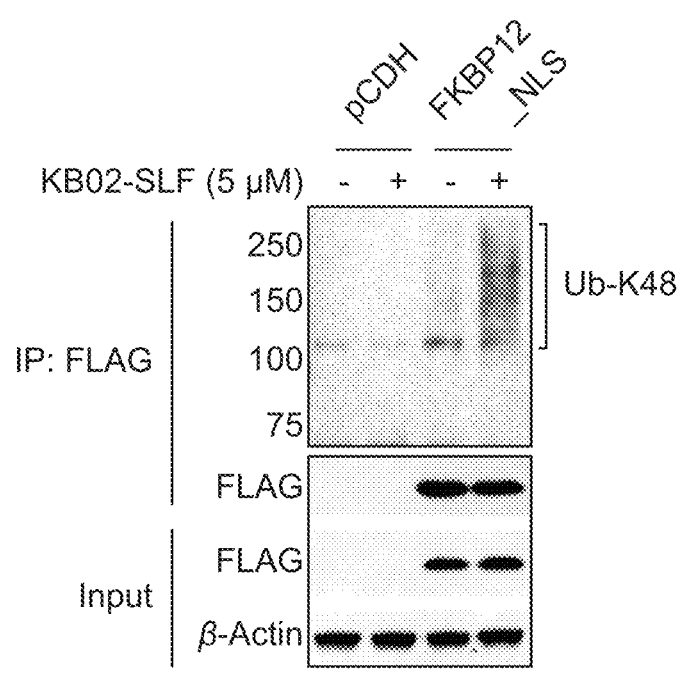
FIG. 6 is a picture of a Western blot showing that KB02-SLF induced K48-linked polyubiquitination on FLAG-FKBP12_NLS. HEK293T cells stably expressing FLAG-FKBP12_NLS were treated with KB02-SLF (5 μM) and MG132 (10 μM) for 2 hours, and FLAG-FKBP12_NLS was then immunoprecipitated and analyzed by western blotting for K48-linked ubiquitination.

KB02-SLF induced polyubiquitination of nuclear FKBP12_NLS, but not cytosolic FKBP12 (FIG. 2A and FIG. 6), and KB02-SLF-mediated loss of FKBP12_NLS was blocked by the proteasome inhibitor MG132 (FIG. 2B) and neddylation inhibitor MLN4924 (Soucy, T. A. et al. *Nature* 458, 732-736 (2009)) (FIG. 2C). Similar effects of KB02-SLF on FKBP12_NLS were observed in a second human cell line (MDA-MB-231) (FIG. 7). These data, taken together, supported that KB02-SLF promoted the proteasomal degradation of nuclear-localized FKBP12 via the action of a Cullin-RING ligase (CRL).

Figure 7A:
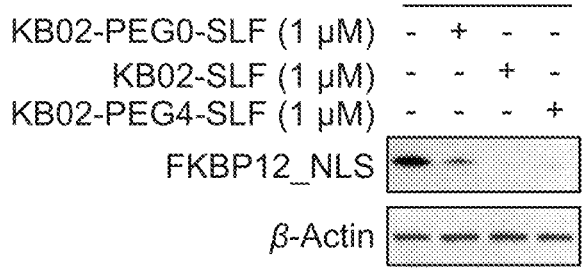
FIG. 7A-FIG. 7E illustrate KB02-SLF degradation of FLAG-FKBP12_NLS in MDA-MB-231 cells.
Figure 7B:
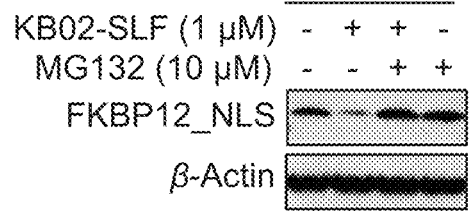
Figure 7C:
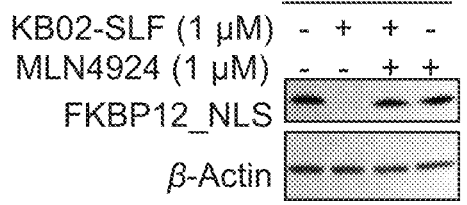
Figure 7D:
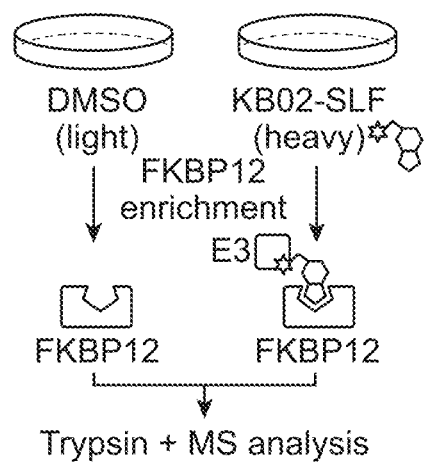
Figure 7E:
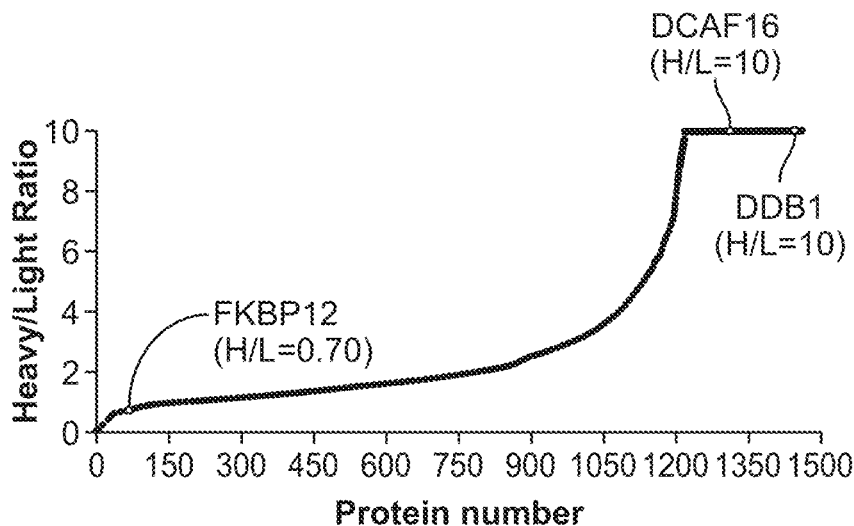
Figures 8A, 8B:
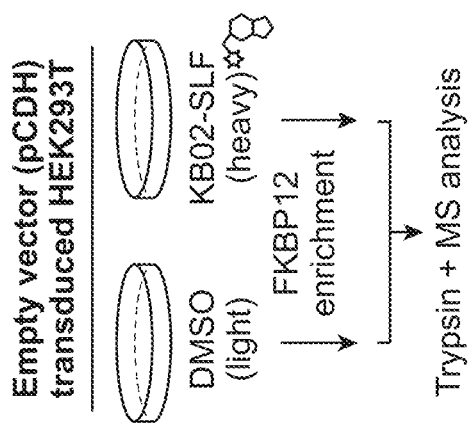

Working under a model where KB02-SLF induced the degradation of FKBP12_NLS by covalently reacting with one or more CRL(s), it was first attempted to identify the recruited CRL(s) using a chemical proteomic method termed isoTOP-ABPP (isotopic tandem orthogonal proteolysis-activity-based protein profiling), where ligand-engaged cysteines in cells are mapped by competitive blockade of reactivity with an iodoacetamide (IA)-alkyne probe. However, cysteines were not observed on CRL(s) that were strongly engaged (>75%) by KB02-SLF in these chemical proteomic experiments. Alternatively, it was considered that KB02-SLF would show low stoichiometry engagement of a CRL, which would then function catalytically to drive FKBP12_NLS degradation. Such low fractional occupancy ligand-protein interactions are not easily mapped by competitive profiling methods like isoTOP-ABPP. As such an alternative proteomic approach was employed, in which FLAG-mediated affinity enrichment was used to identify proteins that associated with FKBP12_NLS in a KB02-SLF-dependent manner (FIG. 2D). This experimental set up identified two substrate components of CRLs—DCAF16 and DTL—that were substantially enriched in HEK 293T cells treated with KB02-SLF compared to DMSO-treated control cells (FIG. 2E and FIG. 8B). Neither DCAF16 nor DTL were enriched by KB02-SLF in an additional control experiment performed with mock-transfected cells lacking FKBP12_NLS (FIG. 8A, FIG. 8B). KB02-SLF-dependent enrichment of DCAF16 was also observed in MDA-MB-231 cells (FIG. 7D, FIG. 7E).

Figure 3A:
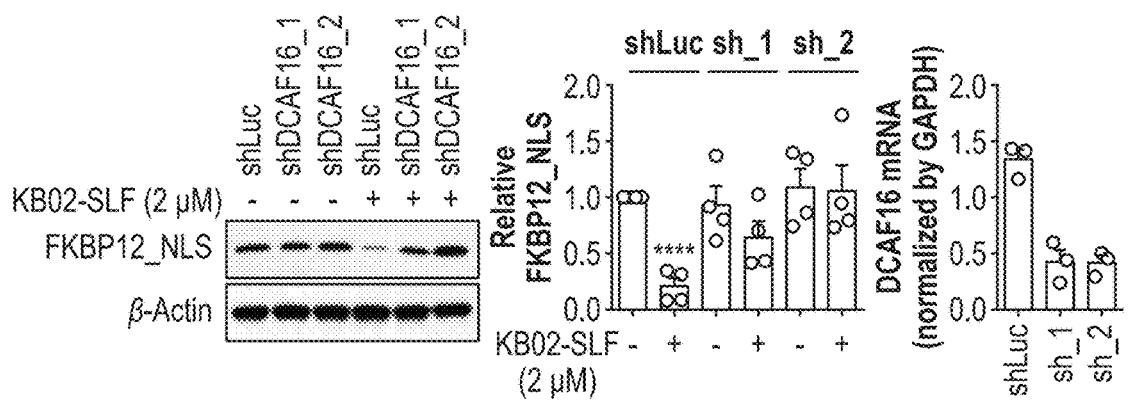
FIG. 3A-FIG. 3K illustrate DCAF16 mediated electrophilic bifunctional protein degrading compound-induced degradation of nuclear proteins.
Figure 3B:
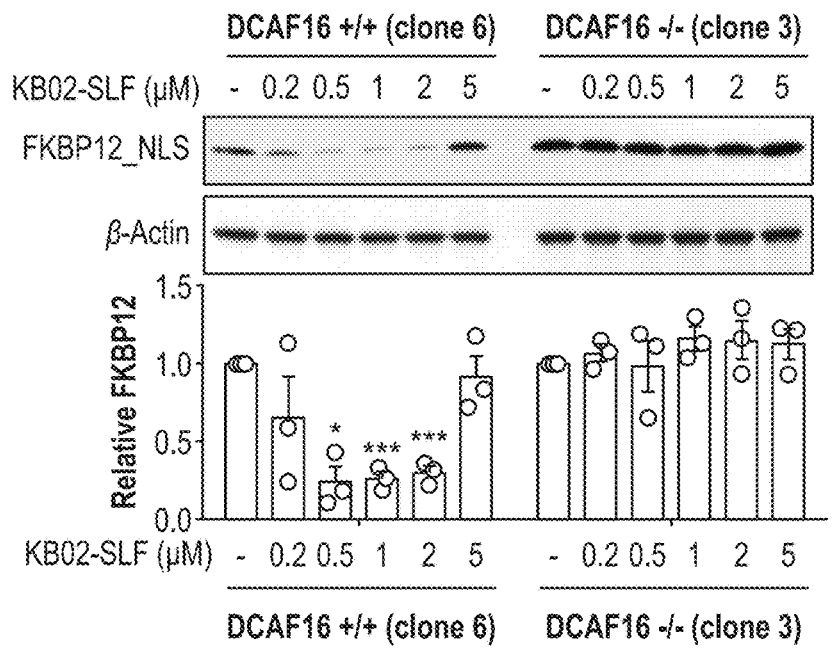
Figure 3C:
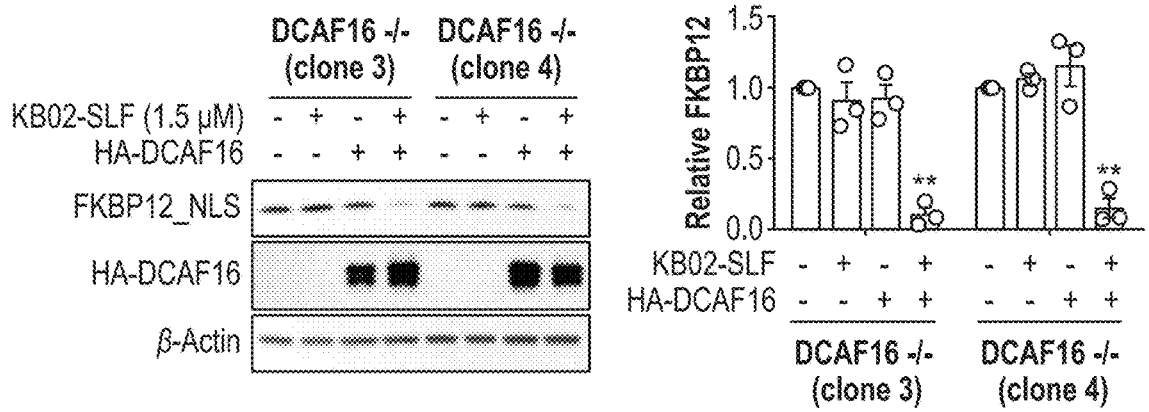
Figure 9A:
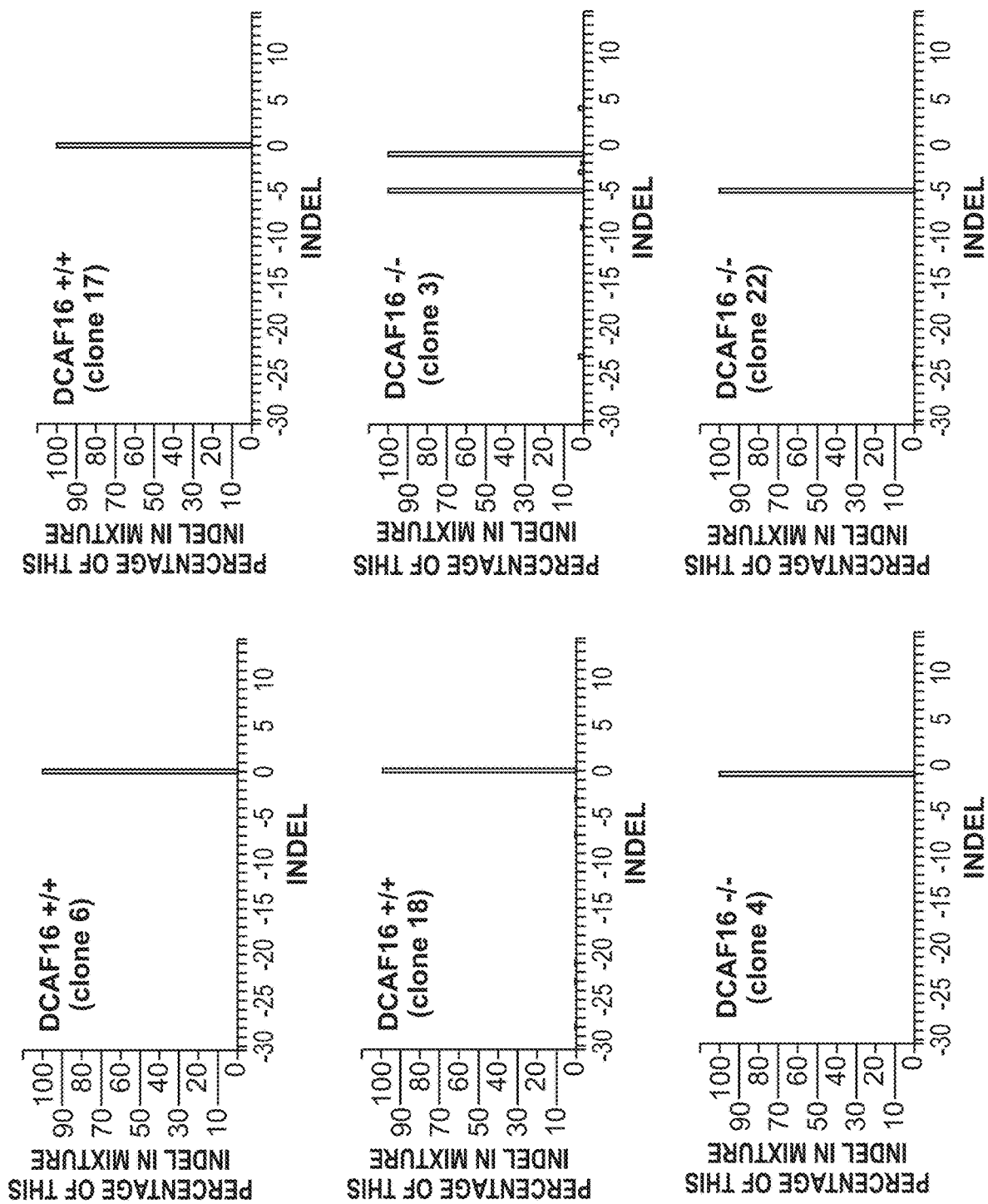
Figure 9B:
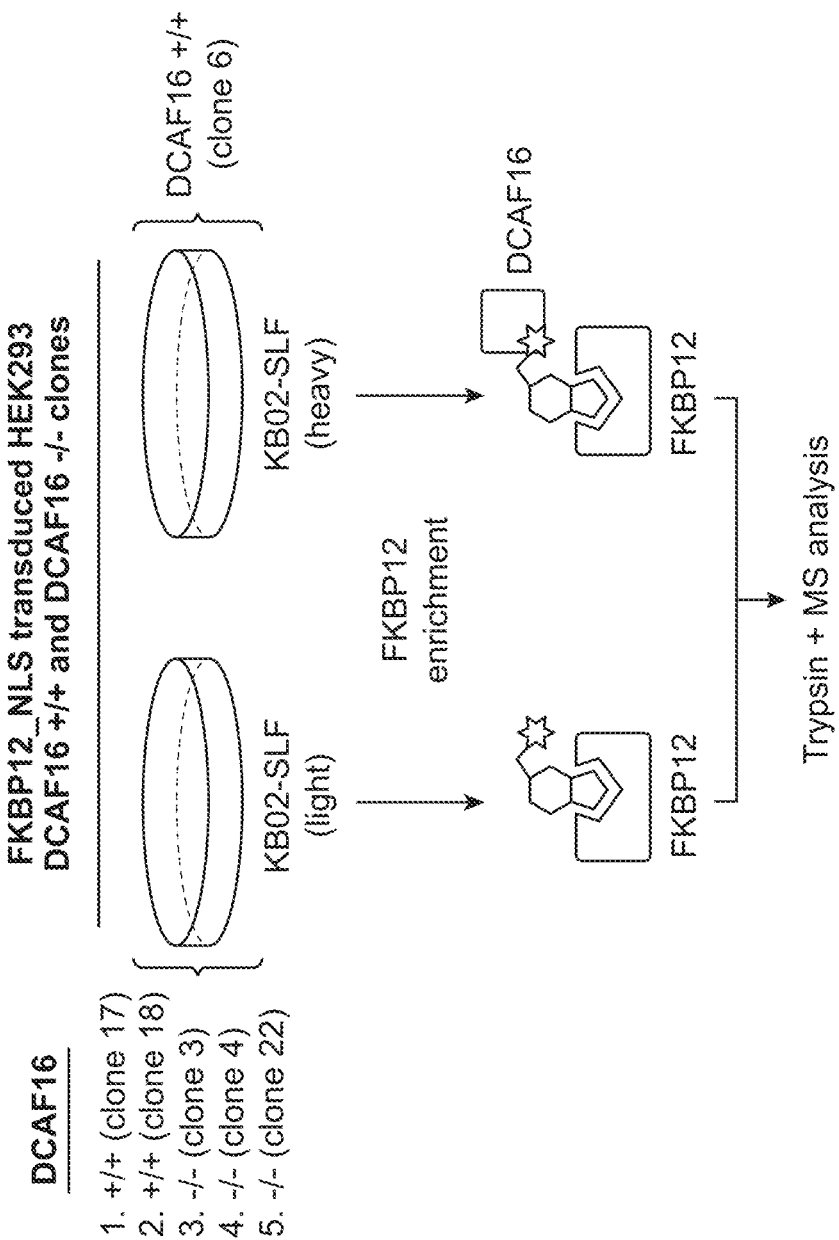
Figure 9C:
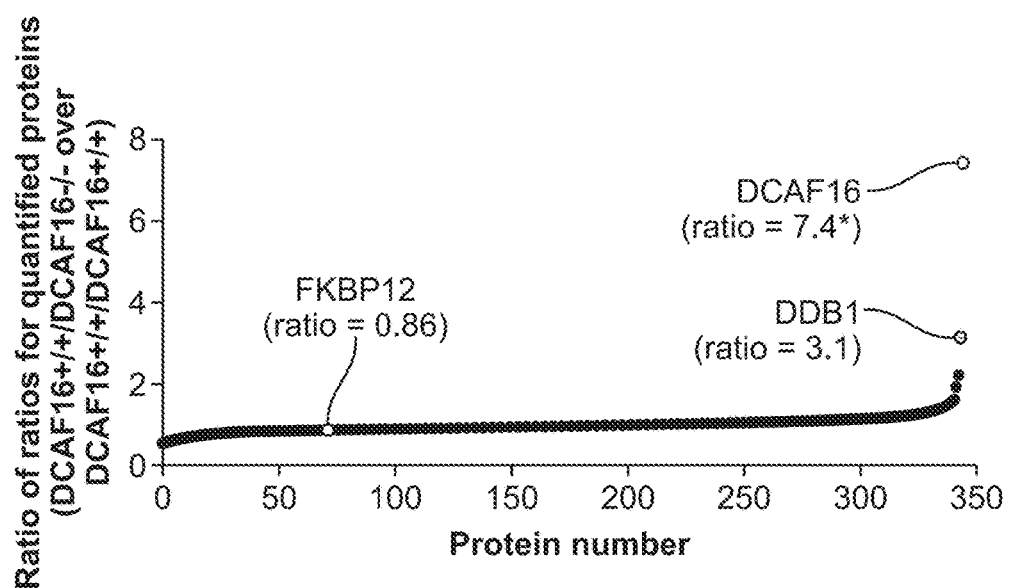

Notably, both DCAF16 and DTL are predicted to be nuclear proteins. DTL (also known as CDT2 and DCAF2) plays a key role in cell cycle control and DNA damage response (Jin, J. et al. *Mol Cell* 23, 709-721 (2006)). DCAF16, on the other hand, is a poorly characterized, predicted substrate recognition component of CLRs that shares negligible homology with other DCAF proteins. Nuclear localization was confirmed through use of an HA-tagged DCAF16 in transfected HEK293T cells (FIG. 2F). Consistent with KB02-SLF engaging functional CRL complexes potentially containing DCAF16 and/or DTL, enrichment of additional CRL components—DDB1 and CUL4A/B—in KB02-SLF-treated cells was also observed (FIG. 2E and FIG. 8B). Next small hairpin RNA (shRNA)-mediated knockdown was used to find that reductions in DCAF16, but not DTL, substantially prevented KB02-SLF-mediated degradation of FKBP12_NLS (FIG. 3A and FIG. 8C). shRNA-knockdown of DCAF16 also abolished KB02-SLF-induced polyubiquitination of FKBP12_NLS (FIG. 8D). The involvement of DCAF16 in KB02-SLF-mediated degradation of FKBP12_NLS was confirmed by CRISPR-based genetic knockout using a Cas9/gRNA ribonucleoprotein (RNP) complex. Genomic sequencing and mass spectrometry-based proteomics were used to confirm the genetic disruption of DCAF16 in three independent clones (DCAF16−/−) compared to three wild type DCAF16 clones (DCAF16+/+) (FIG. 9A-FIG. 9C). KB02-SLF supported the degradation of FKBP12_NLS in all three DCAF16+/+ clones, but not in any of the three DCAF16−/− clones (FIG. 3B and FIG. 9D). Moreover, recombinant expression of HA-tagged DCAF16 restored KB02-SLF-induced FKBP12_NLS degradation in the DCAF16−/− cells (FIG. 3C). The degradation of HA-DCAF16 was not observed following treatment of KB02-SLF (FIG. 3C and FIG. 9E). These data, taken together, demonstrate that KB02-SLF-mediated degradation of FKBP12_NLS requires DCAF16.

Example 5: Ternary Complex Formation

Figure 3D:
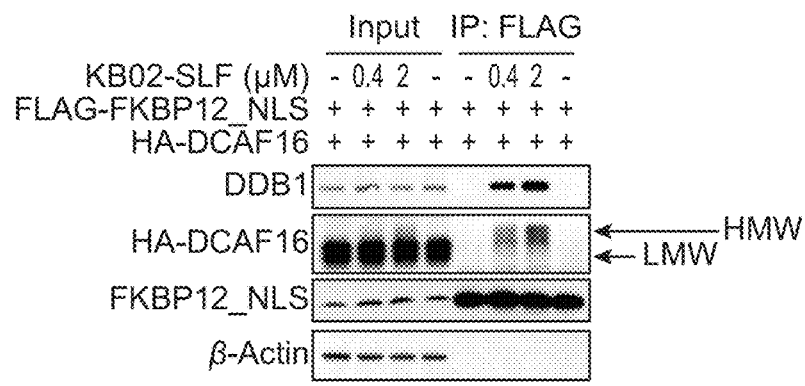
Figure 10A:
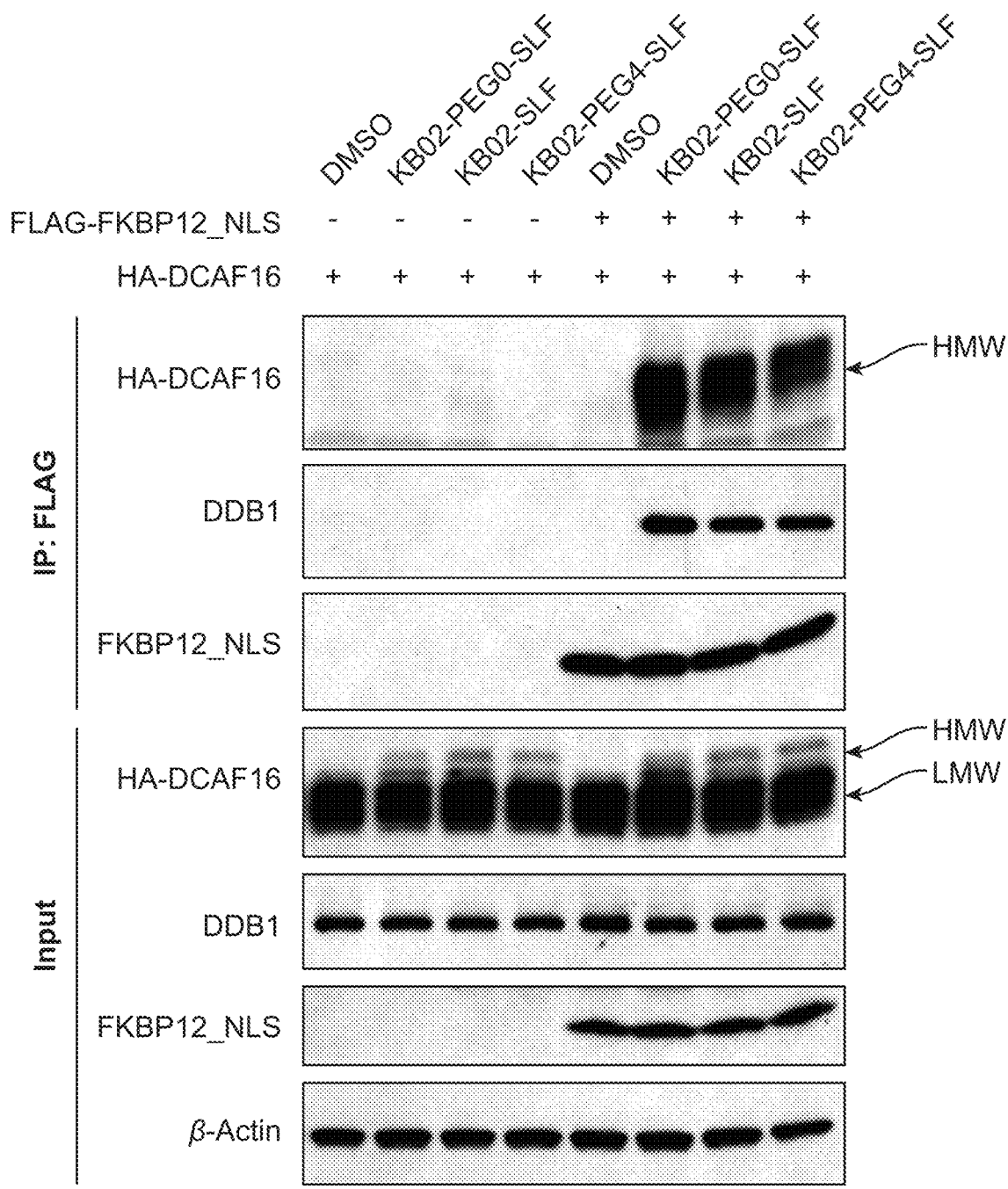
FIG. 10A-FIG. 10F illustrate KB02-SLF mediation of a ternary complex interaction between FLAG-FKBP12_NLS and HA-DCAF16.
Figure 10B:
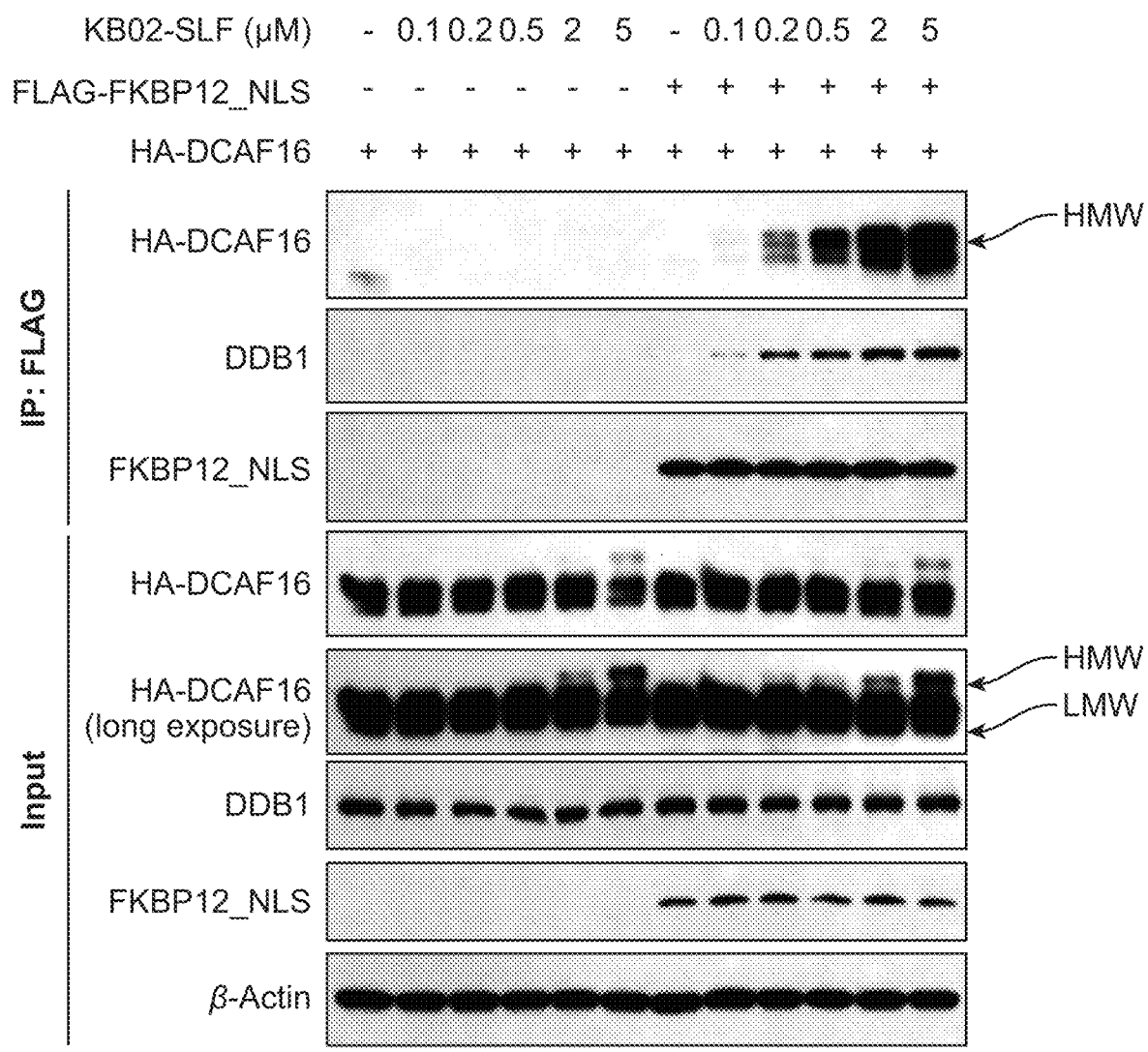
Figure 10C:
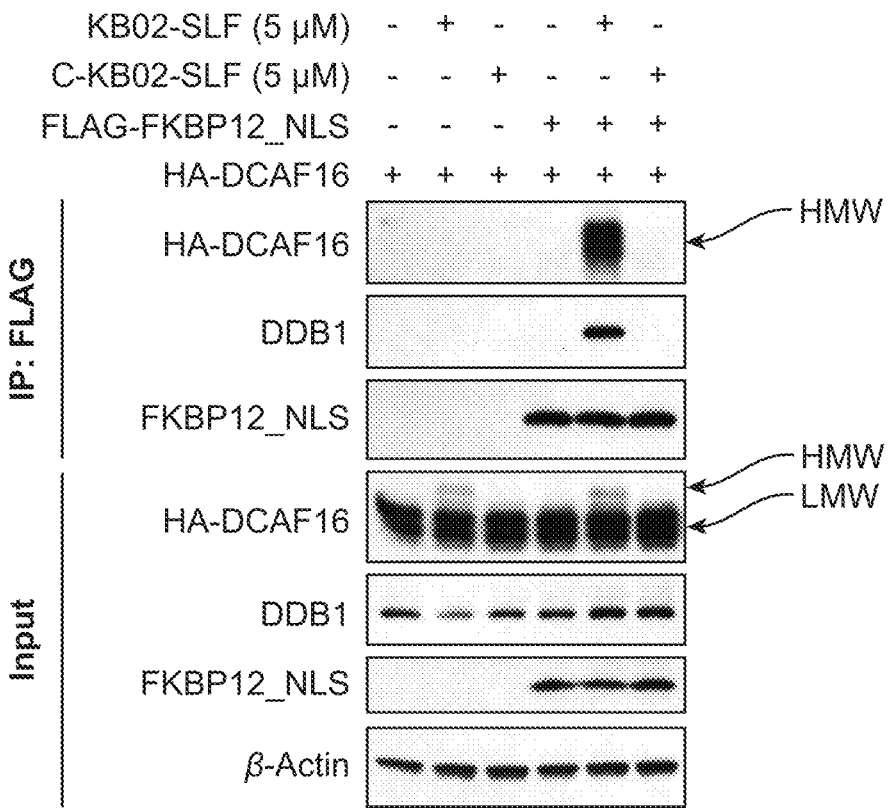
Figure 10D:
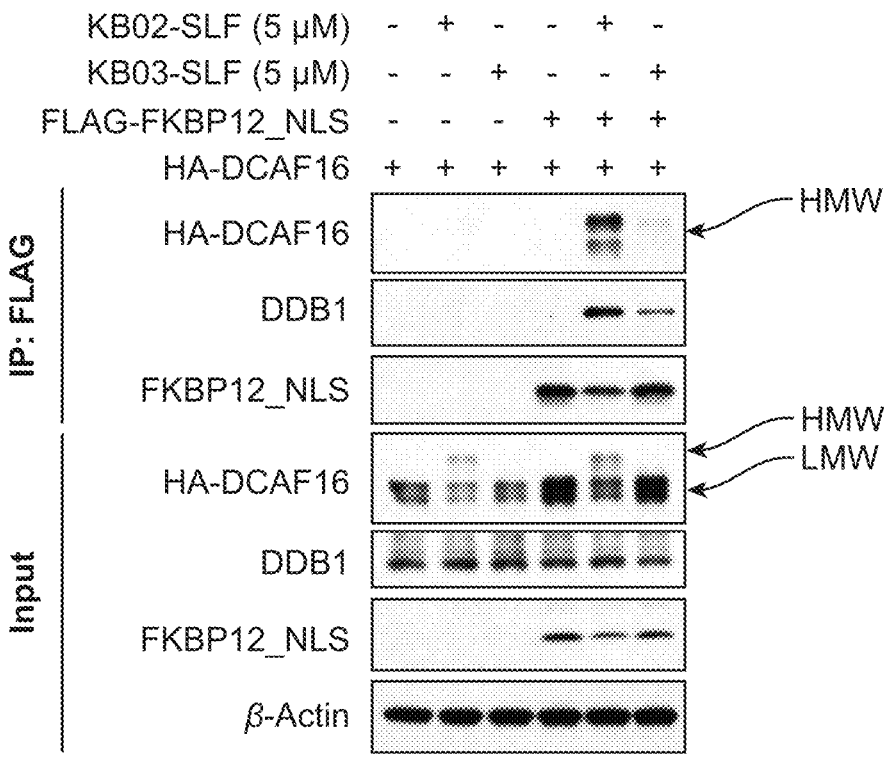
Figure 10E:
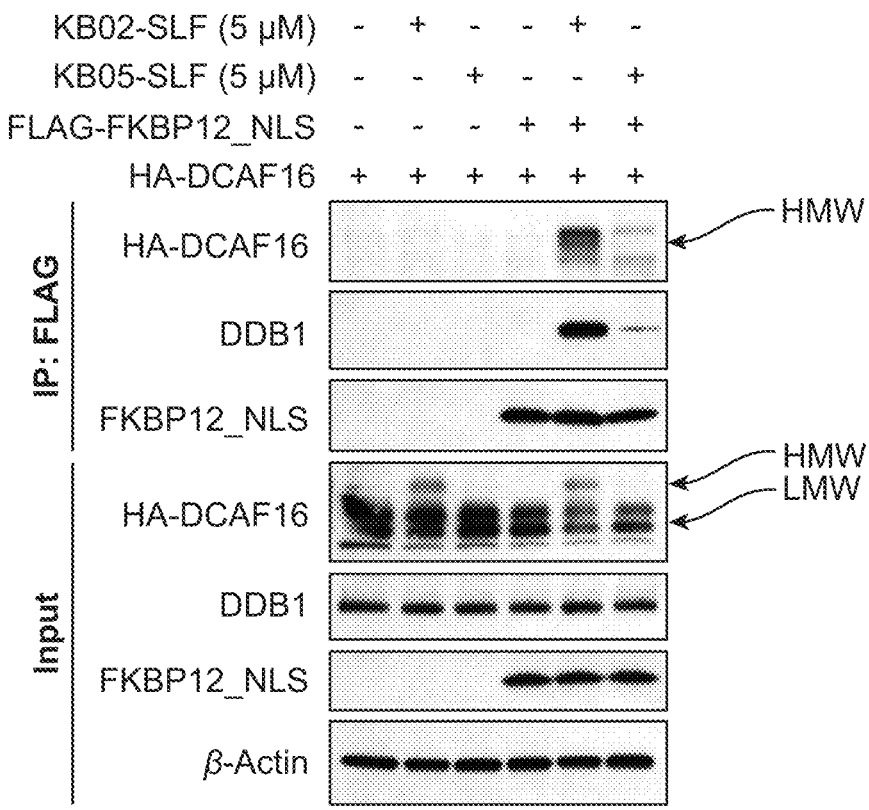
Figure 10F:
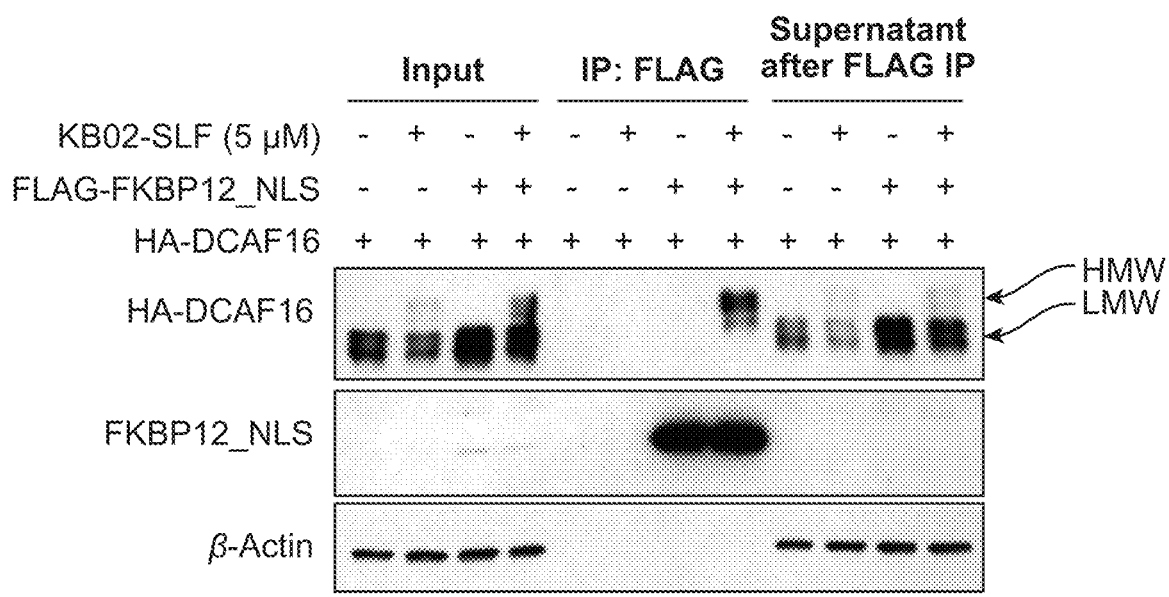

To support a ternary complex formation involving a DCAF16-CRL, it was found that HA-DCAF16 and DDB1 co-immunoprecipitated with FLAG-FKBP12_NLS in the presence of KB02-SLF (FIG. 3D) or its linker analogues (FIG. 10A). KB02-SLF-treated cells showed a higher molecular weight (HMW) form of HA-DCAF16, consistent with covalent modification of this protein by KB02-SLF (FIG. 3D and FIG. 10A-FIG. 10F). Only a modest fraction of HA-DCAF16 was converted to this HMW in the presence of increasing concentrations of KB02-SLF (FIG. 3D and FIG. 10B). Notably, however, the HMW-DCAF16 was exclusively co-immunoprecipitated with FKBP12_NLS (FIG. 3D and FIG. 10F), supporting a ternary complex model where KB02-SLF is covalently and non-covalently bound to DCAF16 and FKBP12_NLS, respectively. Also consistent with this model, DCAF16 was not co-immunoprecipitated from cells treated with the non-electrophilic control compound C-KB02-SLF (FIG. 10C) or with the other two electrophilic bifunctional compounds (KB03-SLF and KB05-SLF) that did not support FKBP12_NLS degradation (FIG. 10D, FIG. 10E).

Example 6: DCAF16 Engagement

Figure 3E:
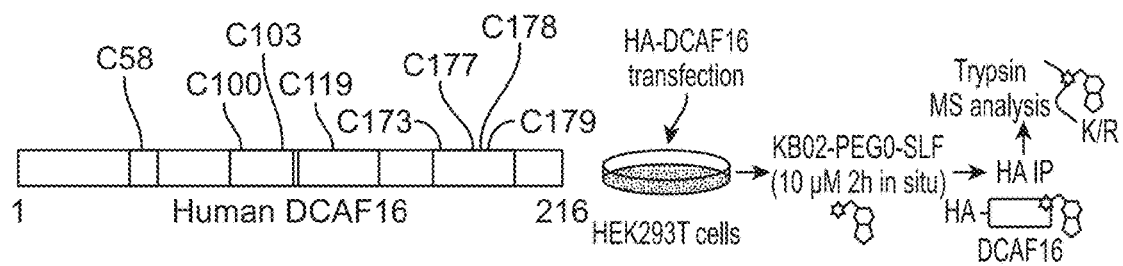
Figure 3F:
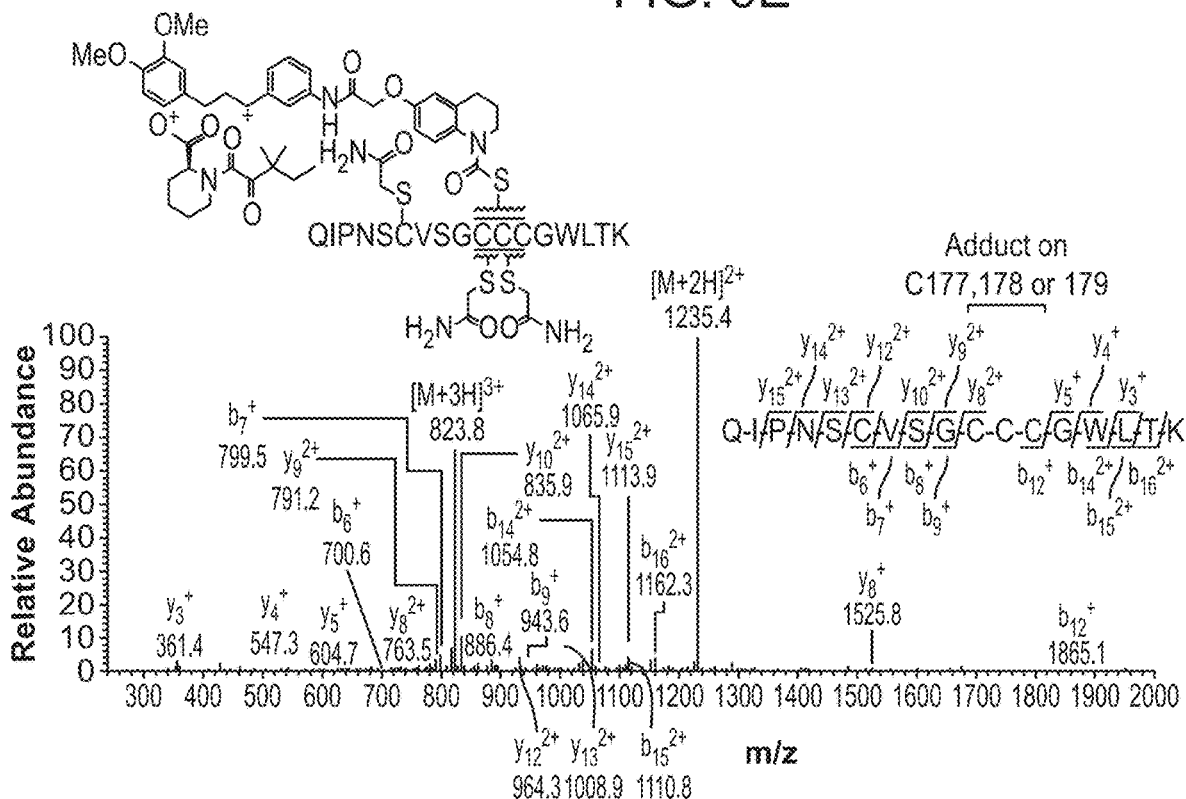
Figure 11A:
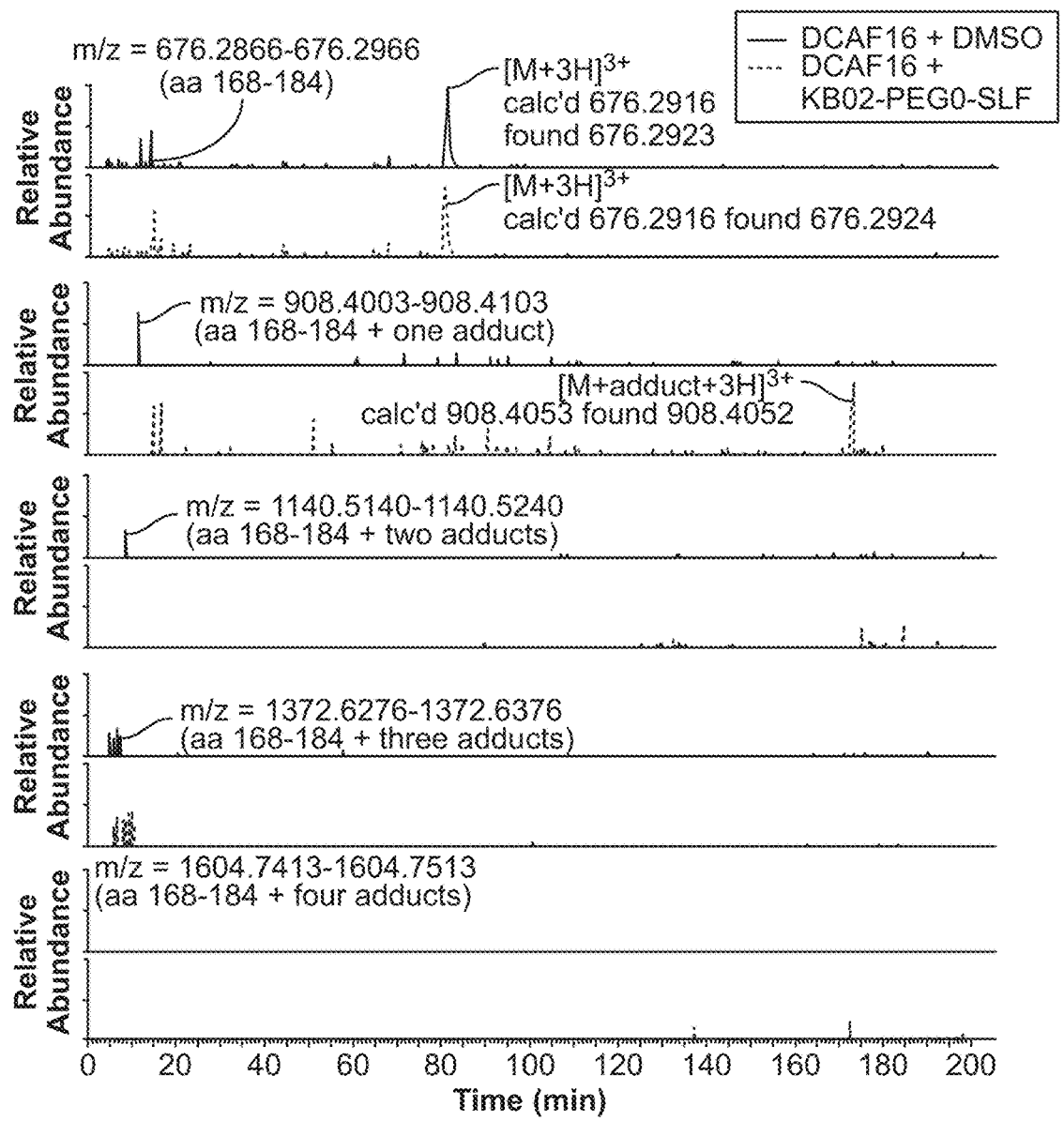
FIG. 11A-FIG. 11C illustrate MS analysis KB02-PEG9-SLF-modified cysteine(s) in DCAF16.
Figure 11A:
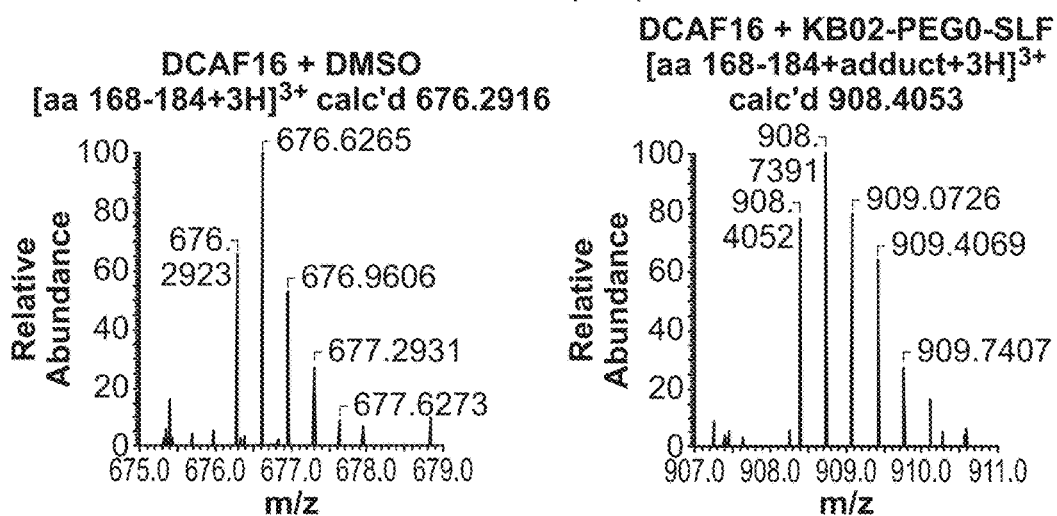
Figure 11B:
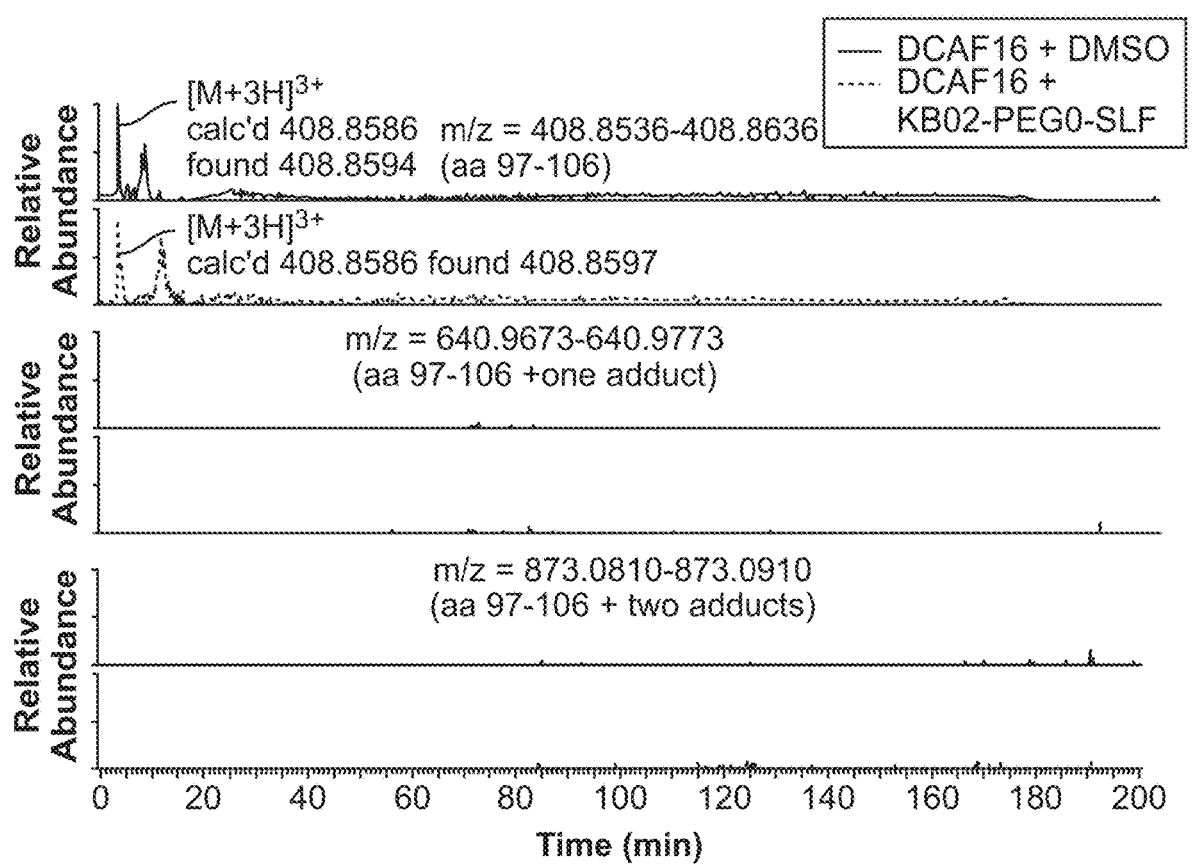
Figure 11B:
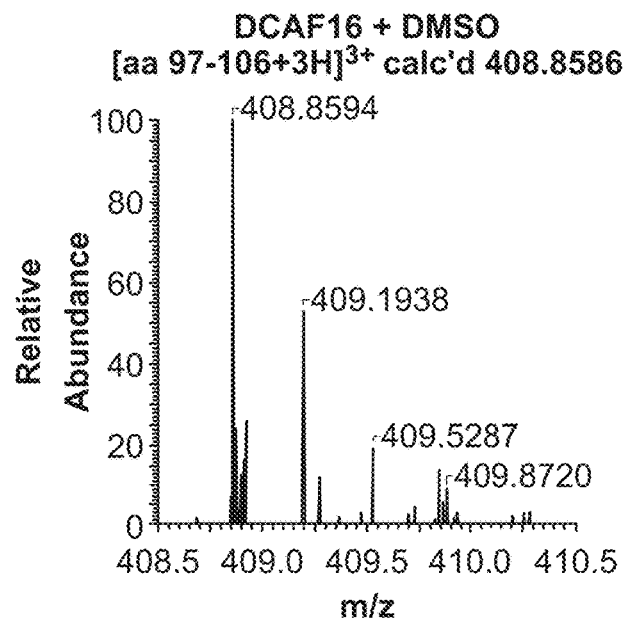
Figure 11C:
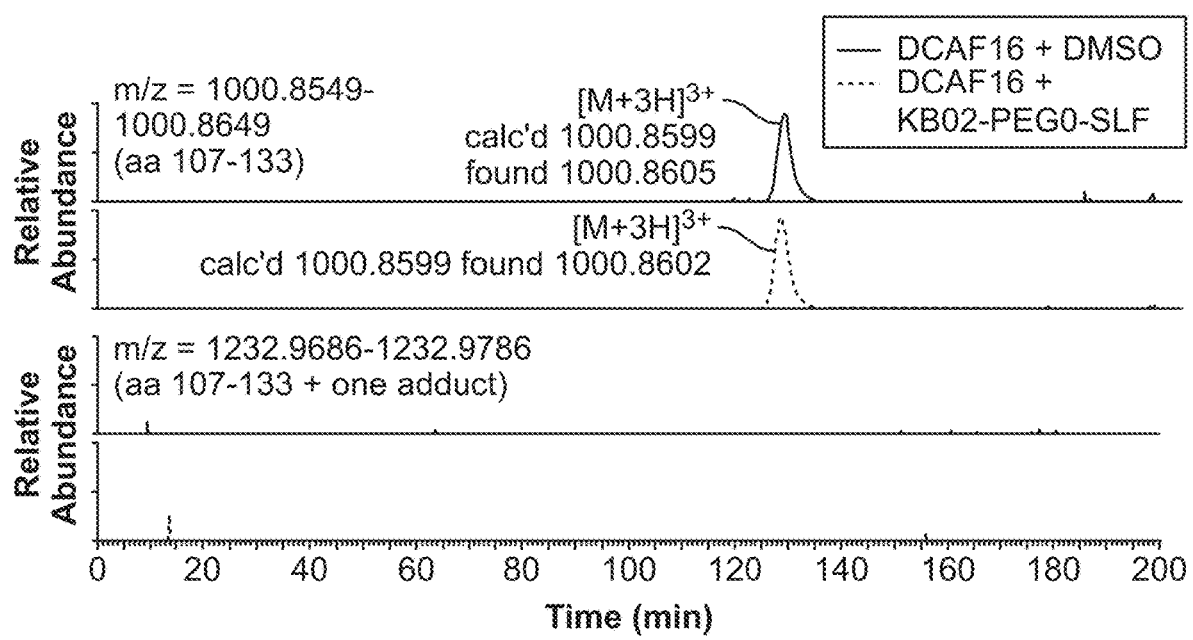
Figure 11C:
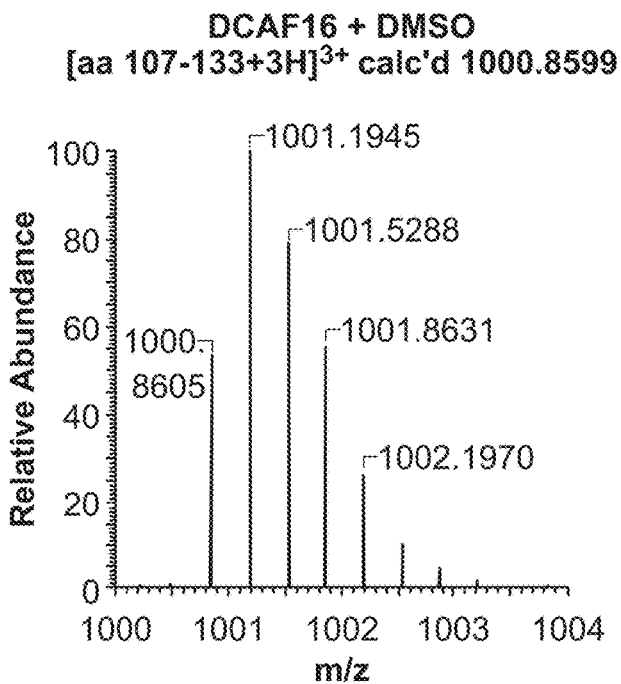
Figure 12A:
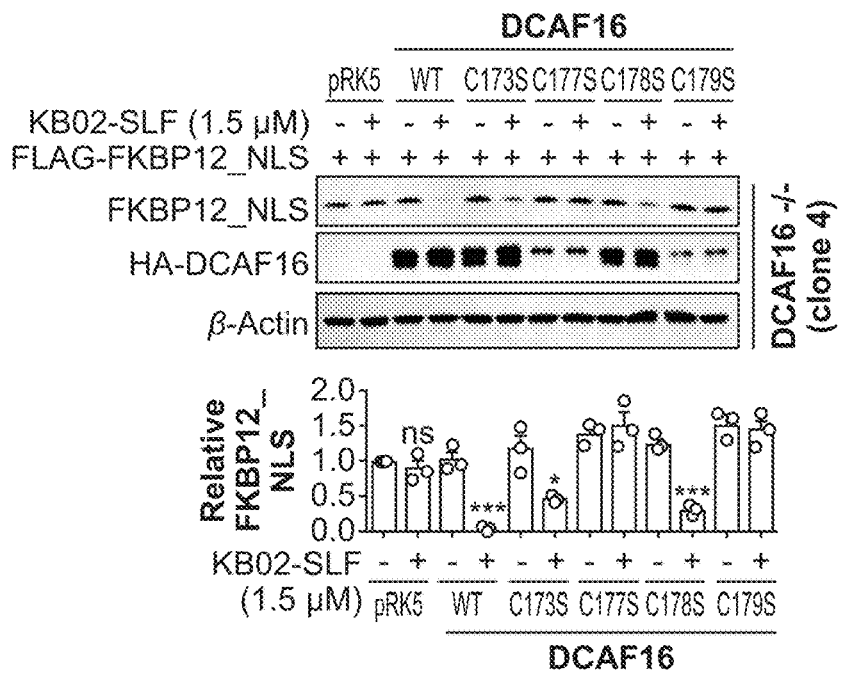
FIG. 12A-FIG. 12C illustrate analysis by site-directed mutagenesis of the contributions of cysteines on the KB02-SLF-modified DCAF16 peptide to KB02-SLF-mediated degradation of FLAG-FKBP12_NLS.
Figure 12B:
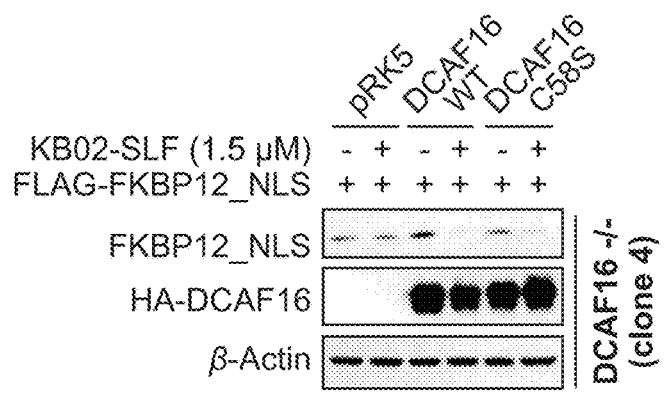
Figure 12C:
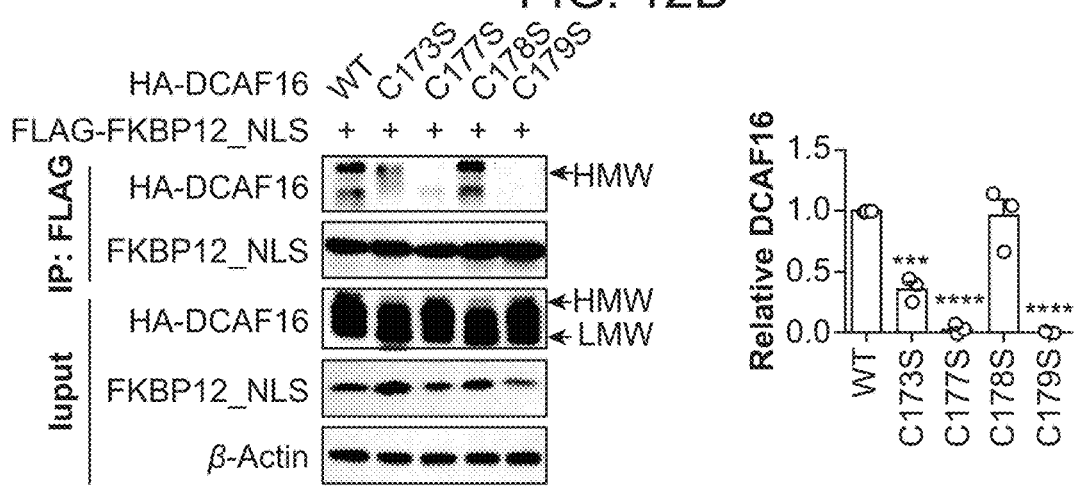

DCAF16 is a 216 aa protein that is highly conserved across mammals (e.g., human and rabbit DCAF16 share 97% identity), but notably absent from rodents. The DCAF16 protein has eight cysteine residues, including a cluster of four cysteines between amino acids 173-179 (FIG. 3E). KB02-PEG0-SLF-reactive cysteine(s) in DCAF16 were mapped by treating HA-DCAF16-transfected HEK293T cells with DMSO or KB02-PEG0-SLF (10 μM, 2 h), affinity purifying HA-DCAF16, and subjecting the protein to trypsin digestion and LC-MS/MS analysis (FIG. 3E). The MS1 (parent ion) profiles were searched for the m/z values of unmodified and KB02-PEG0-SLF-modified DCAF16 tryptic peptides and identified a KB02-PEG0-SLF-modified form of the tryptic peptide (aa 168-184) containing C173 and C177-179 (FIG. 11A). In contrast, KB02-PEG0-SLF-modified forms for tryptic peptides containing C100/C103 (aa 97-106) or C119 (aa 107-133) (FIG. 11B, FIG. 11C) were not identified. No tryptic peptides containing C58 were detected, likely because it is a very small in length (four amino acids). Tandem (MS/MS) analysis of the KB02-PEG0-SLF-modified peptide aa168-184 indicated that the most likely modified residue(s) was C177, C178, and/or C179 (FIG. 3F). The contribution of C177-179 and other cysteine residues to KB02-SLF-induced degradation of FKBP12_NLS to be evaluated by site-directed mutagenesis were hindered, in part, by the dramatic reduction in expression of cysteine-to-serine mutants for multiple cysteine residues (e.g., C177, C179) (FIG. 12A). These mutagenesis studies did reveal that the C58S-, C173S-, and C178S-DCAF16 mutants were expressed at near-wild type levels and supported KB02-SLF-induced degradation of FKBP12_NLS (FIG. 12B), indicating that C58, C173, and C178 are unlikely to constitute primary sites of engagement for KB02-SLF. It was additionally analyzed whether cysteine-to-serine mutants of DCAF16 could form a ternary complex with KB02-SLF and FKBP12_NLS in cells pretreated with the proteasome inhibitor MG132, which was found to normalize DCAF mutant protein expression levels (FIG. 12C). Among the four mutants tested, C173S- and C178S-DCAF16, but not C177S- and C179S-DCAF16, co-immunoprecipitated with FKBP12_NLS in KB02-SLF-treated cells (FIG. 12C).

Example 7: BRD4 Degradation

Figure 3G:
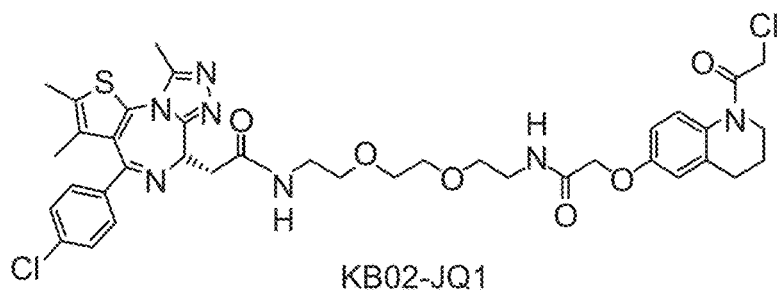
Figure 3H:
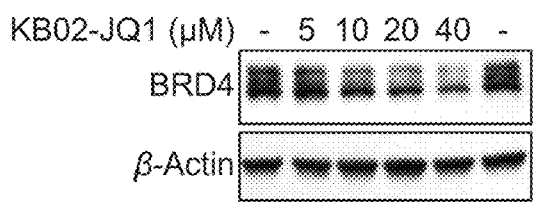
Figure 3H:
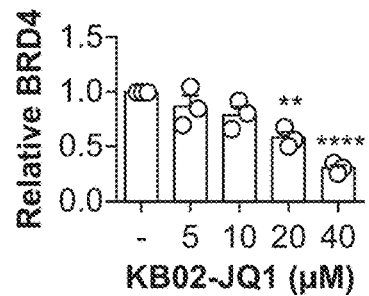
Figure 3I:
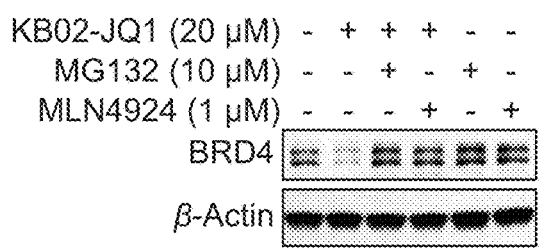
Figure 3J:
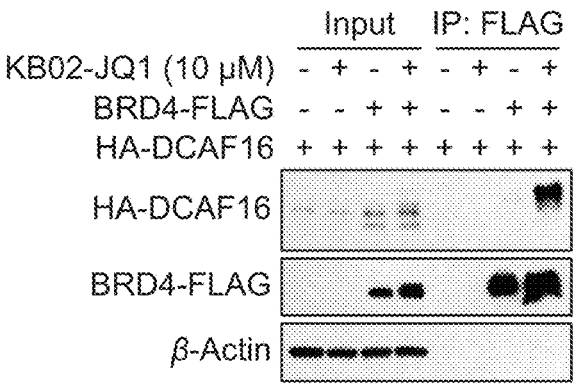
Figure 3K:
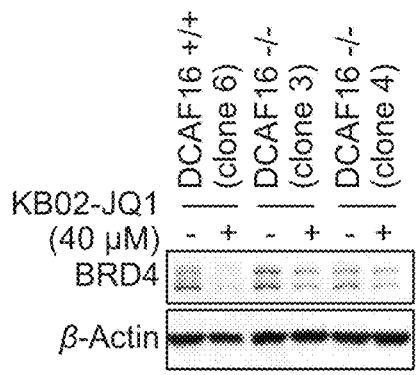
Figure 3K:
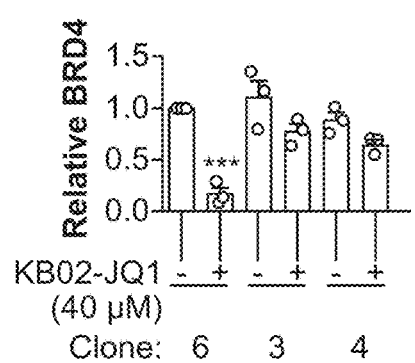
Figure 13:
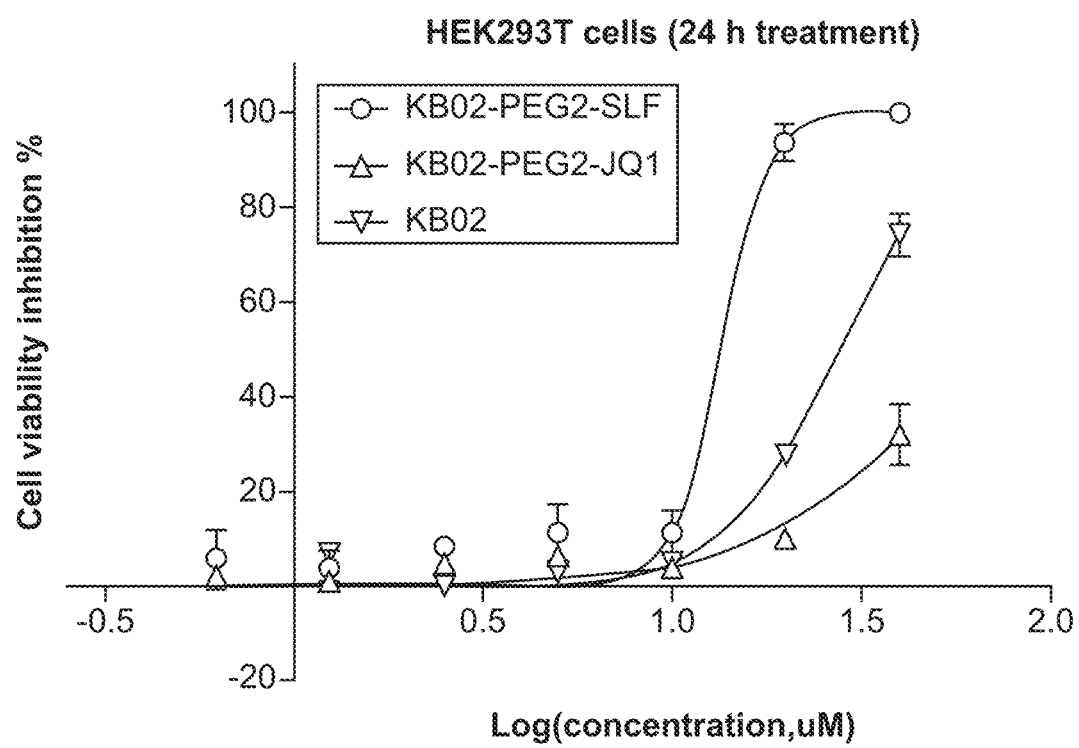
FIG. 13 is a graph representing cell viability of HEK293T cells treated with KB02-SLF, KB02, or KB02-JQ1 for 24 hours. Data represent mean values±SEM for 3 biological replicates.

BRD4 was selected as another nuclear protein for DCAF16 mediated degradation. BRD4 has a potent and selective ligand JQ1 that has been successfully coupled to other E3 ligands to promote degzradation (Winter, G. E. et al. *Science* 348, 1376-1381 (2015); Filippakopoulos, P. et al. *Nature* 468, 1067-1073 (2010); Raina, K. et al. *Proc Natl Acad Sci* 113, 7124-7129 (2016)). The KB02-JQ1 bifunctional compound (FIG. 3G) promoted, in a concentration-dependent manner, the degradation of BRD4 in HEK293T cells (FIG. 3H), and this effect was blocked by MG132 or MLN4924 (FIG. 3I). It was noted that KB02-JQ1 degraded BRD4 at a much higher concentration (20-40 μM) compared to the degradation of FKBP12_NLS by KB02-SLF (0.5-2 μM). It was suspected that this apparent difference in potency may reflect differential cellular uptake of the two KB02 bifunctional compounds, as KB02-JQ1 also showed a rightward shift in cytotoxicity ($IC_{50}$>50 μM) compared to KB02-SLF ($IC_{50}$=14±1.1 μM) and KB02 ($IC_{50}$=23±1.2 μM) (FIG. 13). Supporting a functional role for DCAF16 in KB02-JQ1-induced BRD4 degradation, it was found that DCAF16 co-immunoprecipitated with BRD4 in a KB02-JQ1-dependent manner (FIG. 3J) and that BRD4 degradation was substantially blocked in DCAF16−/− cells (FIG. 3K).

Example 8: Methods for Examples 1-7

Common Reagents and Antibodies

The anti-HA (3724), FLAG (14793), DDB1 (6998), BRD4 (13440S), Lamin A/C (2032), K48-linked polyubiquitin (4289), HRP-linked rabbit IgG (7074) and HRP-linked mouse IgG (7076) antibodies were purchased from Cell Signaling Technology. The anti-FLAG HRP antibody (A8592), anti-FLAG affinity gel (A2220) and anti-HA agarose antibody (A2095) were purchased from Sigma-Aldrich. The anti-β-Actin antibody (sc-47778) was purchased from Santa Cruz Biotechnology. Alexa Fluor 488-conjugated goat anti-mouse IgG (H+L) secondary antibody (A-11001) and Alexa Fluor 568-conjugated goat anti-rabbit IgG (H+L) secondary antibody (A-11011) were purchased from Invitrogen. FuGene 6 (E2692) transfection reagent and sequencing grade modified trypsin (V5111) were purchased from Promega. Enzyme-linked chemiluminescence (ECL) (32106) and ECL plus (32132) western blotting detection reagents were purchased from Thermo Scientific. MG132 (S2619) was purchased from Selleck Chemicals. MLN4924 (15217), SLF (Ser. No. 10/007,974), and JQ1 (11187) were purchased from Cayman Chemical. Polyethylenimine (PEI, MW 40,000, 24765-1) was purchased from Polysciences, Inc. Isotopically-labeled TEV-tags were synthesized as described in Backus et al., "Proteome-wide covalent ligand discovery in native biological systems", *Nature* 534: 570-574 (2016).

Cell Lines

Human Embryonic Kidney (HEK) 239T and MDA-MB-231 cells were obtained from ATCC and cultured in Dulbecco's Modified Eagle Medium (DMEM, Corning) with 10% (v/v) fetal bovine serum (FBS, Omega Scientific) and L-glutamine (2 mM). For SILAC experiments, heavy and light labeled cell lines were cultured in DMEM medium with [$^{13}C_6$, $^{15}N_2$]-L-lysine and [$^{13}C_6$, $^{15}N_4$]-L-arginine (heavy labeled cells, 100 mg/mL each), or L-lysine and L-arginine (light labeled cells, 100 mg/mL each) for five generations. Both heavy and light SILAC medium were also supplemented with 10% (v/v) dialyzed FBS (Gemini), penicillin, streptomycin, and L-glutamine (2 mM). Human Embryonic Kidney (HEK) 239 cells with DCAF16 gRNA CRISPR editing were purchased from Synthego and cultured in DMEM with 10% FBS and L-glutamine (2 mM). All the cell lines were tested negative for mycoplasma contamination.

Cloning and Mutagenesis

Human FKBP1A (FKBP12) cDNA with N-terminal FLAG tag or N-terminal FLAG tag and C-terminal nuclear localization sequence (NLS, PKKKRKV (SEQ ID NO: 5)) was obtained by reverse transcription polymerase chain reaction (RT-PCR) amplification of a cDNA pool extracted from HEK293T cells and subcloned via EcoRI and BamHI sites into pCDH-CMV-MCS-EF1-Puro vector. Human DCAF16 cDNA with N-terminal HA tag was obtained by RT-PCR amplification of a cDNA pool extracted from HEK293T cells and subcloned via SalI and NotI sites into pRK5 vector. Human BRD4 with C-terminal FLAG tag was inserted into pRK5 vector by Gateway cloning technology. The expression vectors for DCAF16 mutants were generated by QuikChange site-directed mutagenesis.

Generation of FLAG-FKBP12 and FLAG-FKBP12_NLS Stably Expressed HEK293T Cell Lines by Lentivirus Transduction FLAG-FKBP12 or FLAG-FKBP12_NLS lentivirus was generated by co-transfection of FLAG-FKBP12 or FLAG-FKBP12_NLS, pCMV-dR8.2 and pMD2.G into HEK 293T cells using FuGene 6 transfection reagent (Promega). Virus-containing medium were collected 48 h after transfection, filtered with 0.45 μM filter, and used to transduce HEK293T and MDA-MB-231 cells in the presence of 10 μg/mL polybrene (Santa Cruz). 72 h after transduction, puromycin (2 μg/mL) was added to cells. HEK293T cells stably expressing FLAG-FKBP12 or FLAG-FKBP12_NLS were obtained after puromycin selection for 7 days. HEK293T cells stably expressing pCDH empty vector were generated in parallel as control.

Generation of DTL and DCAF16 Knockdown in HEK293T Cell Lines shRNA lentivirus was generated by co-transfection of shRNA-containing vector, pCMV-dR8.2 and pMD2.G into HEK 293T cells using FuGene 6 transfection reagent (Promega). Virus-containing medium were collected 48 h after transfection and used to transiently transduce HEK293T cells stably expressing FLAG-FKBP12_NLS for 48 h. Lentiviral shRNAs targeting human DCAF16 or DTL were in pLKO.1 vector and purchased from Sigma. The sequences of shRNAs is described below.

```
shLuc (SHC007, Sigma):
                                    (SEQ ID NO: 6)
CCGGCGCTGAGTACTTCGAAATGTCCTCGAGGACATTTCGAAGTACTCAG

CGTTTTT shDTL_1 (TRCN0000118815, Sigma):
                                    (SEQ ID NO: 7)
CCGGCTGGTGAACTTAAACTTGTTACTCGAGTAACAAGTTTAAGTTCACC

AGTTTTTG shDTL_2 (TRCN0000118813, Sigma):
                                    (SEQ ID NO: 8)
CCGGGCCTAGTAACAGTAACGAGTACTCGAGTACTCGTTACTGTTACTAG

GCTTTTTG shDCAF16_1 (TRCN0000122576, Sigma):
                                    (SEQ ID NO: 9)
CCGGCAAACAGCTAAGCCGAACATTCTCGAGAATGTTCGGCTTAGCTGTTT

GTTTTTG
```

-continued shDCAF16_2 (TRCN0000369937, Sigma):
(SEQ ID NO: 10)
CCGGTCCTGGTTGTATCATGCTAAACTCGAGTTTAGCATGATACAACCAGG
ATTTTTG Generation of CRISPR-Mediated Knockout in HEK293 Cell Lines DCAF16 CRISPR knockout HEK293 cell pools were generated by Synthego using nucleofection of Cas9-gRNA ribonucleoprotein (RNP) complex. Editing efficiency 48 h post nucleofection of cell pool was 88%. HEK293 editing cell pools were subjected to single cell sorting in The Flow Cytometry Core Facility at Scripps Research. Individual cell clone was grown in 96-well plate until the cells were confluent. To confirm the editing in DCAF16 gene, genomic DNAs from each clone were extracted using PureLink Genomic DNA Mini Kit (Invitrogen). DCAF16 gene was amplified by PCR and confirmed by DNA sequencing. Indel analysis was performed using ICE analysis from Synthego.

The sequences of DCAF16 gRNA and sequencing primers is described below.

DCAF16 gRNA:
(SEQ ID NO: 11)
TCTGACAAGTGGTCAGGAGA

DCAF16 sequencing primer (forward): TAT-TCAGGTATGGGAGTGGCTCTA (SEQ ID NO: 12)

DCAF16 sequencing primer (reverse):
(SEQ ID NO: 13)
GCCAGGATTTGAAGGAGATACTCT

To confirm DCAF16 knockout at the protein level, lentivirus containing FLAG-FKBP12_NLS was used to infect three wild type DCAF16 clones (clone 6, 17, 18) and three DCAF16 knockout clones (clone 3, 4, 22). Clone 6 stably expressing FLAG-FKBP12_NLS was grown in heavy SILAC DMEM medium for 5 generations. The other clones stably expressing FLAG-FKBP12_NLS were grown in light SILAC DMEM medium for 5 generations. All 6 clones were treated with 5 µM KB02-SLF and 10 µM MG132 for 2 h. Cells were collected and analyzed for FLAG-FKBP12_NLS associating proteins using the same method described below. Proteins from clone 6 (heavy labeled) were combined with the other clones (light labeled) separately and identified by LC-MS/MS.

Cell Lysis and Western Blot

Cells were collected and lysed in 1% NP-40 lysis buffer (25 mM Tris-HCl pH 7.4, 150 mM NaCl, 10% glycerol, 1% Nonidet P-40) with complete protease inhibitor cocktail (Roche). Cells were vortexed and sonicated for 5 pulses (40%, 4). The supernatant was collected after centrifugation at 16,000 g for 10 min at 4° C. Protein concentration was determined by DC assay (Bio-Rad). Protein lysate was heated at 95° C. for 5 min in 1× Laemmli sample buffer. Proteins were resolved by 12% or 14% Novex Tris-Glycine Mini Gels (Invitrogen) and transferred to polyvinylidene fluoride (PVDF) membrane (0.2 Bio-Rad). The membrane was blocked with 5% BSA in TBST buffer (0.1% Tween 20, 20 mM Tris-HCl 7.6, 150 mM NaCl) at room temperature for 1 h. The antibody was diluted with fresh 5% BSA in TBST buffer (1:10000 dilution for FLAG, HA and β-Actin, 1:1000 dilution for others) and incubated with membrane (1 h room temperature for FLAG, HA and β-Actin, overnight 4° C. for others). Membrane was washed three times with TBST buffer and incubated with secondary antibody (1:5000 dilution in 5% BSA in TBST) at room temperature for 1 h. Membrane was washed three times with TBST buffer. The chemiluminescence signal in membrane was recorded after developing in ECL or ECL plus western blotting detection reagent using CL-XPosure film (Thermo Scientific). Relative band intensities were quantified using ImageJ.

Subcellular Fractionation

HEK293T cells stably expressing FLAG-FKBP12 or FLAG-FKBP12_NLS were harvested. Cell pellets were re-suspended in subcellular fraction buffer (250 mM Sucrose, 20 mM HEPES, pH 7.4, 10 mM KCl, 1.5 mM $MgCl_2$, 1 mM EDTA, 1 mM EGTA, 1 mM DTT, protease inhibitor cocktail) and homogenized on ice by 20 passes through a 25-gauge syringe needle. The pellets after centrifugation (720 g, 5 min) were homogenized on ice by 10 passes through a 25-gauge syringe needle. Nuclear fraction was collected as the pellets after centrifuging at 720 g for 5 min. The supernatant was ultracentrifuged at 100,000 g for 1 h. The resulting supernatant was the cytosol fraction. Equivalent portions of the cytosol and nuclear fractions were then subjected to Western blot analyses.

Immunoprecipitations

Cells were collected and lysed in 1% NP-40 lysis buffer with complete protease inhibitor cocktail on ice for 10 min, followed by 5 pulses of sonication (40%, 4). After centrifugation at 16,000 g for 10 min at 4° C., the supernatant was collected. FLAG affinity gel (20 µL slurry per sample) was incubated with protein lysates at 4° C. for 1 h and washed four times with IP washing buffer. The affinity gel was heated at 95° C. for 10 min in 2× Laemmli sample buffer, followed by western blot analysis.

Identification of FLAG-FKBP12_NLS Interacting Proteins

HEK293T light and heavy SILAC cells that stably express FLAG-FKBP12_NLS were treated with DMSO and 5 µM KB02-SLF for 2 h respectively, in the presence of 10 µM MG132. Heavy and light cells were collected and lysed in 1% NP-40 lysis buffer with complete protease inhibitor cocktail. FLAG immunoprecipitation (20 µL slurry per sample) was performed with 2 mg of total protein lysates to enrich FLAG-FKBP12_NLS from light and heavy cell lysates. After washing the FLAG resin four times with IP washing buffer (0.2% NP-40, 25 mM Tris-HCl pH 7.4, 150 mM NaCl), FLAG resin from light and heavy samples were combined and washed once with PBS. FLAG-FKBP12_NLS and its associating proteins were eluted by heating at 65° C. for 10 min with 8M urea in PBS, then reduced with 12.5 mM DTT at 65° C. for 15 min and alkylated with 25 mM iodoacetamide at 37° C. for 30 min. The protein solution was diluted with PBS to 2M urea and digested with 2 µg trypsin at 37° C. for 6 h. Tryptic peptides were acidified with 5% formic acid and loaded onto a silica capillary column (250 µm) packed with 3 cm of C18 resin (Aqua 5 µm, Phenomenex). Peptides were analyzed on LTQ-Orbitrap Elite mass spectrometer (Thermo Scientific) coupled with Thermo UltiMate 3000 UHPLC system. Peptides were separated on a capillary column packed with 3 cm of strong cation exchange (SCX) resin (Luna 5 µm, Phenomenex), 10 cm of C18 resin (Aqua 5 Phenomenex) and a 5 µm tip. A five-step MudPIT method was used to analyze the peptides as previously described.

isoTOP-ABPP

HEK293T cells were treated with DMSO or 10 µM KB02-SLF for 2 h. Cells were collected and subjected to isoTOP-ABPP sample preparation using the same protocol as described in Backus et al., "Proteome-wide covalent ligand discovery in native biological systems", *Nature* 534: 570-574 (2016).

Proteome-Wide Identification of KB02-JQ1-Induced Protein Degradation

HEK293T light and heavy SILAC cells were treated with DMSO and 5 μM of KB02-JQ1 for 24 h respectively. Light and heavy cells were collected and lysed in 1% NP-40 lysis buffer with complete protease inhibitor cocktail. Cells were vortexed and sonicated for 5 pulses (40%, 4). The supernatant was collected after centrifugation at 16,000 g for 10 min at 4° C. Protein concentration was determined by DC assay. 50 μg proteome from light and heavy samples were mixed, followed by methanol/chloroform precipitation. Protein pellets were heated at 65° C. for 10 min with 8M urea in PBS, then reduced with 12.5 mM DTT at 65° C. for 15 min and alkylated with 25 mM iodoacetamide at 37° C. for 30 min. The protein solution was diluted with PBS to 2M urea and digested with 2 μg trypsin at 37° C. for 6 h. Tryptic peptides were acidified with 5% formic acid. 5 peptides were loaded onto a silica capillary column (250 μm) packed with 3 cm of C18 resin. The same MudPIT method and CIMAGE software as described above were used to analyze the peptides.

Immunofluorescence

Cells were seeded and grown in 35 mm glass bottom dish (MatTek). After compound treatment, cells were rinsed twice with PBS and fixed in 1 mL of 4% paraformaldehyde (v/v in PBS) for 15 min at room temperature. The fixed cells were rinsed twice with PBS, permeabilized and blocked with 0.1% Triton X-100 (v/v in 5% BSA in PBS) for 30 min at room temperature. The cells were incubated overnight (14 h) at 4° C. with FLAG or HA antibody at 1/100 dilution (in 0.1% Triton X-100/5% BSA in PBS). Cells were washed with 0.1% Triton X (in PBS) three times and incubated with Alexa Fluor 488-conjugated goat anti-mouse IgG (H+L) secondary antibody (for FLAG tag) or Alexa Fluor 568-conjugated goat anti-rabbit IgG (H+L) secondary antibody (for HA tag) at 1/1000 dilution (in 0.1% Triton X-100/5% BSA in PBS) at room temperature in dark for 1 h. Cells were washed with 0.1% Triton X (in PBS) three times and mounted with ProLong Gold Antifade Mountant with DAPI (Invitrogen). Cells were imaged with Zeiss LSM780 in The Core Microscopy Facility at Scripps Research. Images were processed in ImageJ software. To quantify the degree of nucleus-localized fluorescence signal, background was subtracted, then the nuclear and whole cell area were selected and quantified for each cell examined. Relative nucleus with respect to whole cell fluorescence intensity was presented.

Cell Viability Assay

HEK293T cells were seeded in 96-well clear bottom white plate (Corning) at 3×10⁴ cells per well in 100 μL of DMEM medium and grown for 24 h. The cells were treated with 0.625, 1.25, 2.5, 5, 10, 20 and 40 μM of KB02-SLF or KB02-JQ1 (DMSO stock, final DMEM concentration is 0.1% (v/v)) in 100 μL of DMEM medium for 24 h. 50 μL of Cell Titer Glo reagent (Promega) was added to each well and incubate for 10 min at room temperature. The luminescence was read on CLARIOstar (BMG LAB TECH).

qPCR Analysis

Total RNA was extracted from the cells using RNeasy Mini Kit (Qiagen). cDNA was synthesized using iScript Reverse Transcription Supermix (Bio-Rad). Amplification of DCAF16, DTL and GAPDH genes was performed using SYBR Select Master Mix (Applied Biosystems) on an ABI Real Time PCR System (Applied Biosystems). The sequences of qPCR primers are described below. Relative DCAF16 and DTL gene expression was normalized to the GAPDH gene.

```
GAPDH primer (forward):
                                (SEQ ID NO: 14)
CTGGGCTACACTGAGCACC GAPDH primer (reverse):
                                (SEQ ID NO: 15)
AAGTGGTCGTTGAGGGCAATG DCAF16 primer (forward):
                                (SEQ ID NO: 16)
AGTCTTGCCTGGCAGGTTAAG DCAF16 primer (reverse):
                                (SEQ ID NO: 17)
GGGACTTGTAAGAGGCTTTTGAA DTL primer (forward):
                                (SEQ ID NO: 18)
TCACTGGAATGCCGTCTTTGA DTL primer (reverse):
                                (SEQ ID NO: 19)
CTCACCAGCTTTTACGTCCC
```

LC-MS/MS Detection of KB02-PEG0-SLF-Modified Tryptic Peptides on DCAF16

HEK293T cells were transfected with HA-DCAF16 plasmid by PEI transfection reagent for 24 h and treated with DMSO or 10 μM KB02-PEG0-SLF for 2 h. Cells were collected and lysed in 1% NP-40 lysis buffer with complete protease inhibitor cocktail. HA immunoprecipitation was performed with 10 mg of total protein lysates to purify HA-DCAF16. After washing the HA resin three times with IP washing buffer and once with PBS, HA-DCAF16 protein was eluted by heating at 65° C. for 10 min with 8M urea in PBS, then reduced with 12.5 mM DTT at 65° C. for 15 min and alkylated with 25 mM iodoacetamide at 37° C. for 30 min. The protein solution was diluted with PBS to 2M urea and digested with 2 μg trypsin at 37° C. for 6 h. Tryptic peptides were acidified with 5% formic acid and loaded onto a silica capillary column (250 μm) packed with 3 cm of C18 resin (Aqua 5 Phenomenex). Peptides were analyzed on LTQ-Orbitrap Elite mass spectrometer (Thermo Scientific) coupled with a Thermo UltiMate 3000 UHPLC system. Peptides were separated on a capillary column packed with 10 cm of C18 resin (Aqua 5 Phenomenex) and a 5 μm tip. The flow rate was 0.5 μL/min. The gradient was 5% acetonitrile with 0.1% formic acid from 0-15 min, 5-30% acetonitrile with 0.1% formic acid from 15-149 min, 30-95% acetonitrile with 0.1% formic acid from 149-179 min, 95-5% acetonitrile with 0.1% formic acid from 179-180 min and 5% acetonitrile with 0.1% formic acid from 180-200 min. MS parameters were set as previously described. The raw data was acquired in Xcalibur operation software.

Statistical Analysis

Quantitative data were expressed in scatter plots with mean±SEM (standard error of the mean, shown as error bar) shown. Differences between two groups were examined using unpaired two-tailed Student's t test. The P values were indicated ($*P<0.05$, $P<0.01$, $*P<0.001$ and $****P<0.0001$). P values<0.05 were considered statistically significant.

Example 9: Quantitative Activity-Based Protein Profiling (ABPP)

HEK293T cells were treated with DMSO (four biological replicates), 2 μM KB02-SLF (three biological replicates) or 20 µM KB02-JQ1 (three biological replicates) for 1.5 h (ten samples in total). Cells were collected, washed once with PBS and lysed in PBS by sonication (40%, 4, 20 pulses). Samples were clarified by centrifugation for 10 min at 8,000 g. Lysate was adjusted to 1.0 mg/mL in 500 µL. Samples were labeled with 100 µM iodoacetamide alkyne (5 µL of 10 mM stock in DMSO) at room temperature for 1 hour, conjugated by CuACC to desthiobiotin azide (10 µL of 5 mM stock in DMSO, final concentration=100 tris(2-carboxyethyl)phosphine hydrochloride (TCEP, 10 µL of 50 mM stock in H2O, final concentration=1 mM), TBTA (30 µL of 1.7 mM stock in 4:1 tBuOH:DMSO, final concentration=100 µM) and $CuSO_4$ (10 µL of 50 mM stock in H2O, final concentration=1 mM). The samples were allowed to react for 1 hour at room temperature. Proteins were precipitated by adding 3.5 mL of $H_2O$, 4 mL of methanol and 1.5 mL of chloroform, followed by centrifugation at 5,000 g for 15 min (4° C.). After aspirating the top layer, the protein pellets with bottom layer were washed with 8 mL cold methanol by centrifugation at 5,000 g for 15 min (4° C.). Protein pellets were resuspended in 90 µL of buffer containing 9 M urea, 10 mM DTT and 50 mM tetramethylammonium bicarbonate (pH 8.5), sonicated (40%, 4, 5 pulses) and heated at 65° C. for 20 min. Samples were cooled to room temperature and alkylated with 50 mM iodoacetamide (10 µL of 500 mM stock in H2O) at 37° C. for 30 minutes. Samples were diluted with 350 µL of 50 mM tetramethylammonium bicarbonate (pH 8.5) and digested with 2 µg trypsin at 37° C. for 4 hours. 40 µL of streptavidin-agarose beads slurry was washed in immunoprecipitation (IP) washing buffer and added to each sample. Beads with peptide samples were rotated for 1 hour at room temperature, filtered off by micro Bio-Spin chromatography column (Bio-Rad) and washed with 1 mL of IP washing buffer (three times), 1 mL of PBS (three times) and 1 mL of $H_2O$. Peptides were eluted by adding 300 µL of 50% acetonitrile with 0.1% of formic acid and dried in vacuum concentrator.

Peptides were resuspended in 100 µL of 30% acetonitrile in 200 mM EPPS (pH 8) and labeled with TMT10plex isobaric reagent following the manufacturer's instructions. 0.15% of hydroxylamine (3 µL of 5% stock in $H_2O$) was added to each sample to quench the reaction (incubate for 15 minutes). After adding 5 µL of formic acid to each sample, 10 peptide samples were combined and dried in vacuum concentrator. Peptides were further fractionated into 21 fractions using Pierce high pH reversed-phase peptide fractionation kit following the manufacturer's instructions. The 21 resulting fractions were pooled into 7 fractions by combining every 7th fraction (e.g. fraction 1, 8 and 15, fraction 2, 9 and 16, etc.) for subsequent mass spectrometry analysis.

The samples were analyzed in Orbitrap Fusion Tribrid mass spectrometer (Thermo Scientific) coupled to UltiMate 3000 HPLC system (Thermo Scientific). Peptides were separated on a capillary column packed with 30 cm of C18 resin (ACQUITY UPLC BEH, 1.7 µm, Waters) and a 5 µm tip. The $MS^1$ scan parameters were set up as follows: 1) Orbitrap resolution: 120,000, 2) Scan range: m/z 400-1700, 3) RF lens (%): 60, 4) AGC target: 2×105, 5) Maximum injection time: 50 ms. The $MS^2$ data were acquired in the ion trap with the following parameter settings: 1) CID collision energy (%): 35, 2) AGC target: 1.8×104, 3) Maximum injection time: 120 ms, 4) Activation Q: 0.25. The $MS^3$ data were acquired in the Orbitrap with the following parameter settings: 1) Orbitrap resolution: 50,000, 2) Number of SPS precursors: 10, 3) First mass: m/z 100, 4) HCD collision energy (%): 55, 5) AGC target: 1.5×105, 6) maximum injection time: 120 ms. The raw data was acquired in Xcalibur operation software.

The $MS^2$ and $MS^3$ spectra data were extracted and analyzed in IP2 Integrated Proteomics Pipeline. In this method mass spectrometry raw files were searched against a reverse-concatenated, nonredundant (gene-centric) database of the human proteome (Uniprot release—Nov. 5, 2012) and filtered using DTASelect 2.0 within the Scripps Goldfish Integrated Proteomics Pipeline (IP2) software. All cysteine residues were specified with a static modification for carbamidomethylation (+57.0215 Da) and one oxidized methionine residue per peptide, if found, was allowed as a variable oxidation (+15.9949 Da). Peptides were required to have at least one tryptic terminus. The precursor ion mass tolerance for a minimum envelope of three isotopic peaks was set to 50 ppm, the minimum peptide length was six residues, the false-positive rate was set at 1% or lower and at least 2 peptides of a protein must be detected in order to be advanced to the next step of analysis. $MS^2$ spectra were searched using an algorithm, ProLuCID, which was published by Xu, et al., in an article titled "ProLuCID: An improved SEQUEST-like algorithm with enhanced sensitivity and specificity" (Journal of Proteomics, Volume 129, 3 Nov. 2015, Pages 16-24) and a reverse concatenated, nonredundant variant of the Human UniProt database (release-2012_11). Cysteine residues were searched with a static modification for carboxyamidomethylation (+57.02146) and up to four differential modification for desthiobiotin-IA (+494.3207). Lysine residues and peptide N-termini were searched with a static modification for TMT-tag labeling (+229.162932). Methionine residues were searched up to four differential modification for oxidation (+15.9949). MS3 quantification was performed using 10plex TMT analysis parameters (m/z 126.127726, 127.124761, 127.131081, 128.128116, 128.134436, 129.131471, 129.13779, 130.134825, 130.141145 and 131.13818) with the mass tolerance of 30 ppm.

Figure 14A:
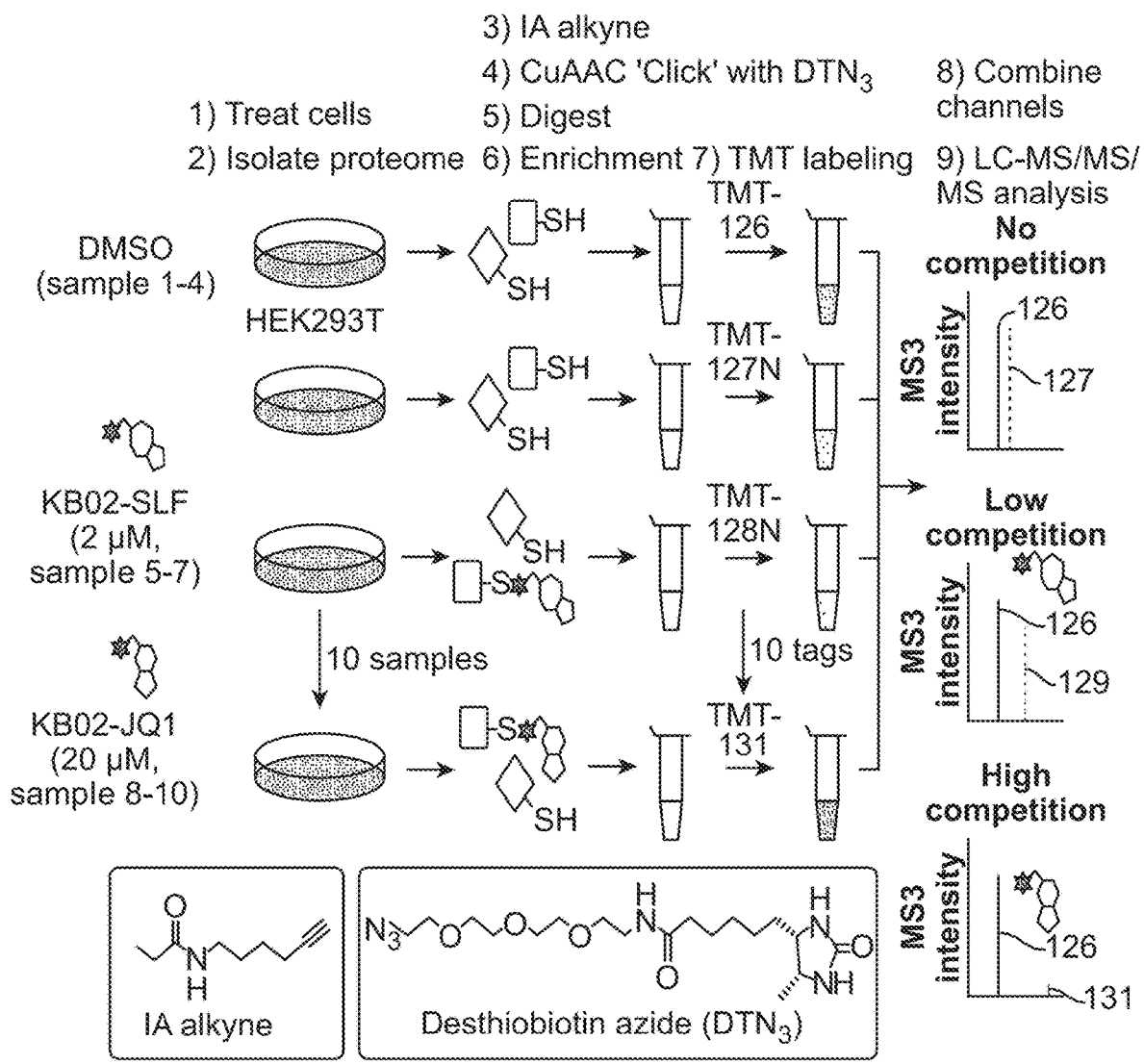
FIG. 14A-FIG. 14C represent a competitive activity-based protein profiling (ABPP) analysis of the fractional engagement of cysteines in DCAF16 by KB02-SLF and KB02-JQ1.
Figure 14B:
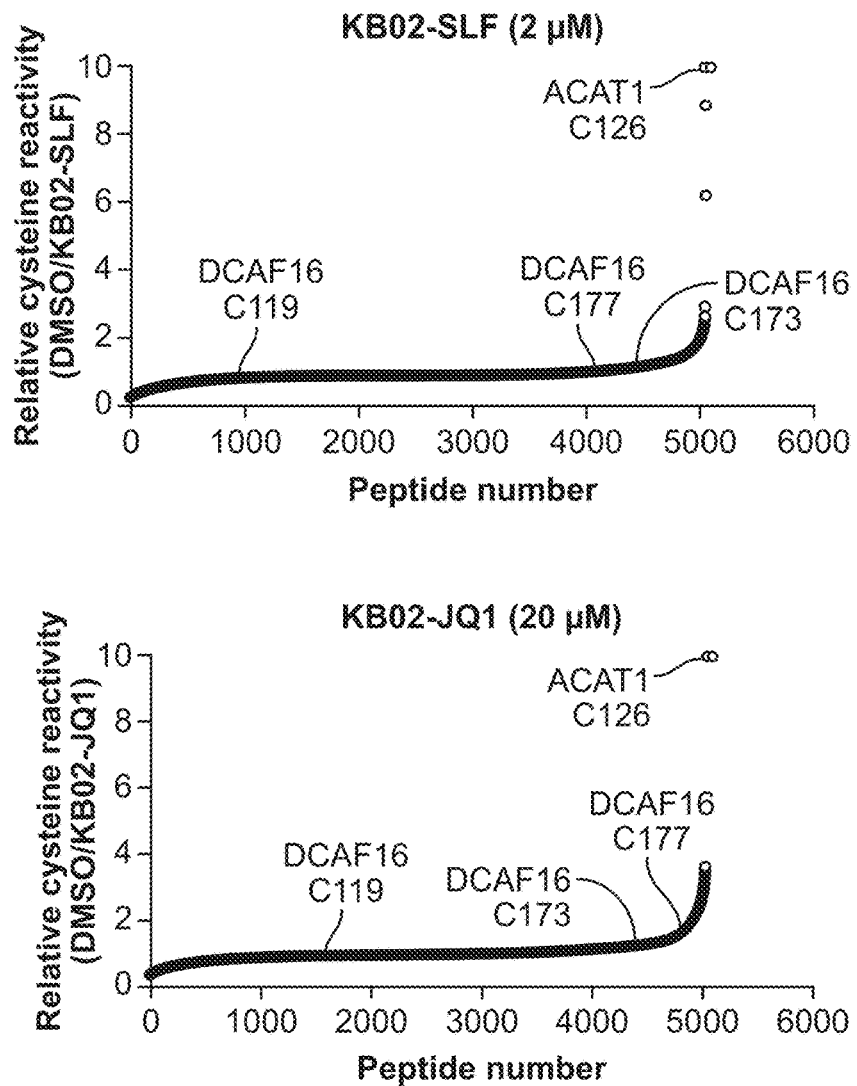
Figure 14C:
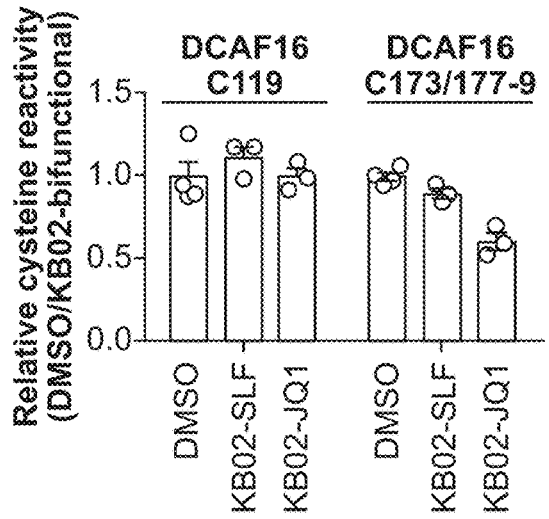

Results:

The relative cellular engagement of DCAF16 by KB02-JQ1 and KB02-SLF was measured. Specifically, competitive ABPP was used to quantitatively map the fractional blockade of IA-alkyne-modified cysteines on endogenously expressed DCAF16 in HEK293T cells treated with concentrations of KB02-SLF (2 µM) or KB02-JQ1 (20 µM) that support FKBP12 and BRD4 degradation, respectively. These chemical proteomic data revealed that KB02-SLF and KB02-JQ1 produced ~10% and 40% engagement, respectively, of the DCAF16 peptide (aa 168-184) containing cysteines 173 and 177-179 (FIG. 14). Another IA-alkyne-reactive cysteine, C119, showed no evidence of engagement in these chemical proteomic experiments (FIG. 14). These data indicate that differential amounts of DCAF16 engagement are required to support FKBP12 and BRD4 degradation by their respective electrophilic PROTACs, but in neither case is a>50% fraction of DCAF16 diverted to a PROTAC-modified state.

Example 10: Proteome-Wide Identification of KB02-JQ1- or KB02-SLF-Induced Protein Degradation HEK293T light and heavy SILAC cells were treated with DMSO and KB02-JQ1 (20 µM) or KB02-SLF (2 µM) for 24 hours, respectively. Light and heavy cells were collected and lysed in 1% NP-40 lysis buffer with complete protease inhibitor cocktail. Cells were vortexed and sonicated for 5 pulses (40%, 4). The supernatant was collected after centrifugation at 16,000 g for 10 min at 4° C. Protein concentration was determined by DC assay. 50 μg proteome from light and heavy samples were mixed, followed by methanol/chloroform precipitation. Protein pellets were heated at 65° C. for 10 minutes with 8 M urea in PBS, then reduced with 12.5 mM DTT at 65° C. for 15 minutes and alkylated with 25 mM iodoacetamide at 37° C. for 30 minutes. The protein solution was diluted with PBS to 2 M urea and digested with 2 μg trypsin at 37° C. for 6 hours. Tryptic peptides were acidified with 5% formic acid. 5 μg peptides were loaded onto a silica capillary column (250 μm) packed with 3 cm of C18 resin. A five-step MudPIT protocol was used in which 0%, 25%, 50%, 80% and 100% salt bumps of ammonium acetate ($NH_4OAc$; 500 mM) were used to elute peptides stepwise from the SCX to the C18 resin followed by an increasing gradient of acetonitrile in each step (5%-100% buffer B in buffer A; buffer A: 95% H2O, 5% acetonitrile, 0.1% formic acid; buffer B: 5% H2O, 95% acetonitrile, 0.1% formic acid). The flow rate through the column was 0.25 μl/min and the voltage applied to the nano-LC electrospray ionization source was 2.5 kV. Spectra were collected in a data-dependent acquisition mode such that each scan cycle involved a single high-resolution full MS spectrum of parent ions (MS1 scan from 400-1800 m/z) collected in the orbitrap coupled to 30 CID-induced fragmentation (MS2) scans in the ion trap of the 30 most abundant parent ions from the MS1 scan. Dynamic exclusion (repeat count of 1, exclusion duration of 20 s). Parent ions with unassigned or +1 charge states by the instrument were excluded for fragmentation. For CIMAGE analysis, MS1 ion chromatograms (±10 ppm error tolerance of predicted m/z) were extracted from both 'light' and 'heavy' target peptide masses (m/z) that were generated using a retention time window (±10 min) centered on the time when the peptide ion was selected for MS/MS fragmentation, and subsequently identified. Next, the ratio of the peak areas under the light and heavy signals (signal-to-noise ratio>2.5) was calculated. Computational filters used to ensure that the correct peak-pair was used for quantification include a co-elution correlation score filter (R2≥0.8), removing target peptides with bad co-elution profile, and an 'envelope correlation score' filter (R2>0.8) that eliminates target peptides whose predicted pattern of the isotopic envelope distribution does not match the experimentally observed high-resolution MS1 spectrum. In addition, peptides detected as 'singletons,' where only the heavy ion of a peptide pair was identified, but that cleared all other filtering parameters, were given a default assigned ratio of '20,' which is defined as any measured ratio that is ≥20 and is the maximum ratio reported here." The median SILAC ratios from quantified peptides were used as measures of protein abundance. The following quality filters were further applied to generate the plot: (1) proteins must have at least two quantified peptides; (2) proteins must be present in both replicates; (3) for each protein, the standard deviation of measured ratios of peptides must be <1.0.

Figure 15:
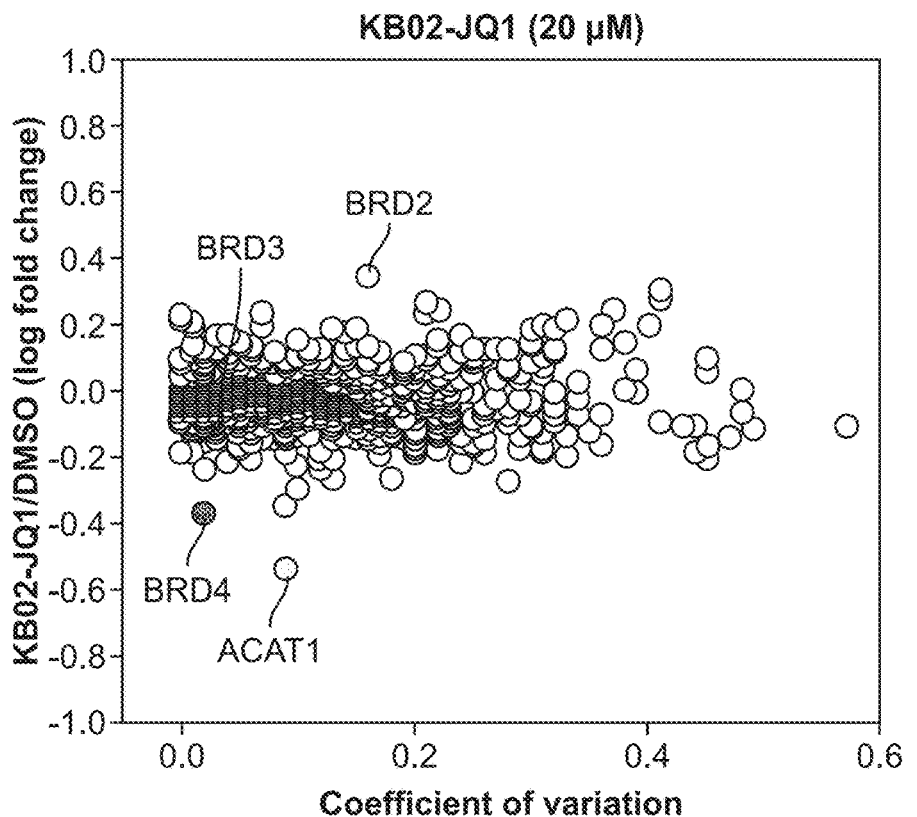
FIG. 15 shows log 10 fold-change in protein abundance between heavy- and light-isotopically labeled HEK293T cells treated with, in the top plot, KB02-JQ1 (20 μM, heavy), and in the bottom plot KB02-SLF (2 μM, heavy), or DMSO (light), for 24 hours. The y-axis and x-axis correspond to the average relative log 10 abundance (KB02-JQ1/DMSO or KB02-SLF/DMSO) and coefficient of variation, respectively, from two experiments (n=2 biologically independent experiments). The average relative log 10 abundance of each protein is normalized to the average log 10 abundance of proteins in control DMSO/DMSO samples (to account for slight deviations in heavy isotope incorporation).
Figure 15:
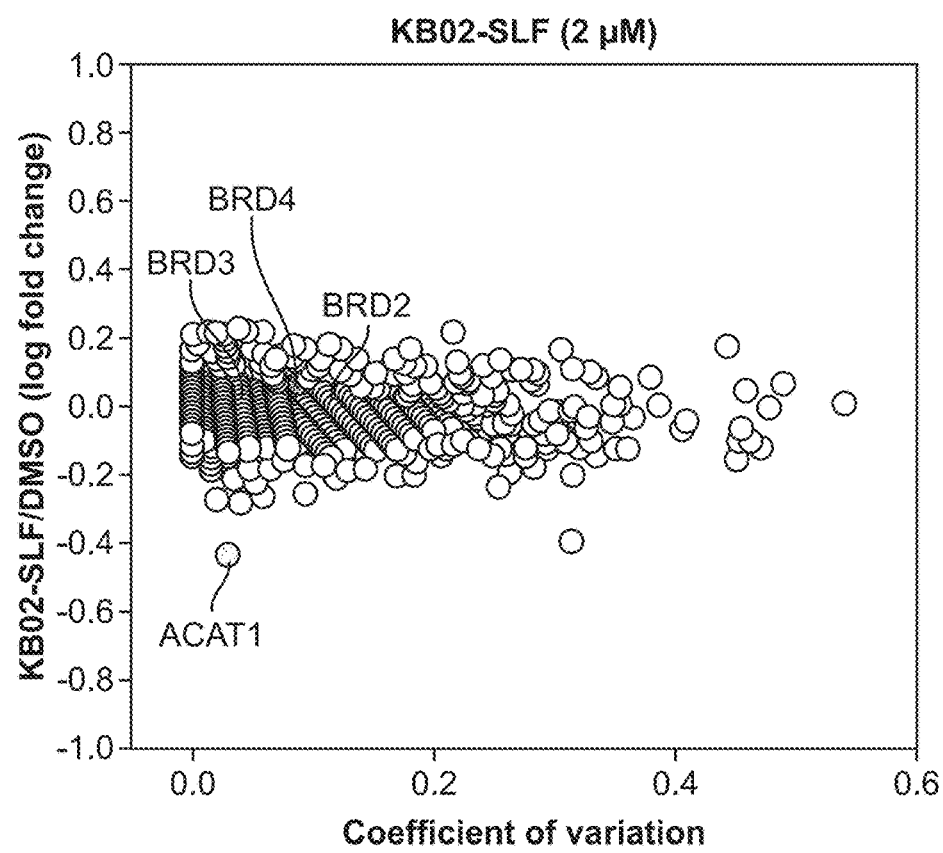

Results:

MS-based proteomic analysis of KB02-JQ1-treated HEK293T cells revealed selective degradation of BRD4, but not BRD2 or BRD3 (FIG. 15). BRD2 appeared to be stabilized by KB02-JQ1, as has been found for JQ1 itself. One additional protein across the proteome—ACAT1—displayed substantially decreased abundance in KB02-JQ1-treated cells (FIG. 15). Control cells treated with KB02-SLF also showed reductions in ACAT1, but not BRD4 (FIG. 15). Interestingly, ACAT1 harbors a highly reactive cysteine (C126) that was fully engaged by KB02-JQ1 or KB02-SLF in HEK293T cells (FIG. 14). These data suggest that covalent modification of C126 by KB02-containing compounds could lead to the degradation of ACAT1, possibly by disrupting homo-oligomeric forms of the enzyme.

Example 11: Compounds Synthesis

Synthesis of Lenalidomide-SLF

Scheme 1. Synthesis of lenalidomie-SLF

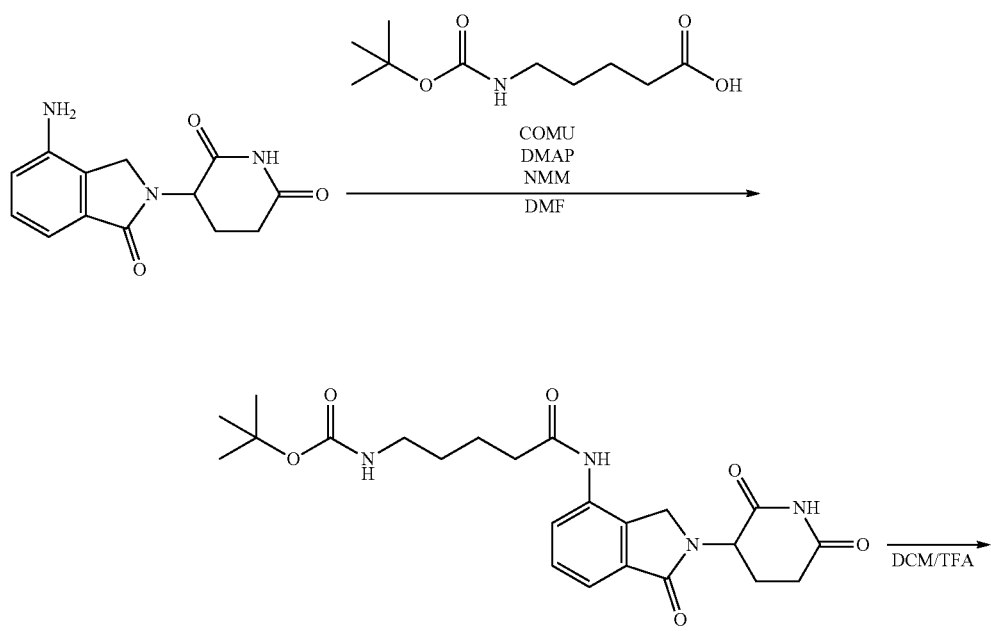

SI-1

-continued

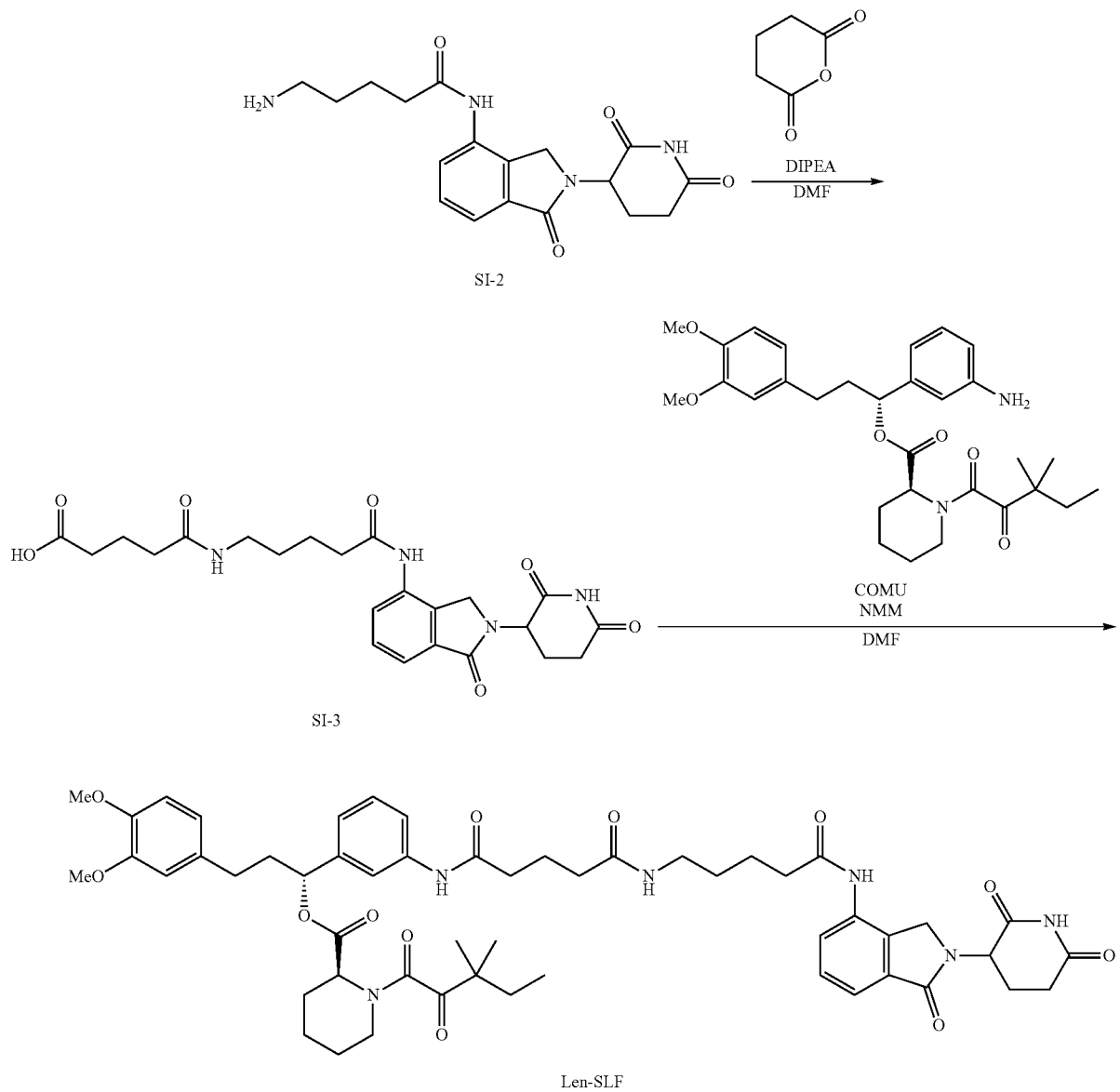

SI-2

SI-3

Len-SLF tert-butyl (5-((2-(2,6-dioxopiperidin-3-yl)-1-oxoisoindolin-4-yl)amino)-5-oxopentyl)carbamate (SI-1)

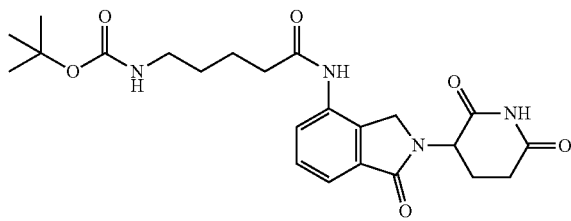 [SMILES: CC(C)(C)OC(=O)NCCCCC(=O)Nc1cccc2c1CN(C1CCC(=O)NC1=O)C2=O]

5-((tert-butoxycarbonyl)amino)pentanoic acid (823 mg, 0.37 mmol, 1 eq.), COMU (1.54 g, 0.36 mmol, 0.95 eq.), and N-methylmorpholine (840 μL, 7.6 mmol, 2 eq.) were dissolved in 4 mL of DMF and incubated for 1 min. Lenalidomide (648 mg, 2.5 mmol, 0.66 eq.) and catalytic 4-dimethylaminopyridine were added in 6 mL of DMF and the reaction was stirred at room temperature for 2 h. The reaction mixture was diluted with ethyl acetate (20 mL), washed with 1N HCl (30 mL), water (30 mL), and brine (30 mL). The organic layer was dried over anhydrous $MgSO_4$ and filtered. This solution was left overnight at 4° C. after which a white precipitate was found. The precipitate was filtered and dried to provide the title compound as a white amorphous solid (860 mg, 75%). 1H NMR (600 MHz, DMSO-d6) δ 11.02 (s, 1H), 9.76 (s, $^1$H), 7.81 (dd, J=7.4, 1.6 Hz, 1H), 7.54-7.40 (m, 2H), 6.81 (t, J=5.7 Hz, 1H), 5.14 (dd, J=13.3, 5.1 Hz, 1H), 4.38 (d, J=17.4 Hz, 1H), 4.34 (d, J=17.4 Hz, 1H), 2.97-2.89 (m, 3H), 2.61 (dt, J=17.3, 3.3 Hz, 1H), 2.35 (t, J=7.3 Hz, 3H), 2.03 (dtd, J=12.5, 5.1, 2.2 Hz, 1H), 1.58 (p, J=7.5 Hz, 2H), 1.42 (p, J=7.2 Hz, 2H), 1.37 (s, 9H). HRMS (ESI) [M+Na]$^+$ for $C_{23}H_{30}N_4O_6Na$ 481.2057, found 481.2063.

5-amino-N-(2-(2,6-dioxopiperidin-3-yl)-1-oxoisoindolin-4-yl)pentanamide (SI-2)

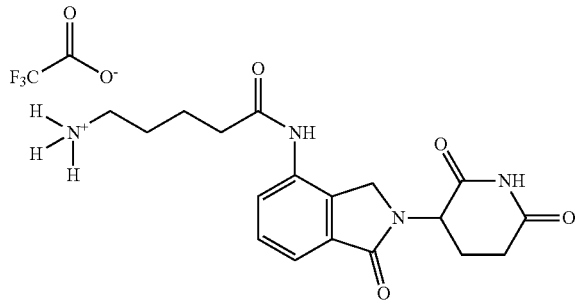 [SMILES: O=C([O-])C(F)(F)F ; [NH3+]CCCCC(=O)Nc1cccc2c1CN(C1CCC(=O)NC1=O)C2=O]

2 mL of dichloromethane, 2 mL of trifluoroacetic acid and 40 µL of H2O was added to SI-1 (500 mg). The reaction was stirred at room temperature for 2 h and monitored by TLC. The solvent was removed and the resulting powder was dried under vacuum overnight to provide the title compound as the TFA salt and used for the next step without purification.

5-((5-((2-(2,6-dioxopiperidin-3-yl)-1-oxoisoindolin-4-yl)amino)-5-oxopentyl)amino)-5-oxopentanoic Acid (SI-3)

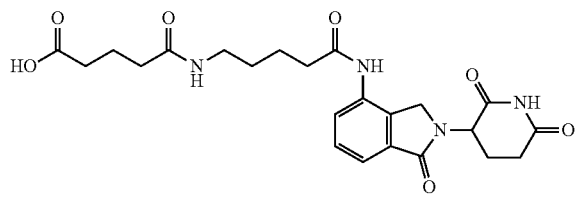 [SMILES: O=C(O)CCCC(=O)NCCCCC(=O)Nc1cccc2c1CN(C1CCC(=O)NC1=O)C2=O]

SI-2 (118 mg, 0.25 mmol, 1 eq.), glutaric anhydride (31 mg, 0.27 mmol, 1.1 eq.) and N,N-diisopropylethylamine (97 mg, 0.75 mmol, 3 eq.) were dissolved in 0.5 mL DMF and stirred at room temperature for 4 h. Upon completion, the reaction was diluted to 1 mL with water/acetonitrile/formic acid (50/50/0.1) and purified by preparative HPLC to afford the title compound as a white powder after lyophilization (55 mg, 47%). $^1$H NMR (600 MHz, Methanol-d4) δ 7.72 (d, J=7.9 Hz, 1H), 7.65 (d, J=7.5 Hz, 1H), 7.52 (t, J=7.7 Hz, 1H), 5.16 (dd, J=13.4, 5.2 Hz, 1H), 4.49 (d, J=4.2 Hz, 2H), 3.22 (t, J=7.0 Hz, 2H), 2.96-2.87 (m, 1H), 2.79 (ddd, J=17.7, 4.6, 2.4 Hz, 1H), 2.55-2.43 (m, 3H), 2.32 (t, J=7.4 Hz, 2H), 2.24 (t, J=7.5 Hz, 2H), 2.19 (ddd, J=10.6, 5.3, 2.7 Hz, 1H), 1.88 (p, J=7.4 Hz, 2H), 1.74 (p, J=7.5 Hz, 2H), 1.65-1.56 (m, 2H). HRMS (ESI) [M+H]$^+$ for $C_{23}H_{29}N_4O_7$ 473.2031, found 473.2038.

(1R)-3-(3,4-dimethoxyphenyl)-1-(3-(5-((5-((2-(2,6-dioxopiperidin-3-yl)-1-oxoisoindolin-4-yl)amino)-5-oxopentyl)amino)-5-oxopentanamido)phenyl)propyl (2S)-1-(3,3-dimethyl-2-oxopentanoyl)piperidine-2-carboxylate (Len-SLF)

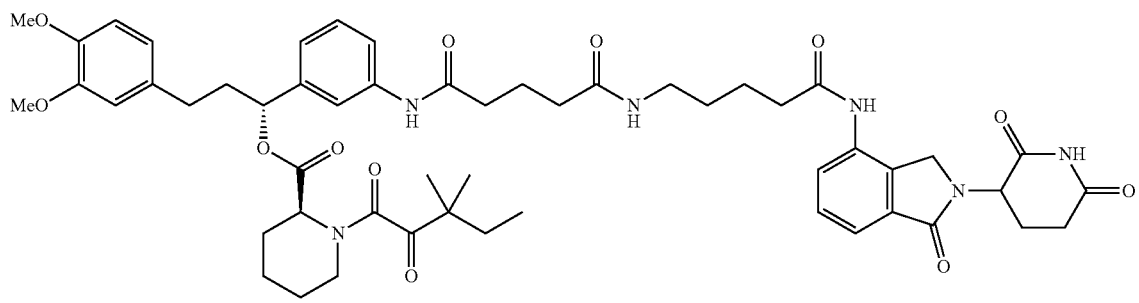 [SMILES: CCC(C)(C)C(=O)C(=O)N1CCCC[C@H]1C(=O)O[C@H](CCc1ccc(OC)c(OC)c1)c1cccc(NC(=O)CCCC(=O)NCCCCC(=O)Nc2cccc3c2CN(C2CCC(=O)NC2=O)C3=O)c1]

SI-3 (14 mg, 0.029 mmol, 1.5 eq.), COMU (12 mg, 0.028 mmol, 1.45 eq.), and N-methylmorpholine (6 µL, 0.057 mmol, 3 eq.) were dissolved in 150 µL of DMF and incubated for 1 min. SLF (10 mg, 0.019 mmol, 1 eq.) and catalytic 4-dimethylaminopyridine were added in 200 µL of DMF and the reaction was stirred at room temperature for 2 h. The reaction was diluted to 1 mL with water/acetonitrile/formic acid (50/50/0.1) and purified by preparative HPLC to afford the title compound as a white powder after lyophilization (10.6 mg, 57%). 1H NMR (600 MHz, DMSO-d6) δ 11.02 (s, 1H), 9.93 (s, 1H), 9.79 (s, 1H), 7.82 (d, J=1.4 Hz, 1H), 7.81 (d, J=1.4 Hz, 1H), 7.70 (t, J=1.9 Hz, 1H), 7.53-7.43 (m, 3H), 7.28 (t, J=7.9 Hz, 1H), 7.01 (dt, J=7.8, 1.3 Hz, 1H), 6.84 (d, J=8.2 Hz, 1H), 6.76 (d, J=2.0 Hz, 1H), 6.68 (dd, J=8.2, 2.0 Hz, 1H), 5.63 (dd, J=8.8, 4.8 Hz, 1H), 5.16-5.14 (m, 1H), 5.13 (d, J=5.3 Hz, 1H), 4.38 (d, J=17.4 Hz, 1H), 4.34 (d, J=17.4 Hz, 1H), 3.72 (s, 3H), 3.71 (s, 3H), 3.31-3.28 (m, 1H), 3.16 (td, J=13.3, 3.1 Hz, 1H), 3.07 (q, J=6.9 Hz, 2H), 2.91 (ddd, J=17.2, 13.6, 5.4 Hz, 1H), 2.60 (ddd, J=17.5, 4.5, 2.3 Hz, 1H), 2.57-2.51 (m, 2H), 2.37 (qd, J=8.0, 4.5 Hz, 3H), 2.29 (t, J=7.5 Hz, 2H), 2.24-2.19 (m, 1H), 2.15-2.08 (m, 3H), 2.01 (dtd, J=13.0, 5.3, 2.4 Hz, 2H), 1.79 (p, J=7.5 Hz, 2H), 1.72-1.67 (m, 2H), 1.66-1.56 (m, 5H), 1.49-1.41 (m, 2H), 1.39-1.28 (m, 1H), 1.26-1.18 (m, 1H), 1.16 (s, 3H), 1.14 (s, 3H), 1.03 (d, J=7.1 Hz, 1H), 0.80 (t, J=7.5 Hz, 3H). HRMS (ESI) [M+H]+ for $C_{53}H_{67}N_6O_{12}$ 979.4811, found 979.4808.

Synthesis of KB02-SLF
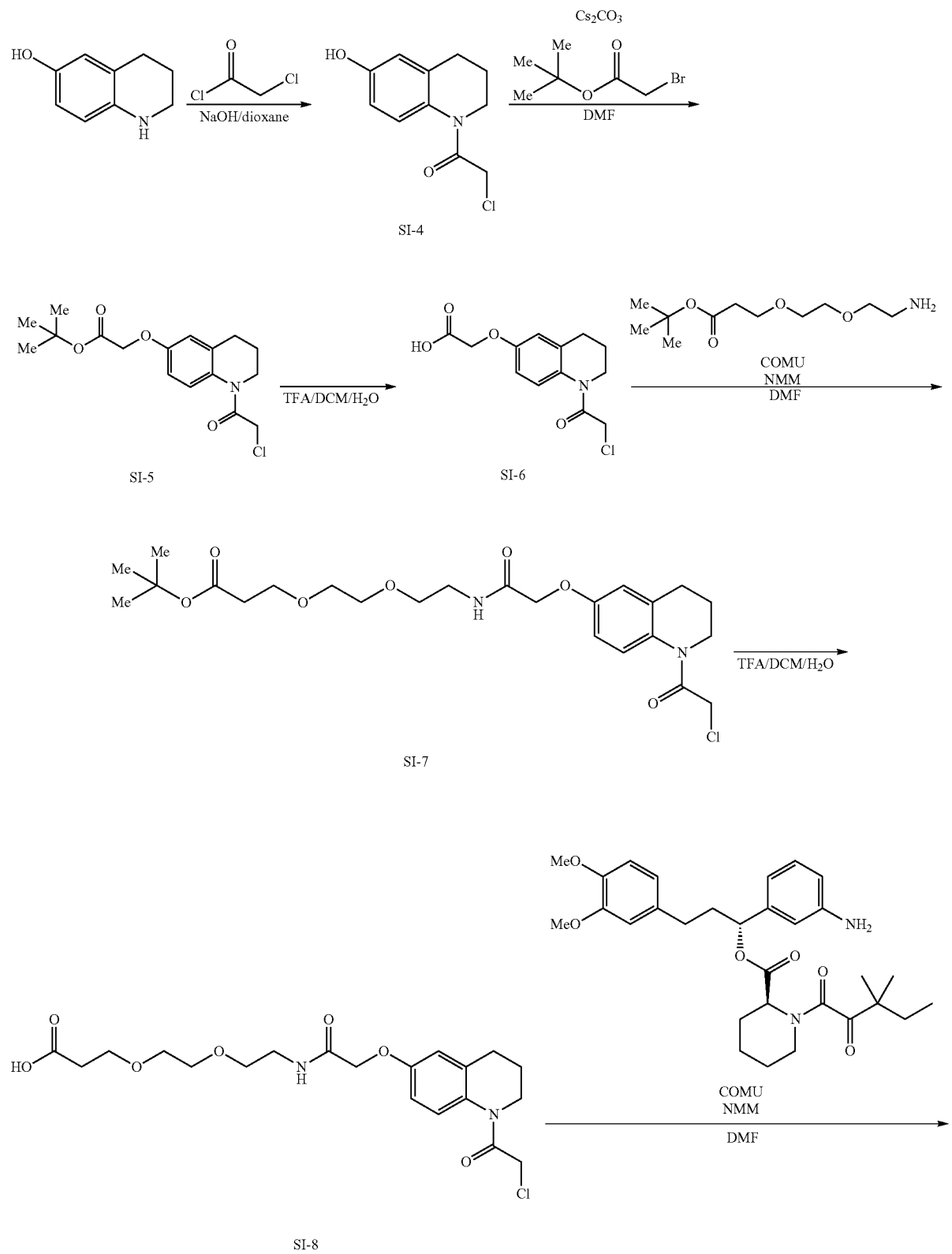
Scheme 2. Synthesis of KB02-SLF

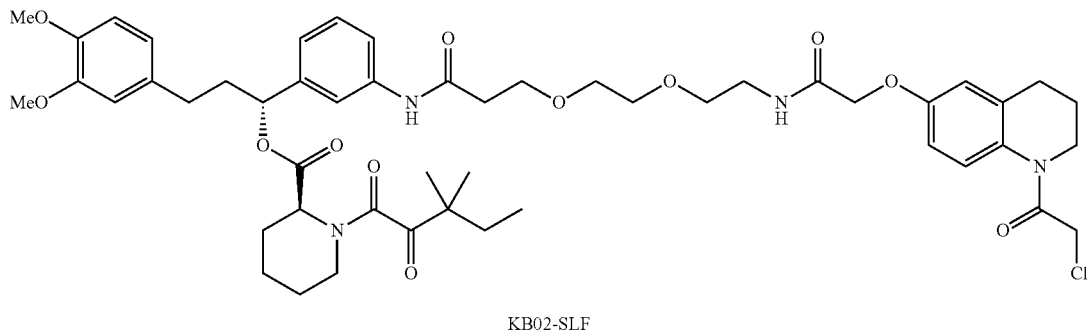

KB02-SLF

2-chloro-1-(6-hydroxy-3,4-dihydroquinolin-1(2H)-yl)ethan-1-one (SI-4)

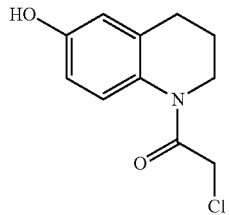 [SMILES: O=C(CCl)N1CCCc2cc(O)ccc21]

1,2,3,4-tetrahydroquinolin-6-ol (1 g, 6.7 mmol, 1 eq.) and NaOH (0.32 g, 8.0 mmol, 1.2 eq.) were dissolved in water/dioxane (1:1, 20 mL) at 0° C. 2-chloroacetyl chloride (0.586 mL, 7.4 mmol, 1.1 eq.) was added dropwise over five minutes and the reaction was stirred at room temperature for 4 h. The reaction was monitored by TLC (hexane:ethyl acetate=1:1). The desired product was confirmed by MS. The reaction solution was acidified with 1M HCl (pH<4), extracted with ethyl acetate twice, washed with brine, dried over anhydrous $Na_2SO_4$ and concentrated under reduced pressure. The resultant residue was used for the next step without purification.

tert-butyl 2-((1-(2-chloroacetyl)-1,2,3,4-tetrahydroquinolin-6-yl)oxy)acetate (SI-5)

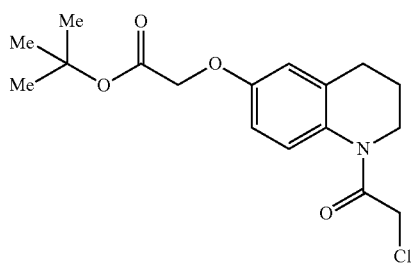 [SMILES: CC(C)(C)OC(=O)COc1ccc2c(c1)CCCN2C(=O)CCl]

The crude product from last step (1.5 g, 6.7 mmol, 1 eq.) was dissolved in 15 mL DMF with $Cs_2CO_3$ (3.2 g, 10.1 mmol, 1.5 eq.). Add tert-Butyl bromoacetate (1.3 mL, 8.4 mmol, 1.25 eq.) and stir the reaction at room temperature for 3 h. The reaction was monitored by TLC (hexane:ethyl acetate=1:1). The desired product was confirmed by MS. The reaction solution was diluted with ethyl acetate and acidified with 1M HCl, then extracted with ethyl acetate (2×30 mL), dried over anhydrous $Na_2SO_4$ and concentrated under reduced pressure. The resultant residue was purified by column chromatography (10-30% ethyl acetate/hexane) and dried under vacuum overnight. The product was yellow oil (774 mg, 34%). The residue was used in the next step without further purification.

2-((1-(2-chloroacetyl)-1,2,3,4-tetrahydroquinolin-6-yl)oxy)acetic Acid (SI-6)

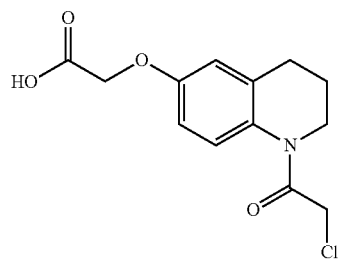 [SMILES: O=C(O)COc1ccc2c(c1)CCCN2C(=O)CCl]

SI-5 (981 mg, 2.9 mmol) was dissolved in 2 mL of dichloromethane, 2 mL of trifluoroacetic acid and 40 μL of $H_2O$. The reaction was stirred at room temperature for 2 h. The solvent was removed under reduced pressure and the residue dried under vacuum to provide the title compounds as tan amorphous solid (623 mg, 76%) $^1$H NMR (500 MHz, DMSO-d6) δ 7.33 (s, 1H), 6.82-6.65 (m, 2H), 4.65 (s, 2H), 4.55-4.35 (m, 2H), 3.68-3.64 (m, 2H), 2.67 (s, 2H), 1.88 (q, J=7.1, 6.6 Hz, 2H). HRMS (ESI) [M+H]$^+$ for $C_{13}H_{15}ClNO_4$ 284.0684, found 284.0684.

tert-butyl 3-(2-(2-(2-((1-(2-chloroacetyl)-1,2,3,4-tetrahydroquinolin-6-yl)oxy)acetamido)ethoxy)ethoxy)propanoate (SI-7)

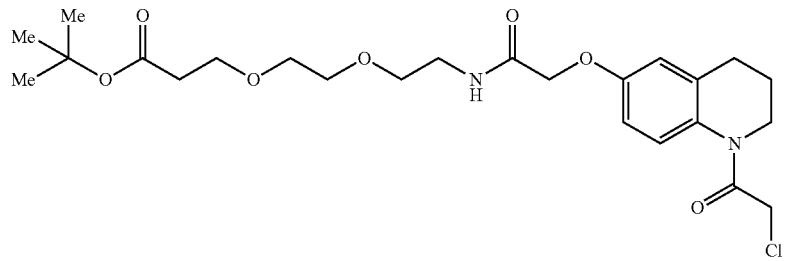 [SMILES: CC(C)(C)OC(=O)CCOCCOCCNC(=O)COc1ccc2c(c1)CCCN2C(=O)CCl]

SI-6 (100 mg, 0.35 mmol, 1.2 eq.), COMU (159 mg, 0.37 mmol, 1.2 eq.) and N-methylmorpholine (102 μL, 0.93 mmol, 3 eq.) were dissolved in 333 μL of DMF and incubated for 1 min. Amino-PEG2-t-butyl ester (90 mg, 0.39 mmol, 1.1 eq.) was added in 667 μL and the reaction was stirred for 1 h at room temperature. The reaction was diluted with ethyl acetate (10 mL) and water (10 mL). The organic layer was washed with water (3×10 mL) and 1N HCl (1×10 mL). The organic layer was collected, dried over anhydrous MgSO$_4$ and concentrated under reduced pressure. The residue was purified by flash chromatography (DCM:EtOAc; 1:1) to provide the title compound as a colorless oil (32 mg, 18%). $^1$H NMR (500 MHz, Chloroform-d) δ 7.04-6.99 (m, 1H), 6.78 (dd, J=8.8, 2.7 Hz, 1H), 6.76-6.71 (m, 1H), 4.48 (s, 2H), 4.19 (s, 1H), 4.05 (d, J=1.0 Hz, 1H), 3.80 (s, 2H), 3.71 (dtd, J=7.5, 6.4, 1.0 Hz, 2H), 3.63-3.57 (m, 6H), 3.56-3.53 (m, 1H), 3.50 (dd, J=5.8, 4.8 Hz, 1H), 2.71 (s, 2H), 2.50 (qd, J=6.3, 1.1 Hz, 2H), 2.01-1.95 (m, 2H), 1.44 (dd, J=5.4, 1.1 Hz, 9H). HRMS (ESI) [M+Na]$^+$ for C$_{24}$H$_{35}$ClN$_2$O$_7$Na 521.2025, found 521.2029.

3-(2-(2-(2-((1-(2-chloroacetyl)-1,2,3,4-tetrahydroquinolin-6-yl)oxy)acetamido)ethoxy)ethoxy)propanoic Acid (SI-8)

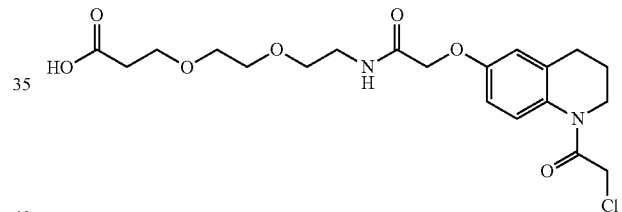

SI-7 (121 mg) was dissolved in 0.5 mL of dichloromethane, 0.5 mL of trifluoroacetic acid and 10 μL of H$_2$O and stirred room temperature for 2 h. The solvent was removed under reduced pressure and the residue was dried under vacuum. The residue was used without further purification.

(R)-1-(3-(3-(2-(2-(2-((1-(2-chloroacetyl)-1,2,3,4-tetrahydroquinolin-6-yl)oxy)acetamido)ethoxy)ethoxy)propanamido)phenyl)-3-(3,4-dimethoxyphenyl)propyl (S)-1-(3,3-dimethyl-2-oxopentanoyl)piperidine-2-carboxylate (KB02-SLF)

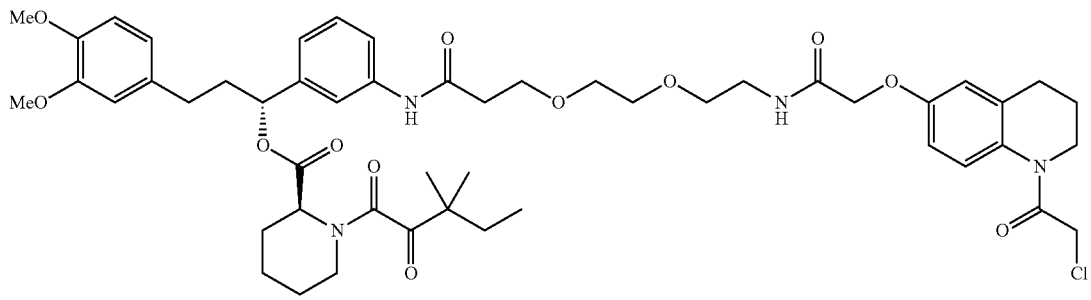 [SMILES: CCC(C)(C)C(=O)C(=O)N1CCCC[C@H]1C(=O)O[C@H](CCc1ccc(OC)c(OC)c1)c1cccc(NC(=O)CCOCCOCCNC(=O)COc2ccc3c(c2)CCCN3C(=O)CCl)c1]

SI-8 (13 mg, 0.029 mmol, 1.5 eq.), COMU (12 mg, 0.028 mmol, 1.45 eq.), and N-methylmorpholine (6 μL, 0.057 mmol, 3 eq.) were dissolved in 150 μL of DMF and incubated for 1 min. SLF (10 mg, 0.019 mmol, 1 eq.) and catalytic 4-dimethylaminopyridine were dissolved in 200 of DMF and added to the reaction. The reaction was stirred at room temperature for 2 h. The reaction was diluted to 1 mL with water/acetonitrile/formic acid (50/50/0.1) and purified via preparative HPLC and lyophilized to provide the title compound as a white powder (4.8 mg, 26%). $^1$H NMR (600 MHz, DMSO-d6) δ 9.98 (s, 1H), 8.04 (t, J=5.7 Hz, 1H), 7.70 (t, J=1.9 Hz, 1H), 7.46 (ddd, J=8.2, 2.1, 1.0 Hz, 1H), 7.29 (t, J=7.9 Hz, 1H), 7.02 (dt, J=7.8, 1.3 Hz, 1H), 6.84 (d, J=8.1 Hz, 1H), 6.80 (o, 1H), 6.76 (m, 3H), 6.68 (dd, J=8.2, 2.0 Hz, 1H), 5.63 (dd, J=8.7, 4.8 Hz, 1H), 5.14 (d, J=5.8 Hz, 1H), 4.44 (s, 2H), 3.72 (s, 3H), 3.71 (s, 3H), 3.68 (t, J=6.3 Hz, 2H), 3.65 (t, J=6.4 Hz, 2H), 3.49 (m, 4H), 3.43 (t, J=6.0 Hz, 2H), 3.27 (q, J=12.0 Hz, 2H), 3.15 (td, J=13.2, 3.0 Hz, 1H), 2.66 (s, 2H), 2.54 (m, 4H), 2.53 (o, 2H), 2.22 (d, J=13.5 Hz, 1H), 2.12 (br.s, 1H), 2.01 (m, 1H), 1.86 (br.s, 2H), 1.76-1.48 (m, 5H), 1.34 (m, 1H), 1.22 (m, 1H), 1.16 (s, 3H), 1.14 (s, 3H), 1.03 (d, J=6.0 Hz, 1H), 0.80 (t, J=7.5 Hz, 3H). HRMS (ESI) [M+H]$^+$ for $C_{50}H_{66}ClN_4O_{12}$ 949.4360, found 949.4352.

Synthesis of KB02-PEG4-SLF

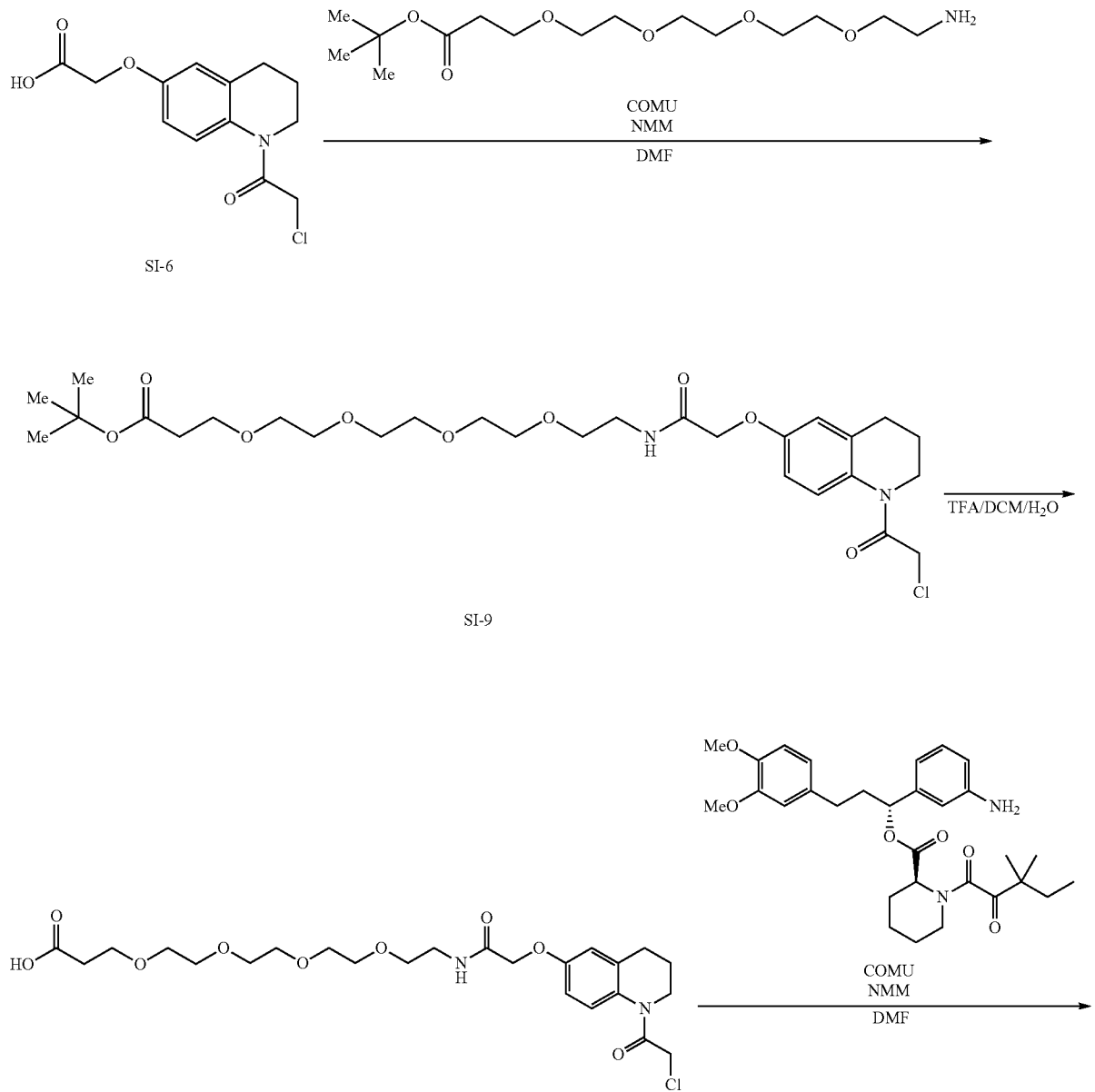

Scheme 3. Synthesis of KB02-PEG4-SLF

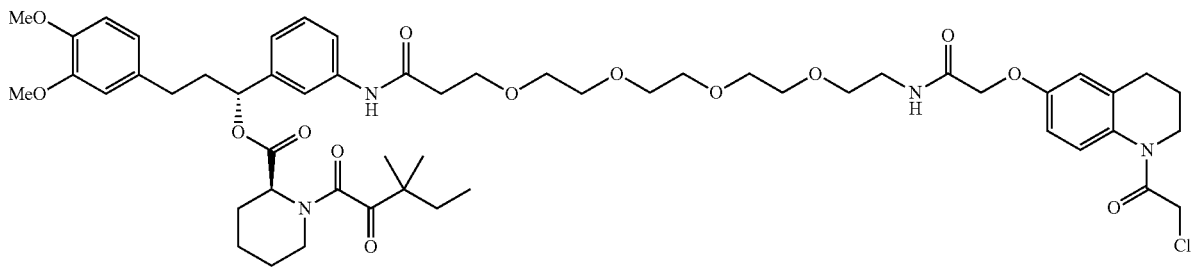

KB02-PEG4-SLF tert-butyl 1-((1-(2-chloroacetyl)-1,2,3,4-tetrahydro-quinolin-6-yl)oxy)-2-oxo-6,9,12,15-tetraoxa-3-azaoctadecan-18-oate (SI-9)

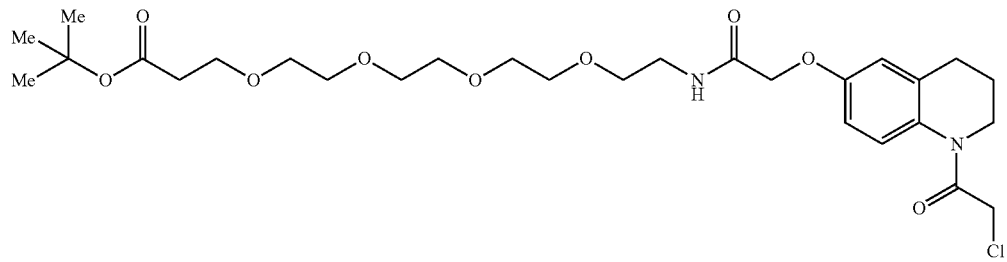 [SMILES: CC(C)(C)OC(=O)CCOCCOCCOCCOCCNC(=O)COc1ccc2c(c1)CCCN2C(=O)CCl]

SI-6 (76 mg, 0.27 mmol, 1.2 eq.), COMU (115 mg, 0.27 mmol, 1.2 eq.), and N-methylmorpholine (74 μL, 0.67 mmol, 3 eq.) were dissolved in 333 μL of DMF and incubated for 1 min. Amino-PEG4-t-butyl ester (72 mg, 0.22 mmol, 1 eq.) was added in 667 μL and the reaction was stirred for 1 h at room temperature. The reaction was then diluted with ethyl acetate (10 mL) and water (10 mL). The organic layer was washed with water (3×10 mL) and 1N HCl (1×10 mL). The organic layer was collected, dried over anhydrous MgSO$_4$ and removed under reduced pressure. The residue was purified by flash chromatography (DCM: EtOAc, 1:1) to provide the title compound as a colorless oil (44 mg, 22%). $^1$h NMR (500 MHz, Chloroform-d) δ 7.10 (s, 1H), 6.81-6.69 (m, 2H), 4.46 (d, J=11.3 Hz, 2H), 4.18 (s, 1H), 3.83-3.72 (m, 2H), 3.70-3.67 (m, 4H), 3.63 (s, 8H), 3.61-3.57 (m, 6H), 3.54 (dd, J=7.6, 3.2 Hz, 2H), 2.70 (s, 2H), 2.48 (td, J=6.5, 1.5 Hz, 2H), 1.98 (d, J=5.2 Hz, 2H), 1.43 (d, J=3.1 Hz, 9H). HRMS (ESI) [M+H]$^+$ for C$_{24}$H$_{44}$ClN$_2$O$_9$ 587.2730, found 587.2721.

1-((1-(2-chloroacetyl)-1,2,3,4-tetrahydroquinolin-6-yl)oxy)-2-oxo-6,9,12,15-tetraoxa-3-azaoctadecan-18-oic Acid (SI-10)

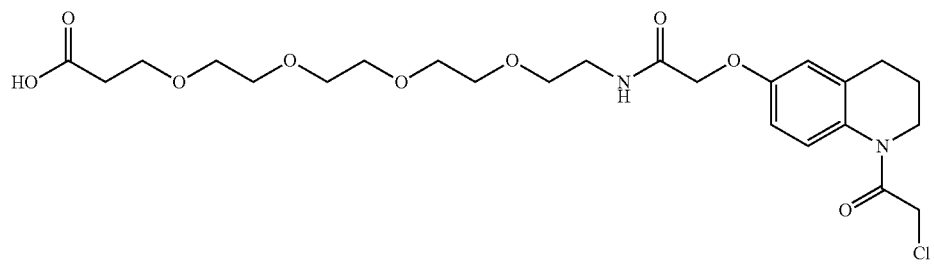 [SMILES: O=C(O)CCOCCOCCOCCOCCNC(=O)COc1ccc2c(c1)CCCN2C(=O)CCl]

SI-9 (119 mg) was dissolved in 0.5 mL of dichloromethane, 0.5 mL of trifluoroacetic acid and 10 µL of H$_2$O and stirred at room temperature for 2 h. Upon consumption of the starting material, the reaction was concentrated under reduced pressure and dried under vacuum. The resulting residue was used without further purification.

(R)-1-(3-(1-((1-(2-chloroacetyl)-1,2,3,4-tetrahydroquinolin-6-yl)oxy)-2-oxo-6,9,12,15-tetraoxa-3-azaoctadecan-18-amido)phenyl)-3-(3,4-dimethoxyphenyl)propyl (S)-1-(3,3-dimethyl-2-oxopentanoyl) piperidine-2-carboxylate (KB02-PEG4-SLF)

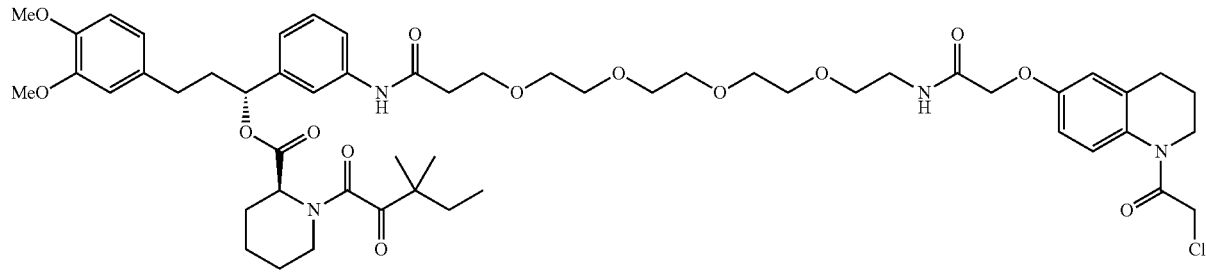 [SMILES: CCC(C)(C)C(=O)C(=O)N1CCCC[C@H]1C(=O)O[C@H](CCc1ccc(OC)c(OC)c1)c1cccc(NC(=O)CCOCCOCCOCCOCCNC(=O)COc2ccc3c(c2)CCCN3C(=O)CCl)c1]

SI-10 (13 mg, 0.025 mmol, 1.5 eq.), COMU (10 mg, 0.024 mmol, 1.45 eq.), and N-methylmorpholine (6 µL, 0.057 mmol, 3 eq.) were dissolved in 150 µL of DMF and incubated for 1 min. SLF (9 mg, 0.017 mmol, 1 eq.) was added in 200 µL of DMF. The reaction was stirred at room temperature for 2 h then the reaction was diluted to 1 mL with water/acetonitrile/formic acid (50/50/0.1). The mixture was purified by preparative HPLC and lyophilized to provide the title compound as a white powder (9.5 mg, 55%). $^1$H NMR (500 MHz, DMSO-d6) δ 9.98 (s, 1H), 8.04 (t, J=6.5 Hz, 1H), 7.71 (br.s, 1H), 7.46 (d, J=8.0 Hz, 1H), 7.29 (t, J=7.5 Hz, 1H), 7.02 (d, J=7.5 Hz, 1H), 6.84 (d, J=8.0 Hz, 1H), 6.81 (o, 1H), 6.76 (m, 3H), 6.68 (dd, J=8.5, 1.5 Hz, 1H), 5.63 (m, 1H), 5.14 (d, J=5.5 Hz, 1H), 4.45 (s, 2H), 3.72 (s, 3H), 3.71 (s, 3H), 3.71 (o, 2H), 3.67 (m, J=6.3 Hz, 4H), 3.49 (br.s, 4H), 3.47 (br.s, 8H), 3.43 (t, J=6.5 Hz, 2H), 3.29 (m, 2H), 3.16 (td, J=13.0, 2.0 Hz, 1H), 2.67 (s, 2H), 2.53 (m, 4H), 2.23 (d, J=12.0 Hz, 1H), 2.16-2.10 (m, 2H), 2.01 (m, 1H), 1.91-1.82 (m, 2H), 1.70-1.60 (m, 5H), 1.34 (m, 1H), 1.16 (s, 3H), 1.14 (s, 3H), 1.03 (d, J=5.0 Hz, 1H), 0.80 (t, J=7.5 Hz, 3H). FIRMS (ESI) [M+H]$^+$ for C$_{54}$H$_{74}$ClN$_4$O$_{14}$ 1037.4884, found 1037.4888.

Synthesis of KB02-PEG0-SLF

Scheme 4. Synthesis of KB02-PEG0-SLF

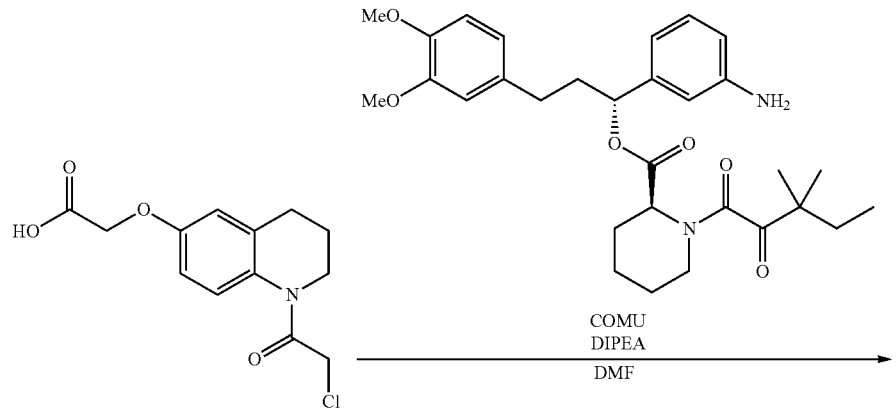

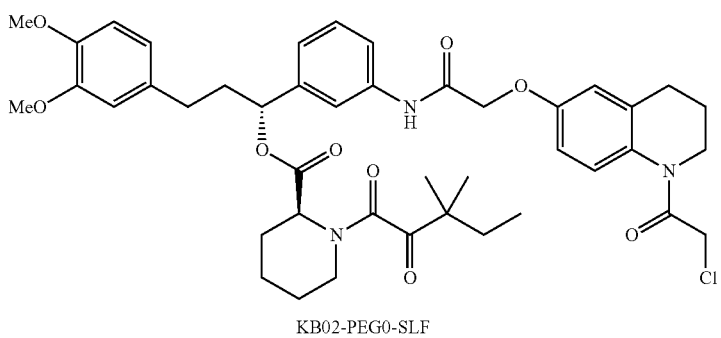

KB02-PEG0-SLF (R)-1-(3-(2-((1-(2-chloroacetyl)-1,2,3,4-tetrahydro-quinolin-6-yl)oxy)acetamido)phenyl)-3-(3,4-dimethoxyphenyl)propyl (S)-1-(3,3-dimethyl-2-oxopentanoyl)piperidine-2-carboxylate (KB02-PEG0-SLF)

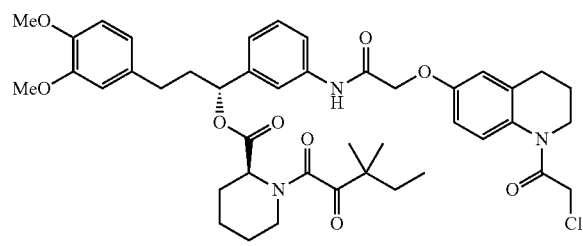 [SMILES: CCC(C)(C)C(=O)C(=O)N1CCCC[C@H]1C(=O)O[C@H](CCc1ccc(OC)c(OC)c1)c1cccc(NC(=O)COc2ccc3c(c2)CCCN3C(=O)CCl)c1]

SI-6 (8 mg, 0.029 mmol, 1.5 eq.), COMU (12 mg, 0.028 mmol, 1.45 eq.), and N-methylmorpholine (6 μL, 0.057 mmol, 3 eq.) were dissolved in 150 μL of DMF and incubated for 1 min. SLF (10 mg, 0.019 mmol, 1 eq.) and catalytic 4-dimethylaminopyridine were added to the reaction in 200 μL of DMF. The reaction was stirred at room temperature for 2 h and then diluted to 1 mL with water/acetonitrile/formic acid (50/50/0.1) and purified by preparative HPLC and lyophilized to provide the title compound as a white powder (9.1 mg, 60%). $^1$H NMR (500 MHz, Chloroform-d) δ 8.39 (s, 1H), 7.67 (d, J=8.5 Hz, 1H), 7.55 (s, 1H), 7.35 (t, J=7.9 Hz, 1H), 7.14-7.10 (m, 1H), 6.91-6.82 (m, 2H), 6.78 (d, J=8.7 Hz, 1H), 6.71-6.65 (m, 2H), 5.79 (dd, J=8.0, 5.5 Hz, 1H), 5.33 (d, J=5.7 Hz, 1H), 4.61-4.59 (m, 2H), 4.20 (s, 2H), 3.86 (s, 3H), 3.85 (s, 3H), 3.81 (s, 1H), 3.35 (d, J=13.3 Hz, 1H), 3.15 (td, J=13.1, 3.1 Hz, 1H), 2.74 (s, 2H), 2.66-2.52 (m, 2H), 2.36 (d, J=13.8 Hz, 1H), 2.26 (dtd, J=14.3, 8.9, 5.6 Hz, 1H), 2.12-2.04 (m, 1H), 1.78-1.72 (m, 1H), 1.72-1.67 (m, 1H), 1.67-1.60 (m, 1H), 1.56 (s, 5H), 1.41-1.33 (m, 1H), 1.21 (d, J=4.2 Hz, 6H), 1.12 (d, J=3.5 Hz, 1H), 0.87 (t, J=7.5 Hz, 3H), 0.80 (t, J=7.5 Hz, 1H). HRMS (ESI) [M+H]$^+$ for $C_{43}H_{53}ClN_3O_9$ 790.3465, found 790.3461.

Synthesis of KB03-SLF

Scheme 5. Synthesis of KB03-SLF

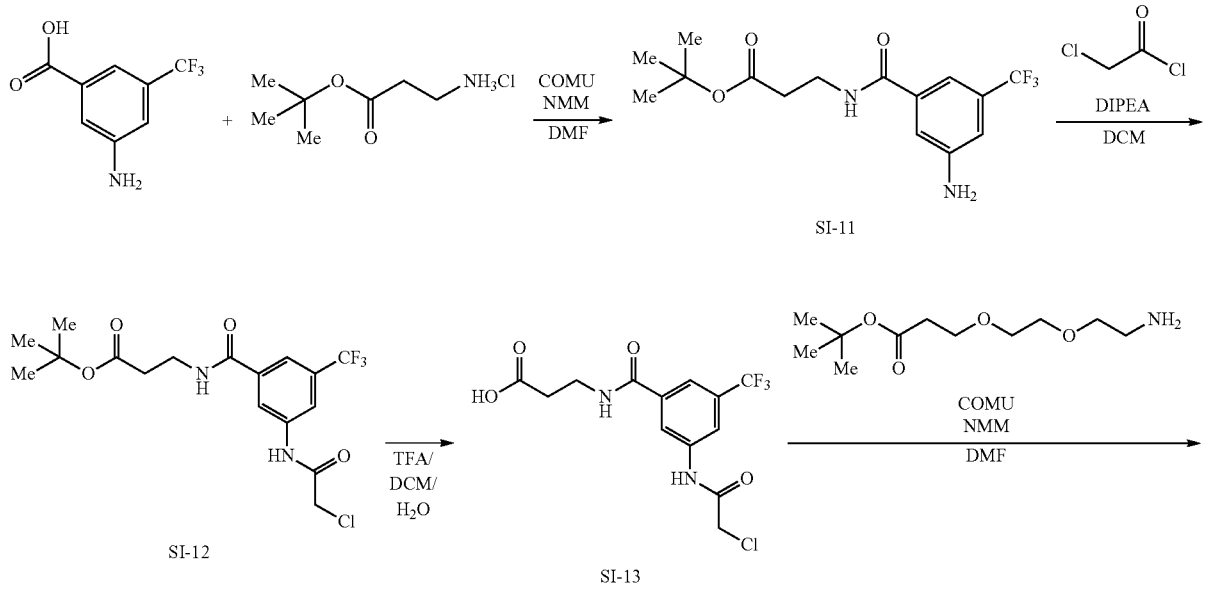

-continued
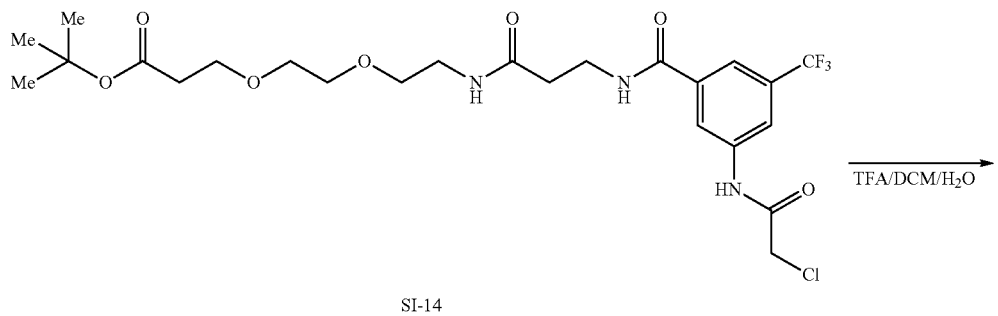
SI-14
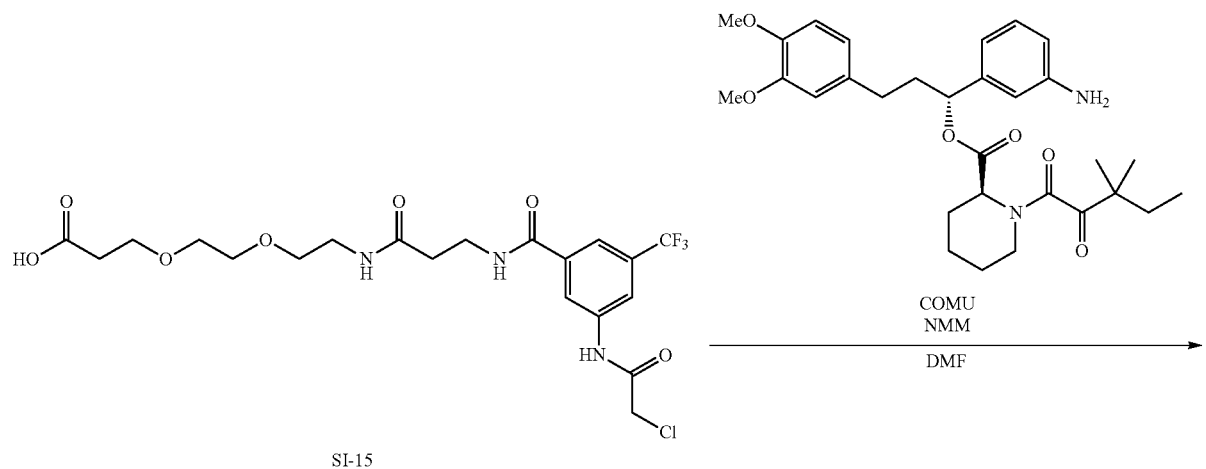
SI-15
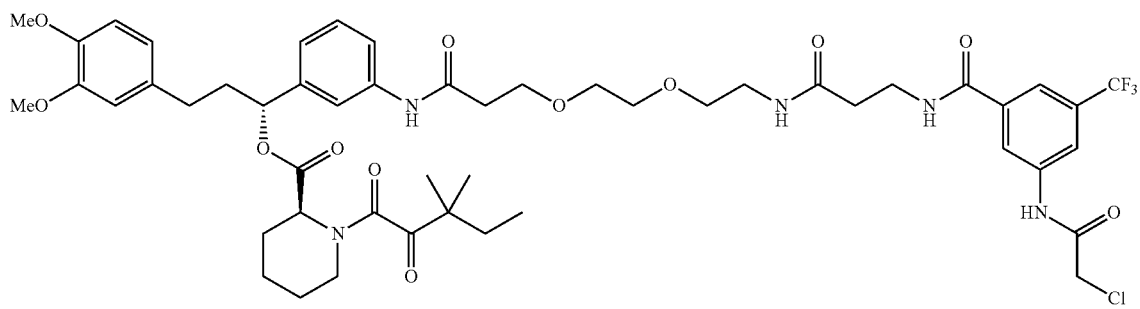
KB03-SLF tert-butyl 3-(3-amino-5-(trifluoromethyl)benzamido)propanoate (SI-11)

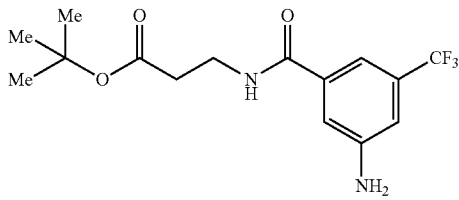 [SMILES: CC(C)(C)OC(=O)CCNC(=O)c1cc(N)cc(C(F)(F)F)c1]

3-amino-5-(trifluoromethyl)benzoic acid (205 mg, 1 mmol, 1 eq.), COMU (428 mg, 1 mmol, 1 eq.), and N-methylmorpholine (443 µL, 4 mmol, 4 eq.) were dissolved in 400 µL of DMF and incubated for 1 min. Beta-Alanine tert-butyl ester hydrochloride (218 mg, 1.2 mmol, 1.2 eq.) was added in 600 µL of DMF and the reaction was stirred for 2 h at room temperature. The reaction was diluted with ethyl acetate (10 mL), washed with water (3×10 mL), dried over anhydrous $Na_2SO_4$, and concentrated under reduced pressure. The residue was purified by prep TLC (dichloromethane/methanol=9/1) to afford the title compound as a yellow solid (239 mg, 72%). $^1$H NMR (600 MHz, Methanol-d4) δ 7.25 (d, J=2.1 Hz, 2H), 7.05 (t, J=2.0 Hz, 1H), 3.58 (t, J=6.9 Hz, 2H), 2.56 (t, J=6.9 Hz, 2H), 1.45 (s, 9H). MS (ESI) $[M+H]^+$ for $C_{15}H_{20}F_3N_2O_3$ 333.1, found 333.1.

tert-butyl 3-(3-(2-chloroacetamido)-5-(trifluoromethyl)benzamido)propanoate (SI-12)

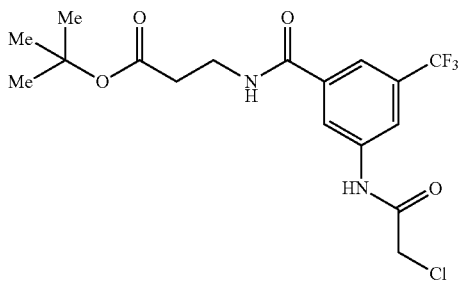 [SMILES: CC(C)(C)OC(=O)CCNC(=O)c1cc(NC(=O)CCl)cc(C(F)(F)F)c1]

SI-11 (239 mg, 0.72 mmol, 1 eq.) and N,N-diisopropylethylamine (250 µL, 1.44 mmol, 2 eq) were dissolved in 4 mL dichloromethane and cooled to 0° C. Chloroacetyl chloride (86 µL, 1.1 mmol, 1.5 eq.) was added dropwise. After complete addition, the reaction was warmed to room temperature and stirred for 2 h. The reaction was diluted with dichloromethane (10 mL), washed with saturated $NaHCO_3$ (15 mL), 1N HCl (15 mL), and brine (15 mL). The organic layer was dried over anhydrous $Na_2SO_4$ and concentrated under reduced pressure. The product was purified by prep TLC (ethyl acetate/hexane=9/1) to provide the title compound as a brown amorphous solid (230 mg, 78%). $^1$H NMR (600 MHz, Chloroform-d) δ 8.67 (s, 1H), 8.16 (s, 1H), 8.07 (t, J=1.8 Hz, 1H), 7.73 (s, 1H), 7.03 (t, J=6.1 Hz, 1H), 4.21 (s, 2H), 3.69 (q, J=6.0 Hz, 2H), 2.57 (t, J=6.0 Hz, 2H), 1.46 (s, 9H). HRMS (ESI) $[M+H]^+$ for $C_{17}H_{20}ClF_3N_2O_4Na$ 431.0956, found 431.0960.

3-(3-(2-chloroacetamido)-5-(trifluoromethyl)benzamido)propanoic Acid (SI-13)

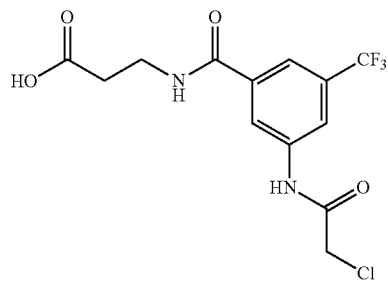 [SMILES: O=C(O)CCNC(=O)c1cc(NC(=O)CCl)cc(C(F)(F)F)c1]

SI-12 (113 mg) was dissolved in 1 mL of dichloromethane, 1 mL of trifluoroacetic acid and 20 µL of $H_2O$. The reaction was stirred at room temperature for 2 h then concentrated and dried under vacuum. The resulting residue was used without further purification.

tert-butyl 1-(3-(2-chloroacetamido)-5-(trifluoromethyl)phenyl)-1,5-dioxo-9,12-dioxa-2,6-diazapentadecan-15-oate (SI-14)

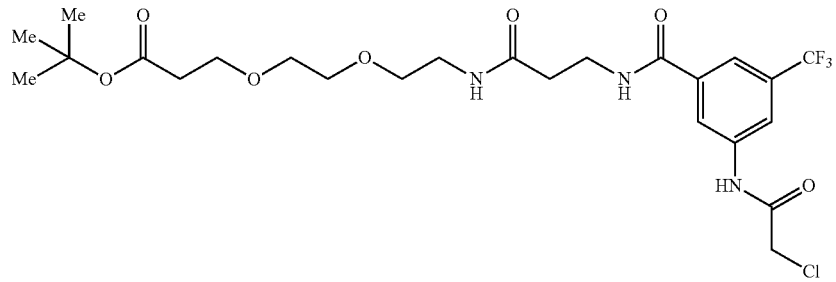 [SMILES: CC(C)(C)OC(=O)CCOCCOCCNC(=O)CCNC(=O)c1cc(NC(=O)CCl)cc(C(F)(F)F)c1]

SI-13 (65 mg, 0.18 mmol, 1.2 eq.), COMU (79 mg, 0.18 mmol, 1.2 eq.), and N-methylmorpholine (51 µL, 0.46 mmol, 3 eq.) were dissolved in 333 µL of DMF and incubated for 1 min. Amino-PEG2-t-butyl ester (36 mg, 0.35 mmol, 1 eq.) was added in 667 µL of DMF and the reaction was stirred at room temperature for 1 h. The reaction was diluted with ethyl acetate (10 mL) and washed with water (3×20 mL) and brine (20 mL). The organic layer was collected, dried over anhydrous MgSO₄, filtered and concentrated under reduced pressure. The residue was purified by flash chromatography to provide the title compound as a colorless oil (40 mg, 13%). ¹H NMR (500 MHz, Chloroform-d) δ 8.91-8.85 (m, 1H), 8.24 (d, J=2.1 Hz, 1H), 8.03 (t, J=1.9 Hz, 1H), 7.83-7.80 (m, 1H), 7.63 (t, J=5.7 Hz, 1H), 4.21 (s, 2H), 3.72 (t, J=6.3 Hz, 2H), 3.69 (t, J=6.2 Hz, 2H), 3.60 (q, J=0.8 Hz, 2H), 3.57 (d, J=1.8 Hz, 4H), 3.54 (ddd, J=5.3, 4.4, 2.6 Hz, 2H), 2.58-2.52 (m, 2H), 2.48 (dt, J=11.8, 6.3 Hz, 2H), 1.43 (d, J=7.1 Hz, 9H). FIRMS (ESI) [M+H]⁺ for $C_{24}H_{34}ClF_3N_3O_7$ 568.2032, found 568.2036.

1-(3-(2-chloroacetamido)-5-(trifluoromethyl)phenyl)-1,5-dioxo-9,12-dioxa-2,6-diazapentadecan-15-oic Acid (SI-15)

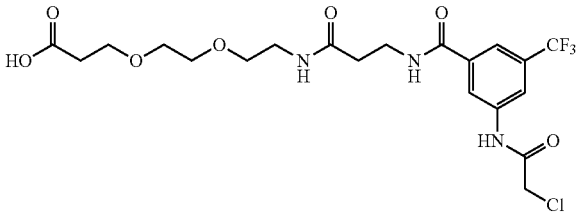 [SMILES: O=C(O)CCOCCOCCNC(=O)CCNC(=O)c1cc(NC(=O)CCl)cc(C(F)(F)F)c1]

SI-14 (135 mg) was dissolved in 0.5 mL of dichloromethane, 0.5 mL of trifluoroacetic acid and 10 µL of H₂O and stirred at room temperature for 2 h. The solvent was then removed under reduced pressure and dried under vacuum. The residue was used without further purification.

(R)-1-(3-(1-(3-(2-chloroacetamido)-5-(trifluoromethyl)phenyl)-1,5-dioxo-9,12-dioxa-2,6-diazapentadecan-15-amido)phenyl)-3-(3,4-dimethoxyphenyl) propyl (S)-1-(3,3-dimethyl-2-oxopentanoyl) piperidine-2-carboxylate (KB03-SLF)

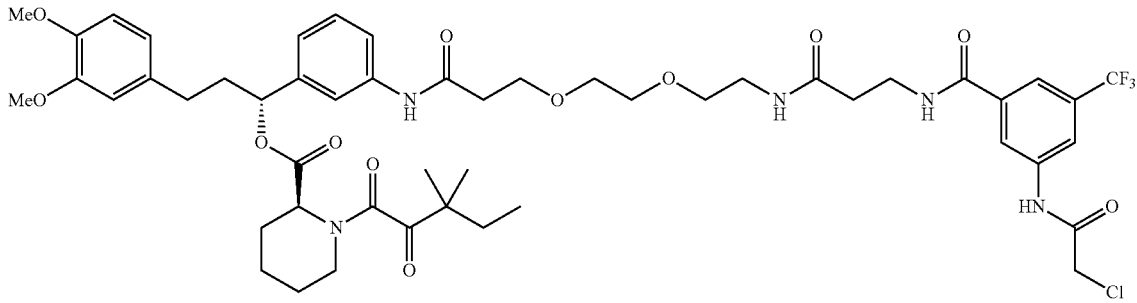 [SMILES: CCC(C)(C)C(=O)C(=O)N1CCCC[C@H]1C(=O)O[C@H](CCc1ccc(OC)c(OC)c1)c1cccc(NC(=O)CCOCCOCCNC(=O)CCNC(=O)c2cc(NC(=O)CCl)cc(C(F)(F)F)c2)c1]

SI-15 (13 mg, 0.025 mmol, 1.5 eq.), COMU (10 mg, 0.024 mmol, 1.45 eq.) and N-methylmorpholine (6 µL, 0.057 mmol, 3 eq.) were dissolved in 150 µL of DMF and incubated for 1 min. SLF (9 mg, 0.017 mmol, 1 eq.) and catalytic 4-dimethylaminopyridine was added in 200 µL of DMF and the reaction was stirred for 2 h at room temperature. The reaction was diluted up to 1 mL with water/acetonitrile/formic acid (50/50/0.1) and purified via preparative HPLC to provide the title compound as a white powder after lyophilization (9.4 mg, 55%). ¹H NMR (500 MHz, DMSO-d6) δ 10.80 (s, 1H), 9.98 (s, 1H), 8.80 (t, J=5.5 Hz, 1H), 8.24 (s, 1H), 8.21 (s, 1H), 7.96 (t, J=5.5 Hz, 1H), 7.91 (s, 1H), 7.70 (s, 1H), 7.46 (d, J=8.0 Hz, 1H), 7.29 (t, J=8.0 Hz, 1H), 7.02 (d, J=7.5 Hz, 1H), 6.84 (d, J=8.0 Hz, 1H), 6.76 (d, J=2.0 Hz, 1H), 6.68 (dd, J=8.0, 2.0 Hz, 1H), 5.63 (dd, J=9.0, 5.0 Hz, 1H), 5.13 (d, J=5.5 Hz, 1H), 4.30 (s, 2H), 3.72 (s, 3H), 3.71 (s, 3H), 3.66 (t, J=6.5 Hz, 2H), 3.47 (br.s, 6H), 3.38 (t, J=6.0 Hz, 2H), 3.18 (m, 2H), 2.54 (m, 4H), 2.38 (t, J=7.0 Hz, 2H), 2.22 (d, J=12.5 Hz, 1H), 2.17-2.11 (m, 2H), 2.01 (m, 1H), 1.69-1.56 (m, 5H), 1.33 (m, 1H), 1.23 (m, 1H), 1.16 (s, 3H), 1.14 (s, 3H), 1.03 (d, J=5.0 Hz, 1H), 0.80 (t, J=7.0 Hz, 3H). HRMS (ESI) [M+H]⁺ for $C_{50}H_{64}ClF_3N_5O_{12}$ 1018.4186, found 1018.4180.

Synthesis of KB05-SLF
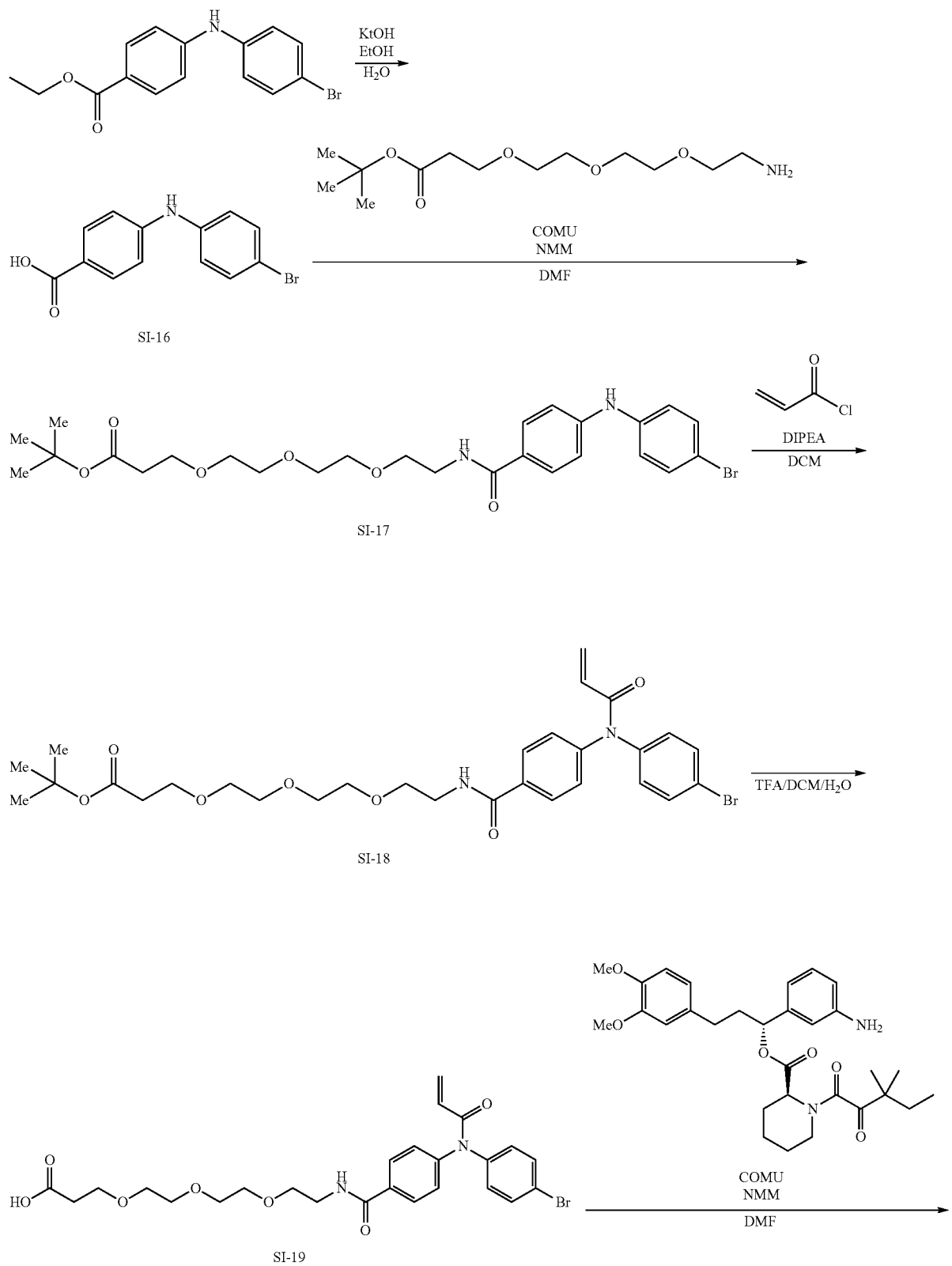
Scheme 6. Synthesis of KB05-SLF

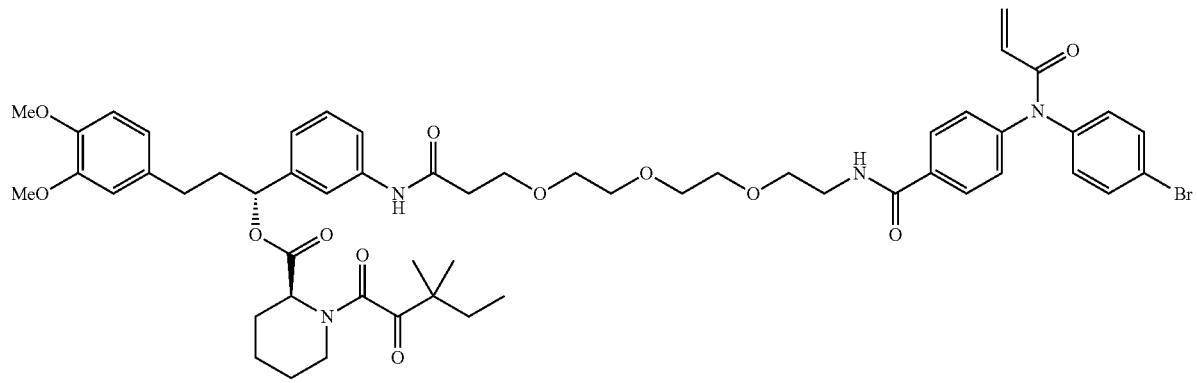

KB05-SLF

4-((4-bromophenyl)amino)benzoic Acid (SI-16)

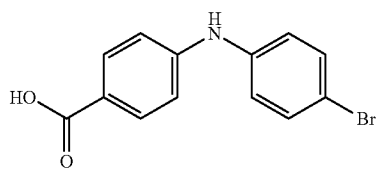 [SMILES: O=C(O)c1ccc(Nc2ccc(Br)cc2)cc1]

Ethyl 4-((4-bromophenyl)amino)benzoate (0.5 g, 1.5 mmol, 1 eq.) was dissolved in 7.8 mL ethanol (0.2 M). KOH (175 mg, 3 mmol, 2 eq.; in 15.6 mL water) was added and the reaction was stirred at 100° C. for 4 h. The ethanol was removed and the resulting aqueous solution was cooled to 0° C. and acidified with 2N HCl to pH 2. The precipitate was collected by vacuum filtration and washed with water. The precipitate was then dissolved in ethanol and evaporated under reduced pressure to remove the remaining water. The resulting powder was used in the next step without further purification.

tert-butyl 1-(4-((4-bromophenyl)amino)phenyl)-1-oxo-5,8,11-trioxa-2-azatetradecan-14-oate (SI-17)

SI-16 (202 mg, 0.69 mmol, 1.2 eq.), COMU (296 mg, 0.69 mmol, 1.2 eq.), and N-methylmorpholine (190 μL, 1.7 mmol, 3 eq.) were dissolved in 1.5 mL DMF and incubated for 1 min. Amino-PEG3-t-butyl ester (160 mg, 0.58 mmol, 1 eq.) was added in 2.5 mL DMF and the reaction was stirred for 2 h. The reaction was diluted with ethyl acetate (15 mL) and acidified with 1N HCl to pH 3. The organic layer was washed with water (3×25 mL) and brine (25 mL), dried over anhydrous MgSO$_4$, and concentrated under reduced pressure. The resulting residue was purified by flash chromatography to provide the title compound as a colorless oil (215 mg, 57%). $^1$H NMR (500 MHz, Chloroform-d) δ 7.66 (d, J=8.7 Hz, 2H), 7.33 (d, J=8.7 Hz, 2H), 6.97 (dd, J=8.8, 7.2 Hz, 4H), 6.82 (d, J=5.4 Hz, 1H), 3.63 (t, J=6.5 Hz, 2H), 3.62-3.57 (m, 10H), 3.54 (td, J=4.8, 4.4, 1.1 Hz, 2H), 2.43 (t, J=6.5 Hz, 2H), 1.39 (s, 9H). HRMS (ESI) [M+H]$^+$ for C$_{26}$H$_{36}$BrN$_2$O$_6$ 551.1751, found 551.1751.

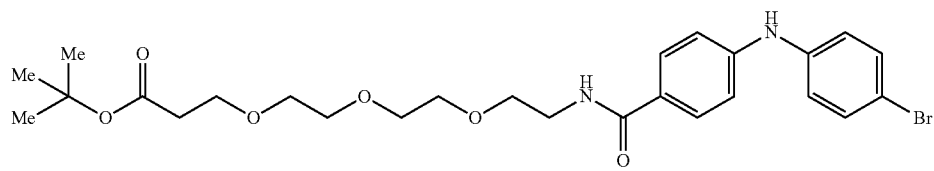 [SMILES: CC(C)(C)OC(=O)CCOCCOCCOCCNC(=O)c1ccc(Nc2ccc(Br)cc2)cc1]

tert-butyl 1-(4-(N-(4-bromophenyl)acrylamido)phenyl)-1-oxo-5,8,11-trioxa-2-azatetradecan-14-oate (SI-18)

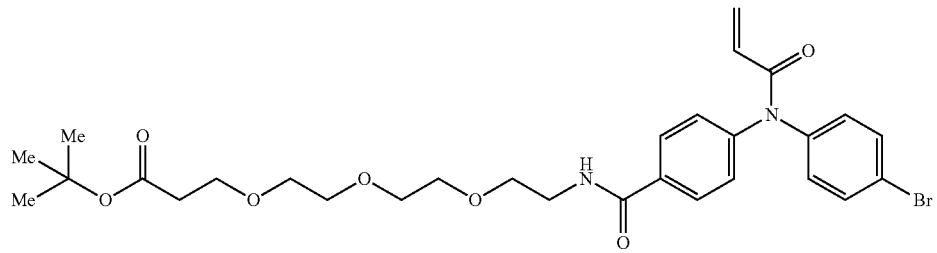 [SMILES: C=CC(=O)N(c1ccc(Br)cc1)c1ccc(C(=O)NCCOCCOCCOCCC(=O)OC(C)(C)C)cc1]

SI-17 (200 mg, 0.36 mmol, 1 eq.) and N,N-diisopropylethylamine (127 μL, 0.73 mmol, 2 eq.) were dissolved in 4 mL DCM. Acryloyl chloride (88 μL, 1.1 mmol, 3 eq.) was added dropwise at 0° C. followed by the addition of 4-dimethylaminopyridine (13 mg, 0.11 mmol, 0.1 eq.). The reaction was warmed to room temperature and stirred for 6 h. The reaction was diluted with DCM (20 mL), washed with saturated NaHCO₃ (25 mL), 1M HCl (25 mL), water (25 mL), dried over anhydrous MgSO₄, and concentrated under reduced pressure. The residue was used without further purification.

1-(4-(N-(4-bromophenyl)acrylamido)phenyl)-1-oxo-5,8,11-trioxa-2-azatetradecan-14-oic Acid (SI-19)

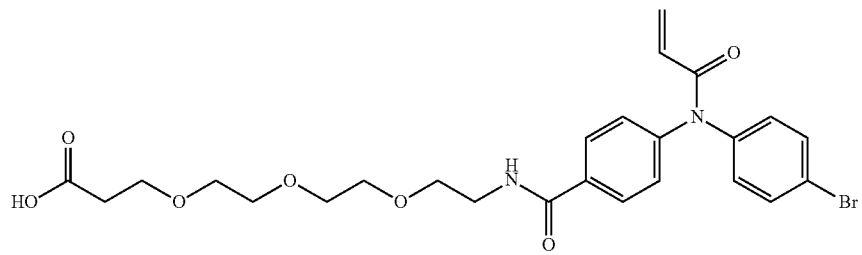 [SMILES: C=CC(=O)N(c1ccc(Br)cc1)c1ccc(C(=O)NCCOCCOCCOCCC(=O)O)cc1]

SI-18 (221 mg) was dissolved in 1 mL of dichloromethane, 1 mL of trifluoroacetic acid, and 20 μL of H₂O and stirred at room temperature for 2 h. The solvent was removed under reduced pressure and dried under vacuum. The residue was used without further purification.

(R)-1-(3-(1-(4-(N-(4-bromophenyl)acrylamido)phenyl)-1-oxo-5,8,11-trioxa-2-azatetradecan-14-amido)phenyl)-3-(3,4-dimethoxyphenyl)propyl (S)-1-(3,3-dimethyl-2-oxopentanoyl)piperidine-2-carboxylate (KB05-SLF)

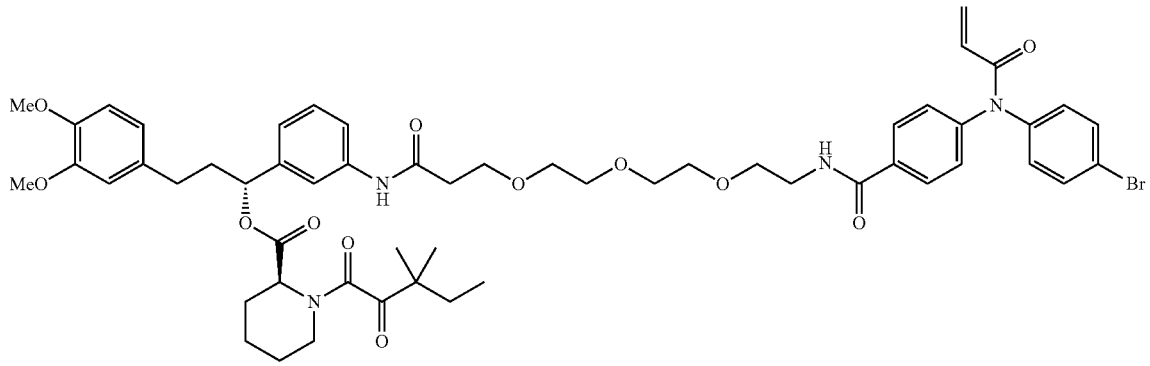 [SMILES: C=CC(=O)N(c1ccc(Br)cc1)c1ccc(C(=O)NCCOCCOCCOCCC(=O)Nc2cccc([C@@H](CCc3ccc(OC)c(OC)c3)OC(=O)[C@@H]3CCCCN3C(=O)C(=O)C(C)(C)CC)c2)cc1]

SI-19 (10 mg, 0.019 mmol, 1.5 eq.), COMU (8 mg, 0.018 mmol, 1.45 eq.), and N-methylmorpholine (4 µL, 0.037 mmol, 3 eq.) were dissolved in 150 µL of DMF in stirred for 1 min. SLF (7 mg, 0.012 mmol, 1 eq.) and catalytic 4-dimethylaminopyridine were added in 200 µL of DMF and the reaction was stirred at room temperature for 4 h. The reaction solution was diluted to 1 mL with water/acetonitrile/formic acid (50/50/0.1) and purified by preparative HPLC to provide the title compound as a white powder after lyphilization (3.7 mg, 28%). $^1$H NMR (500 MHz, DMSO-d6) δ 9.99 (s, 1H), 8.55 (t, J=5.0 Hz, 1H), 7.87 (d, J=8.0 Hz, 2H), 7.70 (s, 1H), 7.61 (d, J=8.0 Hz, 2H), 7.45 (d, J=8.0 Hz, 1H), 7.35 (d, J=8.0 Hz, 2H), 7.30-7.20 (m, 3H), 7.01 (d, J=7.5 Hz, 1H), 6.84 (d, J=8.0 Hz, 1H), 6.75 (s, 1H), 6.67 (d, J=8.0 Hz, 1H), 6.25 (d, J=17.0, 1H), 6.12 (dd, J=17.0, 10.0 Hz, 1H), 5.71 (d, J=10.0, 1H), 5.63 (m, 1H), 5.12 (d, J=4.5, 1H), 3.71 (s, 3H), 3.70 (s, 3H), 3.66 (t, J=6.0 Hz, 2H), 3.48 (m, 12H), 3.15 (m, 2H), 2.53 (m, 3H), 2.21 (d, J=13.5 Hz, 1H), 2.12 (m, 1H), 2.00 (m, 1H), 1.69-1.55 (m, 5H), 1.34 (m, 1H), 1.21 (m, 1H), 1.16 (s, 3H), 1.13 (s, 3H), 1.03 (d, J=5.0 Hz, 1H), 0.79 (t, J=7.5 Hz, 3H). HRMS (ESI) [M+H]$^+$ for $C_{55}H_{68}BrN_4O_{12}$ 1055.4011, found 1055.4009.

Synthesis of Inactive Control C-KB02-SLF

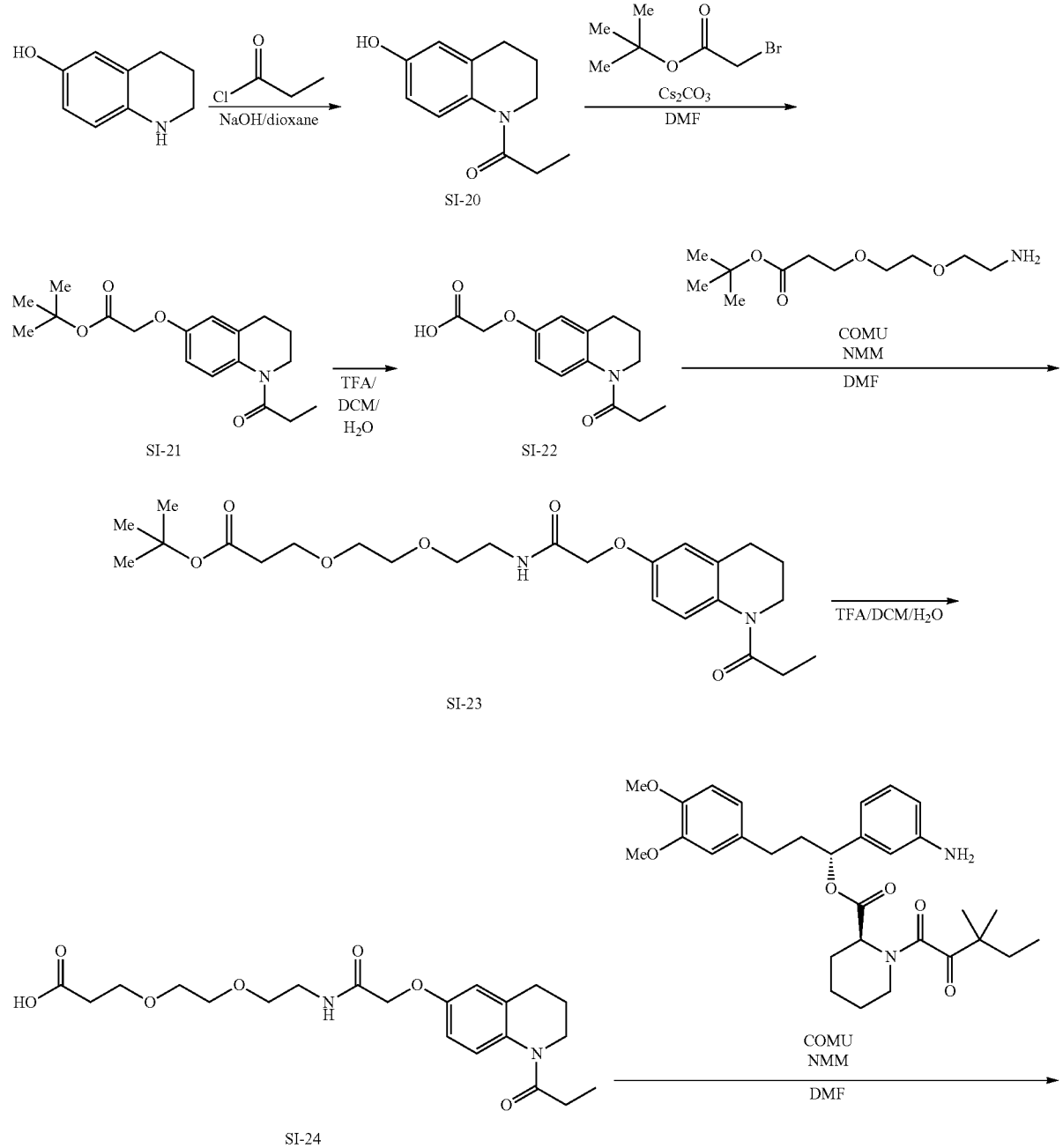

Scheme 7. Synthesis of C-KB02-SLF

-continued

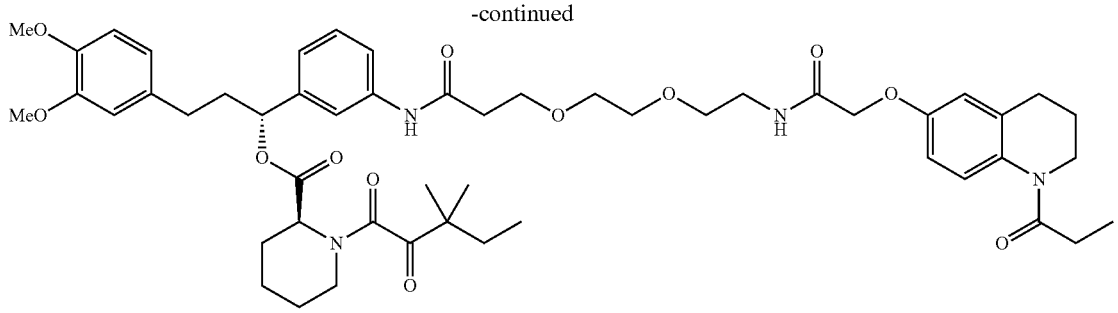

C-KB02-SLF 1-(6-hydroxy-3,4-dihydroquinolin-1(2H)-yl)propan-1-one (SI-20)

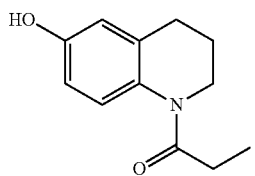

1,2,3,4-tetrahydroquinolin-6-ol (1 g, 6.7 mmol, 1 eq.) and NaOH (0.32 g, 8.0 mmol, 1.2 eq.) were dissolved in water/dioxane (1:1, 20 mL) at 0° C. Propanoyl chloride (0.64 mL, 7.4 mmol, 1.1 eq.) was added dropwise and the reaction was warmed to room temperature and stirred for 4 h. The reaction was acidified with 1N HCl (pH<4) then extracted with ethyl acetate (2×20 mL). The combined organic layers were washed with brine (100 mL), dried over anhydrous Na$_2$SO$_4$, and concentrated under reduced pressure. The resulting residue was used for the next step without purification.

tert-butyl 2-((1-propionyl-1,2,3,4-tetrahydroquinolin-6-yl)oxy)acetate (SI-21)

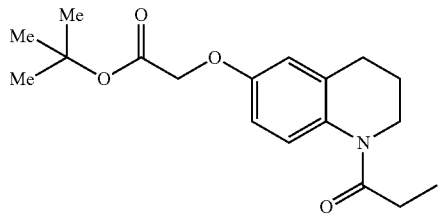 [SMILES: CCC(=O)N1CCCc2cc(OCC(=O)OC(C)(C)C)ccc21]

SI-20 (0.95 g, 4.6 mmol, 1 eq.) and Cs$_2$CO$_3$ (2.3 g, 6.9 mmol, 1.5 eq.) were dissolved in 15 mL DMF. Tert-Butyl bromoacetate (0.78 mL, 5.8 mmol, 1.25 eq.) was added dropwise and the reaction was stirred at room temperature for 3 h. The reaction was diluted with ethyl acetate (30 mL) and acidified with 1N HCl to pH<4. The organic layer was washed with water (3×40 mL), dried over anhydrous Na$_2$SO$_4$, and concentrated under reduced pressure. The residue was purified by flash chromatography (10-30% ethyl acetate/hexane) to provide the title compound as a yellow amorphous solid (815 mg, 55%). $^1$H NMR (500 MHz, Chloroform-d) δ 7.16-6.86 (m, 1H), 6.70-6.64 (m, 2H), 4.47 (s, 2H), 3.77-3.69 (m, 2H), 2.64 (t, J=6.6 Hz, 2H), 2.44 (q, J=7.4 Hz, 2H), 1.90 (p, J=6.8 Hz, 2H), 1.47 (s, 9H), 1.11 (t, J=7.4 Hz, 3H). HRMS (ESI) [M+H]$^+$ for $C_{18}H_{26}NO_4$ 320.1856, found 320.1859.

2-((1-propionyl-1,2,3,4-tetrahydroquinolin-6-yl)oxy)acetic Acid (SI-22)

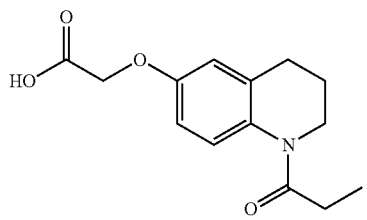 [SMILES: CCC(=O)N1CCCc2cc(OCC(=O)O)ccc21]

SI-21 (442 mg) was dissolved in 2 mL of dichloromethane, 2 mL of trifluoroacetic acid and, 40 μL of H$_2$O and stirred at room temperature for 2 h. The solvent was then removed and dried under vacuum. The resulting residue was used without further purification.

tert-butyl 3-(2-(2-(2-((1-propionyl-1,2,3,4-tetrahydroquinolin-6-yl)oxy)acetamido)ethoxy)ethoxy)propanoate (SI-23)

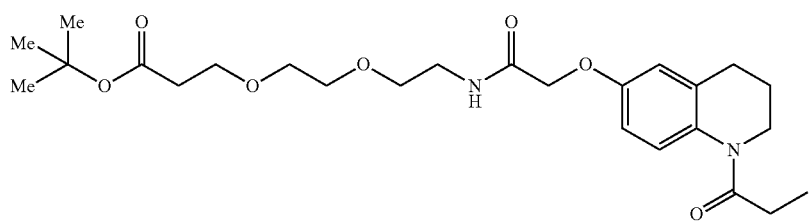 [SMILES: CCC(=O)N1CCCc2cc(OCC(=O)NCCOCCOCCC(=O)OC(C)(C)C)ccc21]

SI-22 (270 mg, 1.03 mmol, 1.2 eq.), COMU (440 mg, 1.03 mmol, 1.2 eq.), and N-methylmorpholine (283 μL, 2.57 mmol, 3 eq.) were dissolved in 1.5 mL of DMF and stirred for 1 min. Amino-PEG2-t-butyl ester (200 mg, 0.86 mmol, 1 eq.) was added in 2.5 mL of DMF and the reaction was stirred at room temperature for 1 h. The reaction was diluted with ethyl acetate (10 mL) and the organic phase washed with water (3×15 mL) and brine (1×15 mL). The organic layer was separated, dried over anhydrous MgSO$_4$, and concentrated. The residue was purified by flash chromatography (DCM/EtOAc; 1:1) to provide the title compound as a colorless oil (212 mg, 43%). $^1$H NMR (500 MHz, Chloroform-d) δ 7.01 (t, J=5.7 Hz, 1H), 6.71 (dt, J=8.7, 2.4 Hz, 1H), 6.68 (s, 1H), 4.43 (s, 2H), 3.74-3.69 (m, 2H), 3.67 (td, J=6.4, 2.0 Hz, 2H), 3.55 (d, J=2.3 Hz, 4H), 3.51 (ddd, J=6.5, 3.4, 1.5 Hz, 2H), 2.65 (s, 2H), 2.48-2.40 (m, 4H), 2.18 (qd, J=7.6, 2.1 Hz, 1H), 1.90 (td, J=6.6, 1.8 Hz, 2H), 1.41 (d, J=1.5 Hz, 2H), 1.40 (d, J=2.3 Hz, 9H), 1.11 (td, J=7.8, 2.6 Hz, 3H). HRMS (ESI) [M+Na]$^+$ for C$_{25}$H$_{38}$N$_2$O$_7$Na 501.2571, found 501.2580.

3-(2-(2-(2-((1-propionyl-1,2,3,4-tetrahydroquinolin-6-yl)oxy)acetamido)ethoxy)ethoxy)propanoic Acid (SI-24)

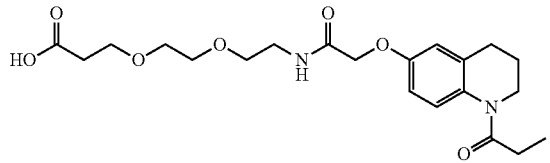 [SMILES: CCC(=O)N1CCCc2cc(OCC(=O)NCCOCCOCCC(=O)O)ccc21]

SI-23 (AMT) was dissolved in 0.5 mL of dichloromethane, 0.5 mL of trifluoroacetic acid, and 10 μL of H$_2$O and stirred at room temperature for 2 h. The reaction was then concentrated under reduced pressure and dried under vacuum. The resulting residue was used without further purification.

(R)-3-(3,4-dimethoxyphenyl)-1-(3-(3-(2-(2-(2-((1-propionyl-1,2,3,4-tetrahydroquinolin-6-yl)oxy)acetamido)ethoxy)ethoxy)propanamido)phenyl)propyl (S)-1-(3,3-dimethyl-2-oxopentanoyl)piperidine-2-carboxylate (C-KB02-SLF)

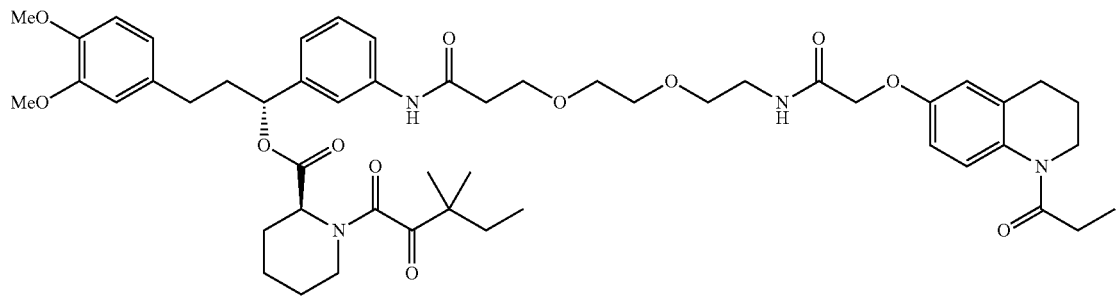 [SMILES: CCC(=O)N1CCCc2cc(OCC(=O)NCCOCCOCCC(=O)Nc3cccc([C@@H](CCc4ccc(OC)c(OC)c4)OC(=O)[C@@H]4CCCCN4C(=O)C(=O)C(C)(C)CC)c3)ccc21]

SI-24 (12 mg, 0.029 mmol, 1.5 eq.), COMU (12 mg, 0.028 mmol, 1.45 eq.), and N-methylmorpholine (6 μL, 0.057 mmol, 3 eq.) were dissolved in 150 μL of DMF and stirred for 1 min. SLF (10 mg, 0.019 mmol, 1 eq.) was added in 200 μL of DMF and the reaction was stirred for 4 h at room temperature. The reaction was diluted to 1 mL with water/acetonitrile/formic acid (50/50/0.1) and purified via preparative HPLC then lyophilized to provide the title compound as a white powder (8.4 mg, 47%). $^1$H NMR (500 MHz, Chloroform-d) δ 8.53 (s, 1H), 7.54 (d, J=13.2 Hz, 2H), 7.28 (d, J=7.9 Hz, 1H), 7.04 (t, J=6.5 Hz, 1H), 6.95 (d, J=6.2 Hz, 1H), 6.77 (dd, J=8.4, 4.4 Hz, 1H), 6.72 (dd, J=8.7, 3.0 Hz, 1H), 6.67 (dq, J=4.5, 2.1 Hz, 3H), 5.77 (dd, J=8.0, 5.4 Hz, 1H), 5.31 (d, J=5.7 Hz, 1H), 4.43 (s, 2H), 3.86 (s, 3H), 3.84 (s, 3H), 3.82 (t, J=5.9 Hz, 2H), 3.73 (s, 2H), 3.66 (d, J=4.6 Hz, 3H), 3.60 (t, J=5.3 Hz, 2H), 3.51 (q, J=5.5 Hz, 2H), 3.34 (d, J=13.5 Hz, 1H), 3.14 (td, J=13.1, 3.1 Hz, 1H), 2.67 (s, 2H), 2.63 (t, J=5.7 Hz, 1H), 2.56 (ddd, J=18.6, 9.9, 6.0 Hz, 1H), 2.47 (q, J=7.4 Hz, 2H), 2.35 (d, J=13.7 Hz, 1H), 2.22 (ddd, J=13.8, 11.5, 7.1 Hz, 1H), 2.10-2.01 (m, 1H), 1.93 (p, J=6.5 Hz, 2H), 1.73-1.69 (m, 1H), 1.69-1.65 (m, 1H), 1.65-1.62 (m, 1H), 1.58 (s, 6H), 1.45 (ddt, J=12.6, 8.6, 3.8 Hz, 1H), 1.36 (d, J=13.0 Hz, 1H), 1.22 (d, J=5.8 Hz, 5H), 1.15 (t, J=7.4 Hz, 3H), 1.11 (d, J=2.3 Hz, 1H), 0.89 (t, J=7.5 Hz, 2H), 0.80 (t, J=7.5 Hz, 1H). HRMS (ESI) [M+H]$^+$ for C$_{58}$H$_{69}$N$_4$O$_{12}$ 929.4906, found 929.4902.

Synthesis of KB02-JQ1
Scheme 8. Synthesis of KB02-JQ1
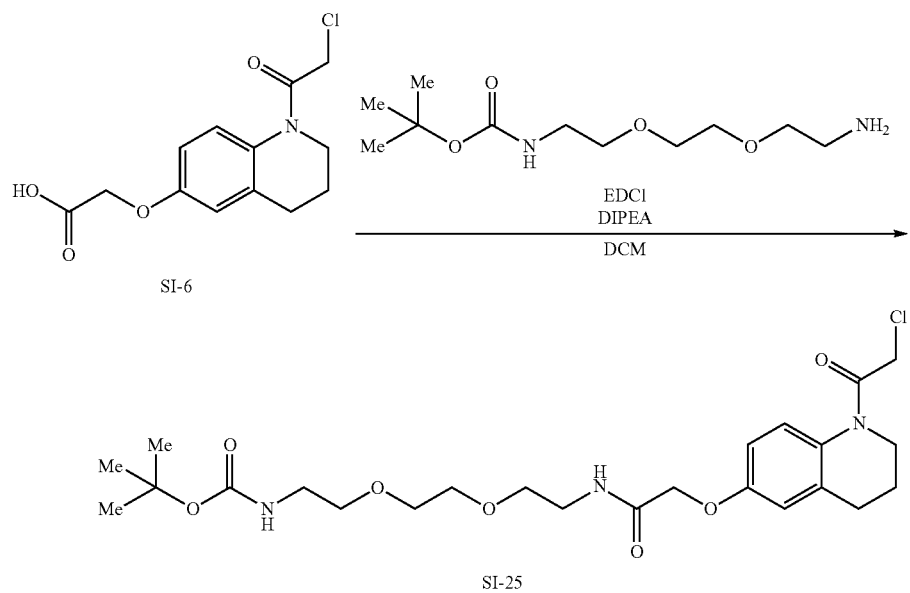
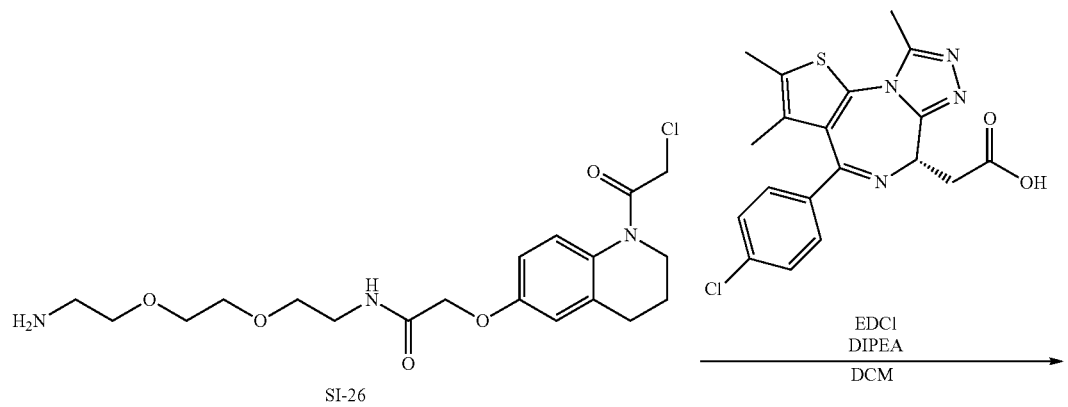
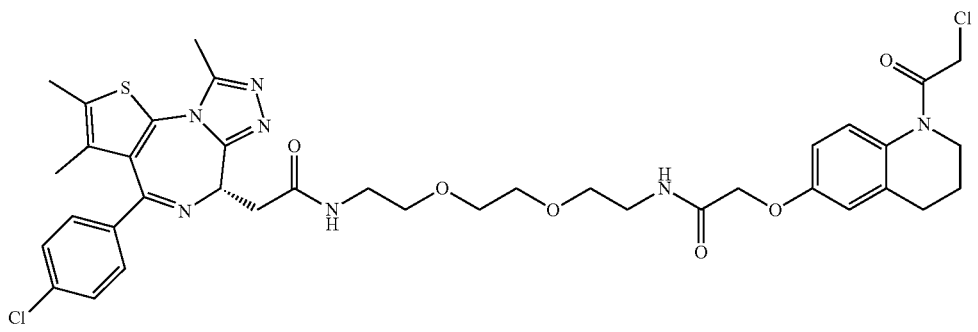
KB02-JQ1 tert-butyl (2-(2-(2-(2-((1-(2-chloroacetyl)-1,2,3,4-tetrahydroquinolin-6-yl)oxy)acetamido)ethoxy)ethoxy)ethyl)carbamate (SI-25)

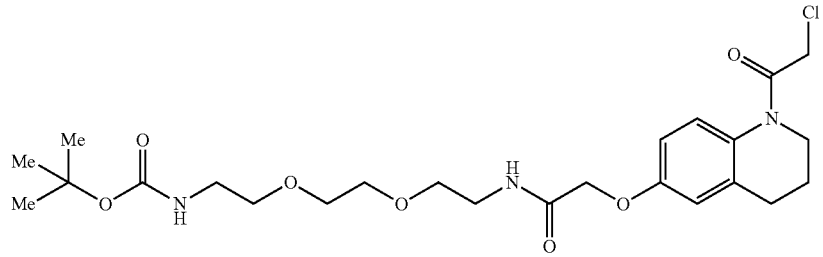 [SMILES: CC(C)(C)OC(=O)NCCOCCOCCNC(=O)COc1ccc2c(c1)CCCN2C(=O)CCl]

SI-6 (100 mg, 0.35 mmol, 1 eq.), t-Boc-N-amido-PEG2-amine (96 mg, 0.38 mmol, 1.1 eq.), EDCI (81 mg, 0.42, 1.2 eq.), N,N-diisopropylethylamine (122 µL, 0.7 mmol, 2 eq.), and catalytic 4-dimethylaminopyridine were dissolved in DCM (3 mL) and stirred at room temperature for 4 h. The reaction was diluted with DCM (10 mL) and washed with 1N HCl (15 mL), saturated NaHCO$_3$ (15 mL), and brine (15 mL). The organic layer was dried over anhydrous Na$_2$SO$_4$ and concentrated. The residue was purified via flash chromatography (EtOAc/DCM, 1:1) to provide the title compound as a colorless oil (31 mg, 17%) $^1$H NMR (500 MHz, Chloroform-d) δ 6.99 (s, 1H), 6.78 (dd, J=8.7, 2.7 Hz, 1H), 6.75 (s, 1H), 5.01 (d, J=7.1 Hz, 1H), 4.48 (s, 2H), 4.18 (s, 2H), 3.79 (t, J=6.7 Hz, 2H), 3.59 (s, 6H), 3.56 (dd, J=10.7, 5.8 Hz, 2H), 3.53 (t, J=5.3 Hz, 2H), 3.29 (t, J=5.5 Hz, 2H), 2.70 (s, 2H), 1.98 (s, 2H), 1.42 (s, 9H). HRMS (ESI) [M+H]$^+$ for C$_{24}$H$_{37}$ClN$_3$O$_7$ 514.2314, found 514.2310.

N-(2-(2-(2-aminoethoxy)ethoxy)ethyl)-2-((1-(2-chloroacetyl)-1,2,3,4-tetrahydroquinolin-6-yl)oxy)acetamide (SI-26)

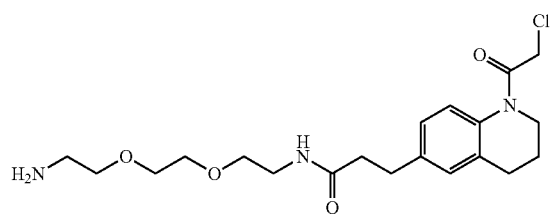 [SMILES: NCCOCCOCCNC(=O)CCc1ccc2c(c1)CCCN2C(=O)CCl]

4N HCl in dioxane (1.25 mL, 10 eq.) was added to SI-25 (31 mg, 0.05 mmol) at 0° C. The reaction was warmed to room temperature and stirred for 4 h. The solvent was removed under reduced pressure and dried under vacuum. The resulting residue was used without further purification.

(S)-2-((1-(2-chloroacetyl)-1,2,3,4-tetrahydroquinolin-6-yl)oxy)-N-(2-(2-(2-(2-(4-(4-chlorophenyl)-2,3,9-trimethyl-6H-thieno[3,2-f][1,2,4]triazolo[4,3-a][1,4]diazepin-6-yl)acetamido)ethoxy)ethoxy)ethyl)acetamide (KB02-JQ1)

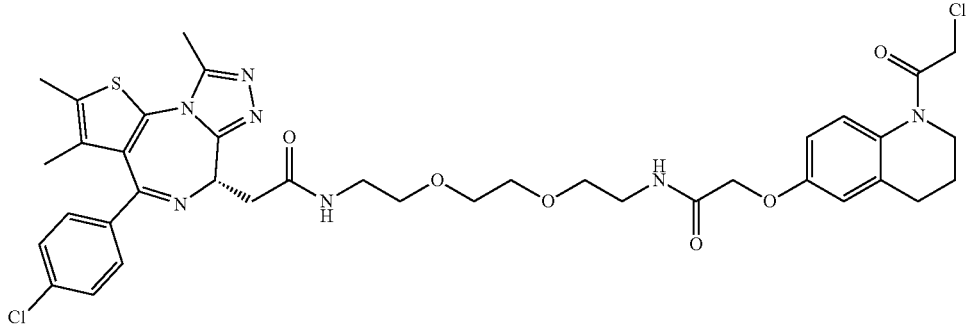 [SMILES: Cc1sc2c(c1C)C(c1ccc(Cl)cc1)=N[C@@H](CC(=O)NCCOCCOCCNC(=O)COc1ccc3c(c1)CCCN3C(=O)CCl)c1nnc(C)n1-2]

(+)-JQ1 acid (4 mg, 0.01 mmol, 1 eq.), EDCI (3 mg, 0.01 mmol, 1.2 eq.), catalytic 4-dimethylaminopyridine, and N,N-diisopropyethylamine (10 µL, 0.05 mmol, 5 eq.) were added to a solution of SI-26 (9 mg, 0.02 mmol, 2 eq.) in DCM (0.5 mL) and stirred at room temperature for 2 h. The reaction was diluted with DCM (10 mL) and washed with 1N HCl (15 mL), saturated NaHCO$_3$ (15 mL), and brine (15 mL). The organic layer was then dried over anhydrous Na$_2$SO$_4$ and concentrated. The residue was purified by prep TLC (DCM/MeOH; 19:1) to provide the title compound as an off white powder (4 mg, 47%). $^1$H NMR (500 MHz, Chloroform-d) δ 7.43-7.39 (m, 2H), 7.35-7.30 (m, 2H), 6.89 (s, 1H), 6.76 (d, J=9.9 Hz, 2H), 4.63 (dd, J=7.6, 6.5 Hz, 1H), 4.50 (s, 2H), 4.17 (s, 2H), 3.78 (s, 2H), 3.66-3.62 (m, 6H), 3.61-3.56 (m, 4H), 3.54 (d, J=7.6 Hz, 1H), 3.49 (q, J=5.4 Hz, 2H), 3.37-3.32 (m, 1H), 2.66 (d, J=6.7 Hz, 3H), 2.40 (dd, J=1.4, 0.8 Hz, 3H), 1.71-1.65 (m, 8H). HRMS (ESI) [M+H]$^+$ for C$_{34}$H$_{44}$Cl$_2$N$_7$O$_6$S 796.2445, found 796.2448.

Example 12

Table 1 illustrates the protein sequence of a DCAF16 described herein.

| Name | Sequence | SEQ ID NO: |
|---|---|---|
| DCAF16 (homo sapiens) NCBI Ref. No.: NP_060211.3 | MGPRNPSPDHLSESESEEEENISYLNESSG EEWDSSEEEDSMVPNLSPLESLAWQVKCLL KYSTTWKPLNPNSWLYHAKLLDPSTPVHIL REIGLRLSHCSHCVPKLEPIPEWPPLASCG VPPFQKPLTSPSRLSRDHATLNGALQFATK QLSRTLSRATPIPEYLKQIPNSCVSGCCCG WLTKTVKETTRTEPINTTYSYTDFQKAVNK LLTASL | 1 |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A DDB1- and CUL4-associated factor 16 (DCAF16) conjugate comprising a DCAF16 protein covalently bound to a synthetic ligand at a cysteine residue, wherein the cysteine residue is at an amino acid position corresponding to residue 58, 100, 103, 119, 173, 177, 178, or 179 of the amino acid sequence of SEQ ID NO: 1, and wherein the synthetic ligand comprises the structure of Formula (I):

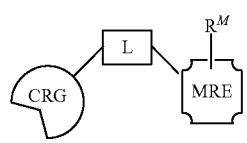

Formula (I)

wherein,

CRG is a bromodomain binder; L is a linker;

MRE is a molecular recognition element that is capable of interacting with DCAF16, wherein the MRE comprises a Michael acceptor moiety capable of forming a covalent bond to the thiol of a cysteine residue in the DCAF16 protein; and $R^M$ comprises a binding element that binds to a second protein or another compound.

2. The DCAF16 conjugate of claim 1, wherein the MRE comprises a methyl acrylate group or an alpha carbonyl chloride.

3. The DCAF16 conjugate of claim 1, wherein the MRE is covalently bound to the cysteine residue at a position corresponding to residue 58, 173, 177, 178, or 179 of the amino acid sequence of SEQ ID NO: 1 or wherein the MRE is covalently bound to the cysteine residue at a position corresponding to residue 58, 100, 103, or 119 of the amino acid sequence of SEQ ID NO: 1.

4. The DCAF16 conjugate of claim 1 wherein the Michael acceptor moiety comprises an alkene or an alkyne moiety.

5. The DCAF16 conjugate of claim 1, wherein the L is a cleavable linker or a non-cleavable linker.

6. The DCAF16 conjugate of claim 1, wherein the L is a polymeric linker.

7. The DCAF16 conjugate of claim 1, wherein the CRG binds to a target protein.

8. The DCAF16 conjugate of claim 1, wherein the bromodomain binder is a bromodomain 2 or a bromodomain 4 inhibitor.

9. The DCAF16 conjugate of claim 1, wherein the CRG comprises the structure of Formula:

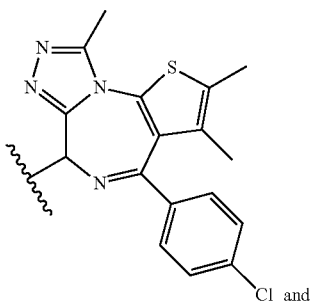

(JQ1)

and

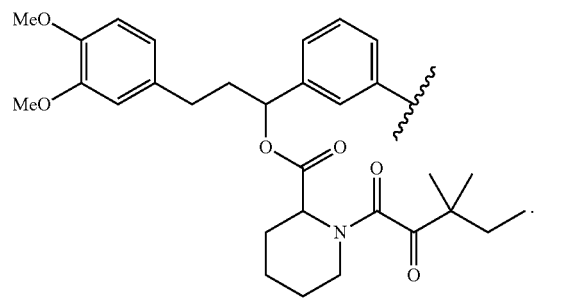

(SLF)

10. The DCAF16 conjugate of claim 1, wherein the synthetic ligand comprises the structure of Formula (IIA) or Formula (IIB):

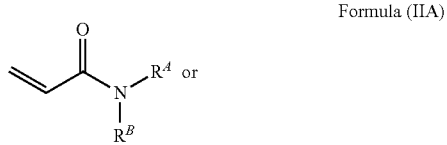

Formula (IIA)

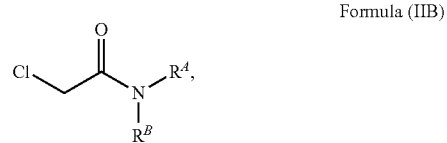

Formula (IIB)

wherein, each $R^A$ and $R^B$ is independently selected from the group consisting of H, D, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_8$cycloalkyl, substituted or unsubstituted $C_2$-$C_7$heterocycloalkyl, substituted or unsubstituted aryl, substituted or unsubstituted $C_1$-$C_3$alkylene-aryl, substituted or unsubstituted heteroaryl, and substituted or unsubstituted $C_1$-$C_3$alkylene-heteroaryl;

or $R^A$ and $R^B$ together with the nitrogen to which they are attached form a 5, 6, 7 or 8-membered heterocyclic ring A, optionally having one additional heteroatom moiety independently selected from $NR^1$, O, or S; wherein A is optionally substituted; and $R^1$ is H, D, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted aryl, or substituted or unsubstituted heteroaryl.

11. The DCAF16 conjugate of claim 1, wherein the synthetic ligand comprises the structure of Formula (III):

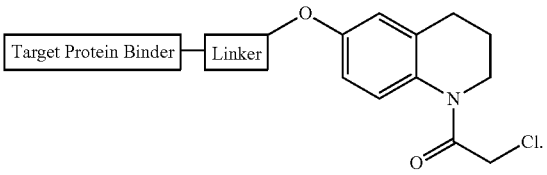

12. The DCAF16 conjugate of claim 1, wherein the linker comprises —$(CH_2CH_2O)_m$—, —NH—CO—, $CH_2O$, $C_{1-10}$ alkyl, wherein m is an integer in the range of 0 to 10.

13. The DCAF16 conjugate of claim 11, wherein the target protein binder binds to a bromodomain.

14. The DCAF16 conjugate of claim 1, wherein the synthetic ligand comprises a structures selected from the group consisting of:

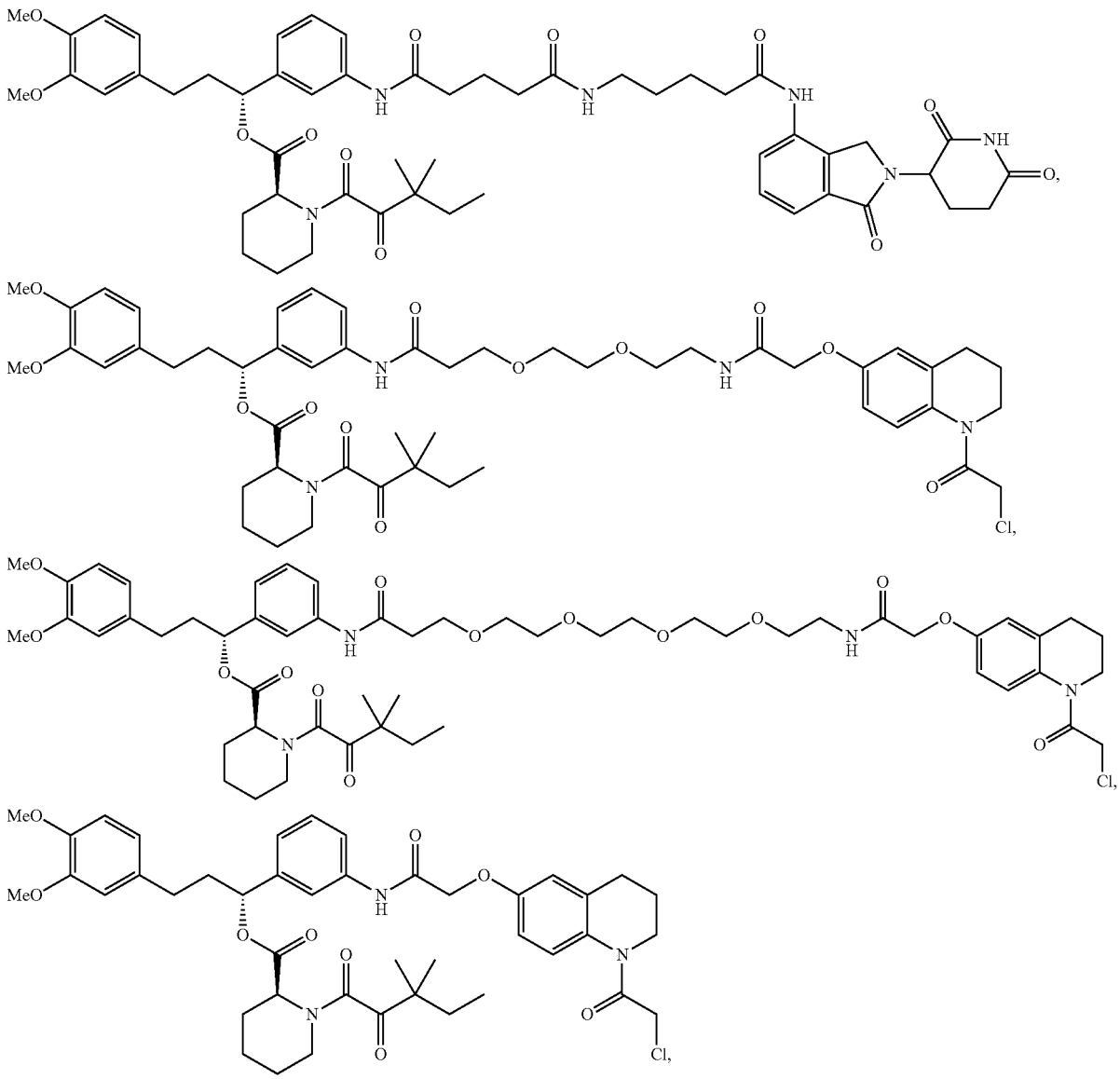

-continued

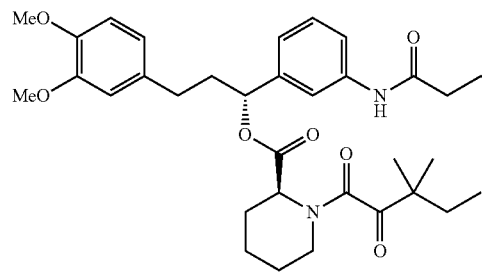
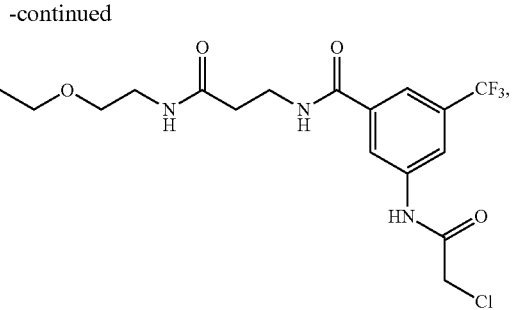

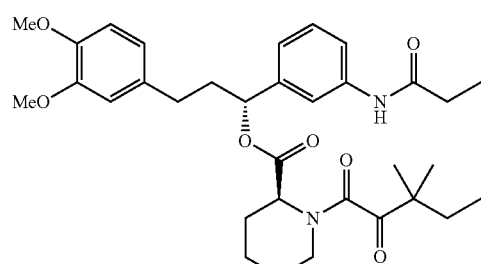
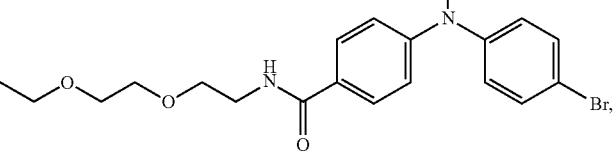

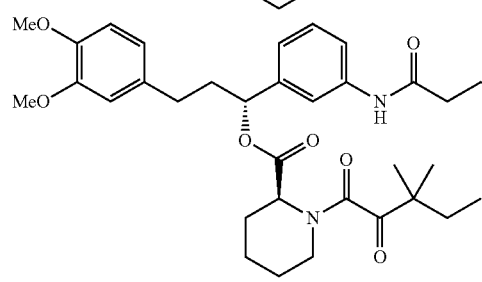
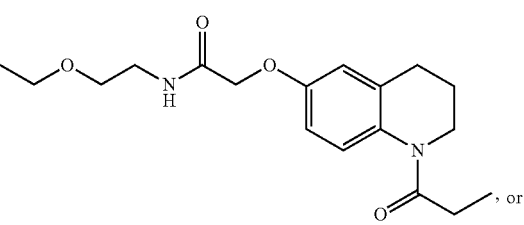

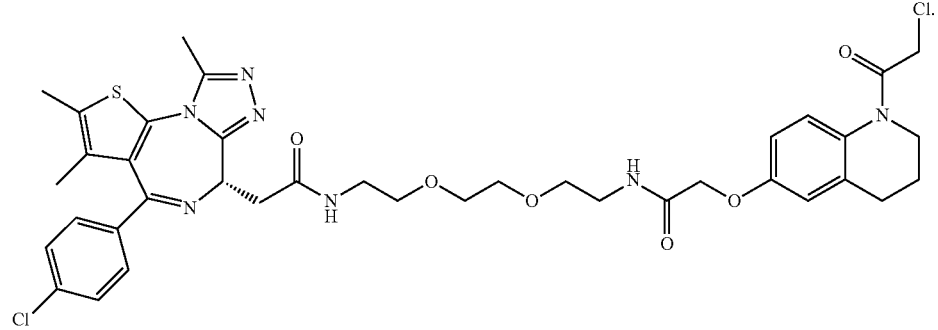

15. The DCAF16 conjugate of claim 1, wherein the MRE is covalently bound to the cysteine residue of the DCAF16 protein comprising a sequence identity that is 80%, 85%, 90%, 95%, or 99% to SEQ ID NO: 1.

16. The DCAF16 conjugate of claim 1, wherein the L comprises a polyethylene glycol (PEG) molecule.

17. The DCAF16 conjugate of claim 10, wherein
$R^A$ is H or D;
$R^B$ is aryl, substituted with one or more substituents selected from the group consisting of halogen, $C_1$-$C_4$fluoroalkyl, —CN, and —NO$_2$; or
$R^A$ and $R^B$ together with the nitrogen to which they are attached form a substituted or unsubstituted 6 or 7-membered heterocyclic ring A.

* * * * *